(12) United States Patent
Lindbo

(10) Patent No.: US 8,936,937 B2
(45) Date of Patent: Jan. 20, 2015

(54) SYSTEM FOR EXPRESSION OF GENES IN PLANTS FROM A VIRUS-BASED EXPRESSION VECTOR

(75) Inventor: John A. Lindbo, Wooster, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 995 days.

(21) Appl. No.: 12/524,812

(22) PCT Filed: Jan. 28, 2008

(86) PCT No.: PCT/US2008/001101
§ 371 (c)(1),
(2), (4) Date: Nov. 3, 2009

(87) PCT Pub. No.: WO2008/094512
PCT Pub. Date: Aug. 7, 2008

(65) Prior Publication Data
US 2010/0071085 A1    Mar. 18, 2010

Related U.S. Application Data

(60) Provisional application No. 60/898,051, filed on Jan. 29, 2007, provisional application No. 60/961,728, filed on Jul. 24, 2007.

(51) Int. Cl.
*C12N 15/40* (2006.01)
*C12N 15/82* (2006.01)
*C12N 5/10* (2006.01)
*C12N 15/64* (2006.01)
*C12N 15/67* (2006.01)

(52) U.S. Cl.
CPC ........ *C12N 15/8203* (2013.01); *C12N 15/8205* (2013.01)
USPC ................ 435/320.1; 536/24.1; 536/23.72; 435/419; 435/469; 800/294; 800/288

(58) Field of Classification Search
USPC ........................................................ 800/279
See application file for complete search history.

(56) References Cited

U.S. PATENT DOCUMENTS

| | | | |
|---|---|---|---|
| 5,766,885 | A | 6/1998 | Carrington et al. |
| 6,160,201 | A | 12/2000 | Boeshore et al. |
| 6,300,133 | B1 * | 10/2001 | Lindbo et al. ............... 435/468 |
| 6,300,134 | B1 | 10/2001 | Lindbo et al. |
| 6,503,732 | B1 * | 1/2003 | Fitchen et al. .............. 435/69.1 |
| 6,632,980 | B1 | 10/2003 | Yadav et al. |
| 6,656,726 | B1 | 12/2003 | Fitzmaurice et al. |
| 7,132,588 | B2 | 11/2006 | Fitzmaurice et al. |
| 7,235,386 | B2 | 6/2007 | Padgett et al. |
| 7,270,825 | B2 | 9/2007 | Pogue et al. |
| 2003/0208792 | A1 | 11/2003 | Fitchen et al. |
| 2007/0044170 | A1 | 2/2007 | Marillonnet et al. |
| 2007/0124831 | A1 | 5/2007 | Giritch et al. |
| 2009/0265814 | A1 | 10/2009 | Giritch et al. |

FOREIGN PATENT DOCUMENTS

| | | |
|---|---|---|
| EP | 0067553 A2 | 12/1982 |
| EP | 0573767 A1 | 12/1993 |
| EP | 1686176 A1 | 2/2006 |
| WO | 0138512 A2 | 5/2001 |
| WO | 2005/049839 A3 | 6/2005 |
| WO | 2005049839 A3 | 6/2005 |

OTHER PUBLICATIONS

Karimi et al. Gateway vectors for *Agrobacterium*-mediated plant transformation (2002) Trends in Plant Sci. 7: 193-195.*
Lico et al. Viral vectors for production of recombinant proteins in plants (2008) J. Cell. Phys. 216: 366-377.*
Hajdukiewicz et al. (1994) GenBank Accession No. AF234316.*
Marillionnet et al. Systemic *Agrobacterium tumefaciens*-mediated transfection of viral replicons for edfficient transient expression in plants (2005) Nat. Biotech. 23: 718-723.*
Benfey et al. Tissue-specific expression from CaMV 35S enhancer subdomains in early stages of plant development (1990) EMBO J. 9: 1677-1684.*
Gleba et al. Engineering viral expression vectos for plants: the 'full virus' and 'deconstructed virus' strategies (2004) Curr. Opin. Plant Biol. 7: 182-188.*
Mallory et al. The amplicon-plus system for high-level expression of transgenes in plants (2002)Nat. Biotechnol. 20: 622-625.*
Marillionnet et al. (Nat. Biotech. (2005) 23: 718-723.*
Benfey et al. (EMBO J. (1990) 9: 1677-1684.*
Gleba et al. (Curr. Opin. Plant Biol. (2004) 7: 182-188.*
Mallory et al. (Nat. Biotechnol. (2002) 20: 622-625.*
Turpen et al. (1993) J. of Virological Meth. 42: absctract.*
PCT/US08/01101, filed Jan. 28, 2008, Notification of Transmittal of the International Search Report and the Written Opinion of the International Searching authority, or the Declaration, date of mailing Sep. 24, 2008.
PCT/US2008/01101, filed Jan. 28, 2008, Notification Concerning Transmittal of International Preliminary Report on Patentability (Chapter I of the Patent Cooperation Treaty, date of mailing Aug. 13, 2009.
PCT/EP2004/012743, filed Nov. 10, 2004, Written Opinion of the International Searching Authority, date of mailing May 10, 2006.
Cao et al., Identification of an RNA Silencing Suppressor From a Plant Double-Stranded RNA Virus, Journal of Virology, Oct. 2005, pp. 13018-13027, vol. 79, No. 20.
Chiba, et al., Diverse Suppressors of RNA silencing enhance agroinfection by a viral replicon, Virology, (2006), pp. 7-14, vol. 346.
Marillonnet, et al., Systemic *Agrobacterium tumefaciens*-mediated transfection of viral replicons for efficient transient expression in plants, Nature Biotechnology, Jun. 2005, pp. 718-723, vol. 23, No. 6.

(Continued)

*Primary Examiner* — Russell Kallis
*Assistant Examiner* — Steven Bernacki
(74) *Attorney, Agent, or Firm* — MacMillan, Sobanski & Todd, LLC

(57) ABSTRACT

Modified expression vectors, including Tobacco Mosaic Virus (TMV) expression vectors, methods for modifying such vectors, and uses of the same are disclosed.

21 Claims, 38 Drawing Sheets

(56) References Cited

OTHER PUBLICATIONS

Rabindran et al., Assessment of Recombinants That Arise from the Use of a TMV-Based Transient Expression Vector, Virology, (2001), pp. 182-189, vol. 284.
Cao, X. et al., "Identification of an RNA Silencing Suppressor from a Plant Double-Stranded RNA Virus," Journal of Virology, Oct. 2005, pp. 13018-13027, vol. 79, No. 20.
Chiba, M. et al., "Diverse Suppressors of RNA Silencing Enhance Agroinfection by a Viral Replicon," Virology, 2006, pp. 7-14, vol. 346.
Database EMBL [Online], "Capsid Protein," Jul. 1993, DOI: 10.1093/nar/21.14.3325.
European Search Report, Application No. 08724880.3, Dated Aug. 4, 2010.
Marillonnet, S. et al., "Systemic *Agrobacterium tumefaciens*-Mediated Transfection of Viral Replicons for Efficient Transient Expression in Plants," Nature Biotechnology, Jun. 2005, pp. 718-723, vol. 23, No. 6.
Rabindran, S. et al., "Assessment of Recombinants That Arise from the Use of a TMV-Based Transient Expression Vector," Virology, 2001, pp. 182-189, vol. 284.
Williams, J.A. et al., "pDNAVACCultra Vector Family: High Throughput Intracellular Targeting DNA Vaccine Plasmids," Vaccine, 2006, pp. 4671-4676, vol. 24.

PCT International Preliminary Report on Patentability, PCT/US2008/001101 filed Jan. 28, 2008, dated Aug. 13, 2009, 53-28774.
PCT International Search Report and the Written Opinion, PCT/US2008/001101 filed Jan. 28, 2008, dated Sep. 24, 2008, 53-28774.
Chakrabarty, R. et al., "*Agrobacterium*-Mediated Transformation of Cauliflower: Optimization of Protocol and Development of Bt-Transgenic Cauliflower," J. Biosci., Sep. 2002, pp. 495-502, vol. 27, No. 5.
Haseloff, J. et al., "Removal of a Cryptic Intron and Subcellular Localization of Green Flourescent Protein are Required to Mark Transgenic *Arabidopsis* Plants Brightly," Proc. Natl. Acad. Sci., Mar. 1997, pp. 2122-2127, vol. 94.
Koziel, M. G. et al., "Optimizing Expression of Transgenes with an Emphasis on Post-Transcriptional Events," Plant Molecular Biology, 1996, pp. 393-405, vol. 32.
Mallory, A. C. et al., "The Amplicon-Plus System for High-Level Expression of Transgenes in Plants," Nature Biotechnology, 2002, pp. 622-625, vol. 20.
Rose, A. B., "Requirements for Intron-Mediated Enhancement of Gene Expression in *Arabidopsis*," RNA, 2002, pp. 1444-1453, vol. 8.
Simpson, C. G. et al., "Efficient Splicing of an AU-Rich Antisense Intron Sequence," Plant Molecular Biology, 1993, pp. 205-211, vol. 21.
PCT Written Opinion of the International Searching Authority, PCT/EP2004/012743 filed Nov. 10, 2004, dated Sep. 8, 2005.

* cited by examiner pJL 43 vector MCS

```
ATCGAGgccagaagagcaacctttacgtacttgctcttcaGCTTCTC
TAGCTCCGGtcttctcgttggaaatgcatgaacgagaagtcgaAGAG
```

I. Combine SapI Digested pJL 43 with PCR product.

```
...ATCGAG                              GCTTCTC...
...TAGCTCCGG                                AGAG...
         ggcctt----PCR Product---aagc
         ccggaa----PCR Product---ttcg
```

II. T4 DNA Pol + dATP/dTTP + DNA Ligase

⇓

```
...ATCGA                               GCTTCTC...
...TAGCTCCGG                              AAGAG...
         ggcctt----PCR Product---aa
             aa----PCR Product---ttcg
```

⇓

```
...ATCGAggcctt----PCR Product---aaGCTTCTC...
...TAGCTCCGGaa----pcr product---ttcgAAGAG...
```

III. Final ligated product

Figure 2 pJL 36 seq

```
GTATTTTTACAACAATTACCAACAACAACAAACAACAGAC
AACATTACAATTACTATTTACAATTACAATGGCATACACA
CAGACAGCTACCACATCAGCTTTGCTGGACACTGTCCGAG
GAAACAACTCCTTGGTCAATGATCTAGCAAAGCGTCGTCT
TTACGACACAGCGGTTGAAGAGTTTAACGCTCGTGACCGC
AGGCCCAAGGTGAACTTTTCAAAAGTAATAAGCGAGGAGC
AGACGCTTATTGCTACCCGGGCGTATCCAGAATTCCAAAT
TACATTTTATAACACGCAAAATGCCGTGCATTCGCTTGCA
GGTGGATTGCGATCTTTAGAACTGGAATATCTGATGATGC
AAATTCCCTACGGATCATTGACTTATGACATAGGCGGGAA
TTTTGCATCGCATCTGTTCAAGGGACGAGCATATGTACAC
TGCTGCATGCCCAACCTGGACGTTCGAGACATCATGCGGC
ACGAAGGCCAGAAAGACAGTATTGAACTATACCTTTCTAG
GCTAGAGAGAGGGGGAAAACAGTCCCCAACTTCCAAAAG
GAAGCATTTGACAGATACGCAGAAATTCCTGAAGACGCTG
TCTGTCACAATACTTTCCAGACATGCGAACATCAGCCGAT
GCAGCAATCAGGCAGAGTGTATGCCATTGCGCTACACAGC
ATATATGACATACCAGCCGATGAGTTCGGGGCGGCACTCT
TGAGGAAAAATGTCCATACGTGCTATGCCGCTTTCCACTT
CTCCGAGAACCTGCTTCTTGAAGATTCATGCGTCAATTTG
GACGAAATCAACGCGTGTTTTCGCGCGATGGAGACAAGT
TGACCTTTTCTTTTGCATCAGAGAGTACTCTTAATTACTG
TCATAGTTATTCTAATATTCTTAAGTATGTGTGCAAAACT
TACTTCCCGGCCTCTAATAGAGAGGTTTACATGAAGGAGT
TTTTAGTCACCAGAGTTAATACCTGGTTTTGTAAGTTTTC
TAGAATAGATACTTTTCTTTTGTACAAAGGTGTGGCCCAT
AAAAGTGTAGATAGTGAGCAGTTTTATACTGCAATGGAAG
ACGCATGGCATTACAAAAAGACTCTTGCAATGTGCAACAG
CGAGAGAATCCTCCTTGAGGATTCATCATCAGTCAATTAC
TGGTTTCCCAAAATGAGGGATATGGTCATCGTACCATTAT
TCGACATTTCTTTGGAGACTAGTAAGAGGACGCGCAAGGA
AGTCTTAGTGTCCAAGGATTTCGTGTTTACAGTGCTTAAC
CACATTCGAACATACCAGGCGAAAGCTCTTACATACGCAA
ATGTTTTGTCCTTCGTCGAATCGATTCGATCGAGGGTAAT
CATTAACGGTGTGACAGCGAGGTCCGAATGGGATGTGGAC
AAATCTTTGTTACAATCCTTGTCCATGACGTTTTACCTGC
ATACTAAGCTTGCCGTTCTAAAGGATGACTTACTGATTAG
CAAGTTTAGTCTCGGTTCGAAAACGGTGTGCCAGCATGTG
TGGATGAGATTTCGCTGGCGTTTGGGAACGCATTTCCCT
CCGTGAAAGAGAGGCTCTTGAACAGGAAACTTATCAGAGT
GGCAGGCGACGCATTAGAGATCAGGGTGCCTGATCTATAT
GTGACCTTCCACGACAGATTAGTGACTGAGTACAAGGCCT
CTGTGGACATGCCTGCGCTTGACATTAGGAAGAAGATGGA
AGAAACGGAAGTGATGTACAATGCACTTTCAGAATTATCG
GTGTTAAGGGAGTCTGACAAATTCGATGTTGATGTTTTTT
CCCAGATGTGCCAATCTTTGGAAGTTGACCCAATGACGGC
```

Figure 5B - 1

```
AGCGAAGGTTATAGTCGCGGTCATGAGCAATGAGAGCGGT
CTGACTCTCACATTTGAACGACCTACTGAGGCGAATGTTG
CGCTAGCTTTACAGGATCAAGAGAAGGCTTCAGAAGGTGC
ATTGGTAGTTACCTCAAGAGAAGTTGAAGAACCGTCCATG
AAGGGTTCGATGGCCAGAGGAGAGTTACAATTAGCTGGTC
TTGCTGGAGATCATCCGGAATCGTCCTATTCTAAGAACGA
GGAGATAGAGTCTTTAGAGCAGTTTCATATGGCGACGGCA
GATTCGTTAATTCGTAAGCAGATGAGCTCGATTGTGTACA
CGGGTCCGATTAAAGTTCAGCAAATGAAAAACTTTATCGA
TAGCCTGGTAGCATCACTATCTGCTGCGGTGTCGAATCTC
GTCAAGATCCTCAAAGATACAGCTGCTATTGACCTTGAAA
CCCGTCAAAAGTTTGGAGTCTTGGATGTTGCATCTAGGAA
GTGGTTAATCAAACCAACGGCCAAGAGTCATGCATGGGGT
GTTGTTGAAACCCACGCGAGGAAGTATCATGTGGCGCTTT
TGGAATATGATGAGCAGGGTGTGGTGACATGCGATGATTG
GAGAAGAGTAGCTGTTAGCTCTGAGTCTGTTGTTTATTCC
GACATGGCGAAACTCAGAACTCTGCGCAGACTGCTTCGAA
ACGGAGAACCGCATGTCAGTAGCGCAAAGGTTGTTCTTGT
GGACGGAGTTCCGGGCTGTGGAAAAACCAAAGAAATTCTT
TCCAGGGTTAATTTTGATGAAGATCTAATTTTAGTACCTG
GGAAGCAAGCCGCGGAAATGATCAGAAGACGTGCGAATTC
CTCAGGGATTATTGTGGCCACGAAGGACAACGTTAAAACC
GTTGATTCTTTCATGATGAATTTTGGGAAAAGCACACGCT
GTCAGTTCAAGAGGTTATTCATTGATGAAGGGTTGATGTT
GCATACTGGTTGTGTTAATTTTCTTGTGGCGATGTCATTG
TGCGAAATTGCATATGTTTACGGAGACACACAGCAGATTC
CATACATCAATAGAGTTTCAGGATTCCCGTACCCCGCCCA
TTTTGCCAAATTGGAAGTTGACGAGGTGGAGACACGCAGA
ACTACTCTCCGTTGTCCAGCCGATGTCACACATTATCTGA
ACAGGAGATATGAGGGCTTTGTCATGAGCACTTCTTCGGT
TAAAAAGTCTGTTTCGCAGGAGATGGTCGGCGGAGCCGCC
GTGATCAATCCGATCTCAAAACCCTTGCATGGCAAGATCT
TGACTTTTACCCAATCGGATAAAGAAGCTCTGCTTTCAAG
AGGGTATTCAGATGTTCACACTGTGCATGAAGTGCAAGGC
GAGACATACTCTGATGTTTCACTAGTTAGGTTAACCCCTA
CACCGGTCTCCATCATTGCAGGAGACAGCCCACATGTTTT
GGTCGCATTGTCAAGGCACACCTGTTCGCTCAAGTACTAC
ACTGTTGTTATGGATCCTTTAGTTAGTATCATTAGAGATC
TAGAGAAACTTAGCTCGTACTTGTTAGATATGTATAAGGT
CGATGCAGGAACACAATAGCAATTACAGATTGACTCGGTG
TTCAAAGGTTCCAATCTTTTTGTTGCAGCGCCAAAGACTG
GTGATATTTCTGATATGCAGTTTTACTATGATAAGTGTCT
CCCAGCAACAGCACCATGATGAATAATTTTGATGCTGTT
ACCATGAGGTTGACTGACATTTCATTGAATGTCAAAGATT
GCATATTGGATATGTCTAAGTCTGTTGCTGCGCCTAAGGA
TCAAATCAAACCACTAATACCTATGGTACGAACGGCGGCA
GAAATGCCACGCCAGACTGGACTATTGGAAAATTTAGTGG
CGATGATTAAAAGAAACTTTAACGCACCCGAGTTGTCTGG
CATCATTGATATTGAAAATACTGCATCTTTGGTTGTAGAT
AAGTTTTTTGATAGTTATTTGCTTAAAGAAAAAAGAAAAC
```

Figure 5B - 2

```
CAAATAAAAATGTTTCTTTGTTCAGTAGAGAGTCTCTCAA
TAGATGGTTAGAAAAGCAGGAACAGGTAACAATAGGCCAG
CTCGCAGATTTTGATTTTGTGGATTTGCCAGCAGTTGATC
AGTACAGACACATGATTAAAGCACAACCCAAACAAAAGTT
GGACACTTCAATCCAAACGGAGTACCCGGCTTTGCAGACG
ATTGTGTACCATTCAAAAAAGATCAATGCAATATTCGGCC
CGTTGTTTAGTGAGCTTACTAGGCAATTACTGGACAGTGT
TGATTCGAGCAGATTTTTGTTTTTCACAAGAAAGACACCA
GCGCAGATTGAGGATTTCTTCGGAGATCTCGACAGTCATG
TGCCGATGGATGTCTTGGAGCTGGATATATCAAAATACGA
CAAATCTCAGAATGAATTCCACTGTGCAGTAGAATACGAG
ATCTGGCGAAGATTGGGTTTCGAAGACTTCTTGGGAGAAG
TTTGGAAACAAGGGCATAGAAAGACCACCCTCAAGGATTA
TACCGCAGGTATAAAAACTTGCATCTGGTATCAAAGAAAG
AGCGGGACGTCACGACGTTCATTGGAAACACTGTGATCA
TTGCTGCATGTTTGGCCTCGATGCTTCCGATGGAGAAAAT
AATCAAAGGAGCCTTTTGCGGTGACGATAGTCTGCTGTAC
TTTCCAAAGGGTTGTGAGTTTCCGGATGTGCAACACTCCG
CGAATCTTATGTGGAATTTTGAAGCAAAACTGTTTAAAAA
ACAGTATGGATACTTTTGCGGAAGATATGTAATACATCAC
GACAGAGGATGCATTGTGTATTACGATCCCCTAAAGTTGA
TCTCGAAACTTGGTGCTAAACACATCAAGGATTGGGAACA
CTTGGAGGAGTTCAGAAGGTCTCTTTGTGATGTTGCTGTT
TCGTTGAACAATTGTGCGTATTACACACAGTTGGACGACG
CTGTATGGGAGGTTCATAAGACCGCCCCTCCAGGTTCGTT
TGTTTATAAAAGTCTGGTGAAGTATTTGTCTGATAAAGTT
CTTTTTAGAAGTTTGTTTATAGATGGCTCTAGTTGTTAAA
GGAAAAGTGAATATCAATGAGTTTATCGACCTGACAAAAA
TGGAGAAGATCTTACCGTCGATGTTTACCCCTGTAAAGAG
TGTTATGTGTTCCAAAGTTGATAAAATAATGGTTCATGAG
AATGAGTCATTGTCAGGGGTGAACCTTCTTAAAGGAGTTA
AGCTTATTGATAGTGGATACGTCTGTTTAGCCGGTTTGGT
CGTCACGGGCGAGTGGAACTTGCCTGACAATTGCAGAGGA
GGTGTGAGCGTGTGTCTGGTGGACAAAAGGATGGAAAGAG
CCGACGAGGCCACTCTCGGATCTTACTACACAGCAGCTGC
AAAGAAAAGATTTCAGTTCAAGGTCGTTCCCAATTATGCT
ATAACCACCCAGGACGCGATGAAAAACGTCTGGCAAGTTT
TAGTTAATATTAGAAATGTGAAGATGTCAGCGGGTTTCTG
TCCGCTTTCTCTGGAGTTTGTGTCGGTGTGTATTGTTTAT
AGAAATAATATAAAATTAGGTTTGAGAGAGAAGATTACAA
ACGTGAGAGACGGAGGGCCCATGGAACTTACAGAAGAAGT
CGTTGATGAGTTCATGGAAGATGTCCCTATGTCGATCAGG
CTTGCAAAGTTTCGATCTCGAACCGGAAAAAGAGTGATG
TCCGCAAAGGGAAAAATAGTAGTAGTGATCGGTCAGTGCC
GAACAAGAACTATAGAAATGTTAAGGATTTTGGAGGAATG
AGTTTTAAAAAGAATAATTTAATCGATGATGATTCGGAGG
CTACTGTCGCCGAATCGGATTCGTTTTAAATAGATCTTAC
AGTATCACTACTCCATCTCAGTTCGTGTTCTTGTCAittaa
ttaaCGGCCTAGGGCGGCCGCtcgagGGGTAGTCAAGATG
CATAATAAATAACGGATTGTGTCCGTAATCACACGTGGTG
```

Figure 5B - 3

```
CGTACGATAACGCATAGTGTTTTTCCCTCCACTTAAATCG
AAGGGTTGTGTCTTGGATCGCGCGGGTCAAATGTATATGG
TTCATATACATCCGCAGGCACGTAATAAAGCGAGGGGTTC
GGGTCGAGGTCGGCTGTGAAACTCGAAAAGGTTCCGGAAA
ACAAAAAAGAGAGTGGTAGGTAATAGTGTTAATAATAAGA
AAATAAATAATAGTGGTAAGAAAGGTTTGAAAGTTGAGGA
AATTGAGGATAATGTAAGTGATGACGAGTCTATCGCGTCA
TCGAGTACGTTTTAATCAATATGCCTTATACAATCAACTC
TCCGAGCCAATTTGTTTACTTAAGTTCCGCTTATGCAGAT
CCTGTGCAGCTGATCAATCTGTGTACAAATGCATTGGGTA
ACCAGTTTCAAACGCAACAAGCTAGGACAACAGTCCAACA
GCAATTTGCGGATGCCTGGAAACCTGTGCCTAGTATGACA
GTGAGATTTCCTGCATCGGATTTCTATGTGTATAGATATA
ATTCGACGCTTGATCCGTTGATCACGGCGTTATTAAATAG
CTTCGATACTAGAAATAGAATAATAGAGGTTGATAATCAA
CCCGCACCGAATACTACTGAAATCGTTAACGCGACTCAGA
GGGTAGACGATGCGACTGTAGCTATAAGGGCTTCAATCAA
TAATTTGGCTAATGAACTGGTTCGTGGAACTGGCATGTTC
AATCAAGCAAGCTTTGAGACTGCTAGTGGACTTGTCTGGA
CCACAACTCCGGCTACTTAGCTATTGTTGTGAGATTTCCT
AAAATAAAGTCACTGAAGACTTAAAATTCAGGGTGGCTGA
TACCAAAATCAGCAGTGGTTGTTCGTCCACTTAAATATAA
CGATTGTCATATCTGGATCCAACAGTTAAACCATGTGATG
GTGTATACTGTGGTATGGCGTAAAACAACGGAAAAGTCGC
TGAAGACTTAAAATTCAGGGTGGCTGATACCAAAATCAGC
AGTGGTTGTTCGTCCACTTAAAAATAACGATTGTCATATC
TGGATCCAACAGTTAAACCATGTGATGGTGTATACTGTGG
TATGGCGTAAACAACGGAGAGGTTCGAATCCTCCCCTAAC
CGCGGGTAGCGGCCCAGGTACCCGGATGTGTTTTCCGGGC
TGATGAGTCCGTGAGGACGAAACCCTGCAGGCATGCAAGC
TTGGCGTAATCATGGTCATAGCctagAgtccgcaaatcac
cagtctctctctacaaatctatctctctctatttctctcca
gaataatgtgtgagtagttcccagataagggaattaggga
tcttatagggttcgctcatgtgttgagcatataagaaac
cctagtatgtatttgtatttgtaaaatacttctatcaat
aaaatttctaattcctaaaaccaaaatccagtgacctgca
gcCCGGccggggatccactagcAGATTGTCGTTTCCCGC
CTTCAGTTTAAACTATCAGTGTTTGACAGGATATATTGGC
GGGTAAACCTAAGAGAAAAGAGCGTTTATTAGAATAATCG
GATATTTAAAAGGGCGTGAAAAGGTTTATCCGTTCGTCCA
TTTGTATGTGCATGCCAACCACAGGAGATCTCAgtaaagc
gctggctgaacccccagccggaactgaccccacaaggccc
tagcgtttgcaatgcaccaggtcatcattgacccaggcgt
gttccaccaggccgctgcctcgcaactcttcgcaggcttc
gccgacctgctcgcgccacttcttcacgcgggtggaatcc
gatccgcacatgaggcggaaggtttccagcttgagcgggt
acggctcccggtgcgagctgaaatagtcgaacatccgtcg
ggccgtcggcgacagcttgcgtacttctcccatatgaat
ttcgtgtagtggtcgccagcaaacagcacgacgattcct
cgtcgatcaggacctggcaacgggacgttttcttgccacg
```

Figure 5B - 4 gtccaggacgcggaagcggtgcagcagcgacaccgattcc
aggtgccaacgcggtcggacgtgaagcccatcgccgtcg
cctgtaggcgcgacaggcattcctcggccttcgtgtaata
ccggccattgatcgaccagcccaggtcctggcaaagctcg
tagaacgtgaaggtgatcggctcgccgatagggatgcgct
tcgcgtactccaacacctgctgccacaccagttcgtcatc
gtcggcccgcagctcgacgccggtgtaggtgatcttcacg
tcttgttgacgtggaaaatgaccttgttttgcagcgcct
cgcgcgggattttcttgttgcgcgtggtgaacagggcaga
gcgggccgtgtcgtttggcatcgctcgcatcgtgtccggc
cacggcgcaatatcgaacaaggaagctgcattccttga
tctgctgctcgtgtgtttcagcaacgcggcctgcttggc
ctcgctgacctgttttgccaggtcctcgccggcggttttt
cgcttcttggtcgtcatagttcctcgcgtgtcgatggtca
tcgacttcgccaaacctgccgcctcctgttcgagacgacg
cgaacgctccacggcggccgatggcgcgggcagggcaggg
ggagccagttgcacgctgtcgcgctcgatcttggccgtag
cttgctggaccatcgagccgacggactggaaggtttcgcg
gggcgcacgcatgacggtgcggcttgcgatggtttcggca
tcctcggcggaaaacccgcgtcgatcagttcttgcctgt
atgccttccggtcaaacgtccgattcattcaccctcctg
cgggattgccccgactcacgccggggcaatgtgccctat
tcctgatttgacccgcctggtgccttggtgtccagataat
ccaccttatcggcaatgaagtcggtcccgtagacgtctg
gccgtccttctcgtacttggtattccgaatcttgccctgc
acgaataccagcgaccccttgcccaaatacttgccgtggg
cctcggcctgagagccaaaacacttgatgcggaagaagtc
ggtgcgtcctgcttgtcgccggcatcgttgcgccacatc
taggtactaaaacaattcatccagtaaaatataatatttt
atttctcccaatcaggcttgatcccccagtaagtcaaaaa
atagctcgacatactgttcttcccccgatatcctccctgat
cgaccggacgcagaaggcaatgtcataccacttgtccgcc
ctgccgcttctcccaagatcaataaagccacttacttgc
catctttcacaaagatgttgctgtctcccaggtcgccgtg
ggaaaagacaagttcctcttcgggcttttccgtctttaaa
aaatcatacagctcgcgcggatctttaaatggagtgtctt
cttcccagttttcgcaatccacatcggccagatcgttatt
cagtaagtaatccaattcggctaagcggctgtctaagcta
ttcgtatagggacaatccgatatgtcgatggagtgaaaga
gcctgatgcactccgcatacagctcgataatctttcagg
gcttgttcatcttcatactcttccgagcaaaggacgcca
tcggcctcactcatgagcagattgctccagccatcatgcc
gttcaaagtgcaggaccttggaacaggcagcttcctttc
cagccatagcatcatgtcctttcccgttccacatcatag
gtggtcccttataccggctgtccgtcattttaaatata
ggttttcatttctcccaccagcttatataccttagcagg
agacattccttccgtatctttacgcagcgggtattttcg
atcagttttttcaatccggtgatattctcatttagcca
ttatttattccttcctcttttctacagtatttaaagata
ccccaagaagctaattataacaagacgaactccaattcac tgttccttgcattctaaaaccttaaataccagaaaacagc
tttttcaaagttgttttcaaagttggcgtataacatagta
tcgacggagccgattttgaaaccacaattatggtgatgc
tgccaactcgagagcgggccgggagggttcgagaagggg
ggcaccccccttcggcgtgcgcggtcacgcgcacagggcg
cagccctggttaaaaacaaggtttataaatattggtttaa
aagcaggttaaaagacaggttagcggtggccgaaaaacgg
gcggaaaccctttgcaaatgctggattttctgcctgtggac
agccctcaaatgtcaataggtgcgccctcatctgtcag
cactctgccctcaagtgtcaaggatcgcgccctcatct
gtcagtagtcgcgccctcaagtgtcaataccgcagggca
cttatcccaggcttgtccacatcatcgtgggaaactcg
cgtaaaatcaggcgttttcgccgatttgcgaggctggcca
gctccacgtcgccggccgaaatcgagcctgccctcatct
gtcaacgccgcgccgggtgagtcggccctcaagtgtcaa
cgtccgccctcatctgtcagtgagggccaagttttccgc
gaggtatccacaacgccggcggccggccgcggtgtctcgc
acacggctcgacggcgtttctggcgcgtttgcagggcca
tagacggccgccagcccagcgcgagggcaaccagcccgg
tgagctCTAGTGGACTGATGGGCTGCCTGTATCGAGTGGT
GATTTTGTGCCGAGCTGCCGGTCGGGGAGCTGTTGGCTGG
CTGGTGGCAGGATATATTGTGGTGTAAACAAATTGACGCT
TAGACAACTTAATAACACATTGCGGACGTTTTTAATGTAC
TGgggtggttttggtaccgggccccccctcgaggtcgacg
gtatcgataagcttgatatcgaattcctgcaggtcaacat
ggtggagcacGACACTCTCGTCTACTCCAAGAATATCAAA
GATACAGTCTCAGAAGACCAAAGGGCTATTGAGACTTTTC
AACAAAGGGTAATATCGGGAAACCTCCTCGGATTCCATTG
CCCAGCTATCTGTCACTTCATCAAAAGGACAGTAGAAAAG
GAAGGTGGCACCTACAAATGCCATCATTGCGATAAAGGAA
AGGCTATCGTTCAAGATGCCTCTGCCGACAGTGGTCCAA
AGATGGACCCCCACCCACGAGGAGCATCGTGGAAAAAGAA
GACGTTCCAACCACGTCTTCAAAGCAAGTGGATTGATGTG
ATAACATGGTGGAGCACGACACTCTCGTCTACTCCAAGAA
TATCAAAGATACAGTCTCAGAAGACCAAAGGGCTATTGAG
ACTTTTCAACAAAGGGTAATATCGGGAAACCTCCTCGGAT
TCCATTGCCCAGCTATCTGTCACTTCATCAAAAGGACAGT
AGAAAAGGAAGGTGGCACCTACAAATGCCATCATTGCGAT
AAAGGAAAGGCTATCGTTCAAGATGCCTCTGCCGACAGTG
GTCCCAAAGATGGACCCCCACCCACGAGGAGCATCGTGGA
AAAAGAAGACGTTCCAACCACGTCTTCAAAGCAAGTGGAT
TGATGTGATATCTCCACTGACGTAAGGGATGACGCACAAT
CCCACTATCCTTCGCAAGACCTTCCTCTATATAAGGAAGT
TCATTTCATTTGGAGAGG

Figure 5B - 6 pJL TRBO (aka pJL 48) Seq.

GTATTTTTACAACAATTACCAACAACAACAAACAACAGAC
AACATTACAATTACTATTTACAATTACAATGGCATACACA
CAGACAGCTACCACATCAGCTTTGCTGGACACTGTCCGAG
GAAACAACTCCTTGGTCAATGATCTAGCAAAGCGTCGTCT
TTACGACACAGCGGTTGAAGAGTTTAACGCTCGTGACCGC
AGGCCCAAGGTGAACTTTTCAAAAGTAATAAGCGAGGAGC
AGACGCTTATTGCTACCCGGGCGTATCCAGAATTCCAAAT
TACATTTTATAACACGCAAAATGCCGTGCATTCGCTTGCA
GGTGGATTGCGATCTTTAGAACTGGAATATCTGATGATGC
AAATTCCCTACGGATCATTGACTTATGACATAGGCGGGAA
TTTTGCATCGCATCTGTTCAAGGGACGAGCATATGTACAC
TGCTGCATGCCCAACCTGGACGTTCGAGACATCATGCGGC
ACGAAGGCCAGAAAGACAGTATTGAACTATACCTTTCTAG
GCTAGAGAGAGGGGGGAAAACAGTCCCCAACTTCCAAAAG
GAAGCATTTGACAGATACGCAGAAATTCCTGAAGACGCTG
TCTGTCACAATACTTTCCAGACATGCGAACATCAGCCGAT
GCAGCAATCAGGCAGAGTGTATGCCATTGCGCTACACAGC
ATATATGACATACCAGCCGATGAGTTCGGGGCGGCACTCT
TGAGGAAAAATGTCCATACGTGCTATGCCGCTTTCCACTT
CTCCGAGAACCTGCTTCTTGAAGATTCATGCGTCAATTTG
GACGAAATCAACGCGTGTTTTCGCGCGATGGAGACAAGT
TGACCTTTTCTTTTGCATCAGAGAGTACTCTTAATTACTG
TCATAGTTATTCTAATATTCTTAAGTATGTGTGCAAAACT
TACTTCCCGGCCTCTAATAGAGAGGTTTACATGAAGGAGT
TTTTAGTCACCAGAGTTAATACCTGGTTTTGTAAGTTTTC
TAGAATAGATACTTTTCTTTTGTACAAAGGTGTGGCCCAT
AAAAGTGTAGATAGTGAGCAGTTTTATACTGCAATGGAAG
ACGCATGGCATTACAAAAAGACTCTTGCAATGTGCAACAG
CGAGAGAATCCTCCTTGAGGATTCATCATCAGTCAATTAC
TGGTTTCCCAAAATGAGGGATATGGTCATCGTACCATTAT
TCGACATTTCTTTGGAGACTAGTAAGAGGACGCGCAAGGA
AGTCTTAGTGTCCAAGGATTTCGTGTTTACAGTGCTTAAC
CACATTCGAACATACCAGGCGAAAGCTCTTACATACGCAA
ATGTTTTGTCCTTCGTCGAATCGATTCGATCGAGGGTAAT
CATTAACGGTGTGACAGCGAGGTCCGAATGGGATGTGGAC
AAATCTTTGTTACAATCCTTGTCCATGACGTTTTACCTGC
ATACTAAGCTTGCCGTTCTAAAGGATGACTTACTGATTAG
CAAGTTTAGTCTCGGTTCGAAAACGGTGTGCCAGCATGTG
TGGGATGAGATTTCGCTGGCGTTTGGGAACGCATTTCCCT
CCGTGAAAGAGAGGCTCTTGAACAGGAAACTTATCAGAGT
GGCAGGCGACGCATTAGAGATCAGGGTGCCTGATCTATAT
GTGACCTTCCACGACAGATTAGTGACTGAGTACAAGGCCT
CTGTGGACATGCCTGCGCTTGACATTAGGAAGAAGATGGA
AGAAACGGAAGTGATGTACAATGCACTTTCAGAATTATCG
GTGTTAAGGGAGTCTGACAAATTCGATGTTGATGTTTTTT
CCCAGATGTGCCAATCTTTGGAAGTTGACCCAATGACGGC
AGCGAAGGTTATAGTCGCGGTCATGAGCAATGAGAGCGGT
CTGACTCTCACATTTGAACGACCTACTGAGGCGAATGTTG

Figure 7B - 1

```
CGCTAGCTTTACAGGATCAAGAGAAGGCTTCAGAAGGTGC
ATTGGTAGTTACCTCAAGAGAAGTTGAAGAACCGTCCATG
AAGGGTTCGATGGCCAGAGGAGAGTTACAATTAGCTGGTC
TTGCTGGAGATCATCCGGAATCGTCCTATTCTAAGAACGA
GGAGATAGAGTCTTTAGAGCAGTTTCATATGGCGACGGCA
GATTCGTTAATTCGTAAGCAGATGAGCTCGATTGTGTACA
CGGGTCCGATTAAAGTTCAGCAAATGAAAAACTTTATCGA
TAGCCTGGTAGCATCACTATCTGCTGCGGTGTCGAATCTC
GTCAAGATCCTCAAAGATACAGCTGCTATTGACCTTGAAA
CCCGTCAAAAGTTTGGAGTCTTGGATGTTGCATCTAGGAA
GTGGTTAATCAAACCAACGGCCAAGAGTCATGCATGGGGT
GTTGTTGAAACCCACGCGAGGAAGTATCATGTGGCGCTTT
TGGAATATGATGAGCAGGGTGTGGTGACATGCGATGATTG
GAGAAGAGTAGCTGTTAGCTCTGAGTCTGTTGTTTATTCC
GACATGGCGAAACTCAGAACTCTGCGCAGACTGCTTCGAA
ACGGAGAACCGCATGTCAGTAGCGCAAAGGTTGTTCTTGT
GGACGGAGTTCCGGGCTGTGGAAAAACCAAAGAAATTCTT
TCCAGGGTTAATTTTGATGAAGATCTAATTTTAGTACCTG
GGAAGCAAGCCGCGGAAATGATCAGAAGACGTGCGAATTC
CTCAGGGATTATTGTGGCCACGAAGGACAACGTTAAAACC
GTTGATTCTTTCATGATGAATTTGGGAAAAGCACACGCT
GTCAGTTCAAGAGGTTATTCATTGATGAAGGGTTGATGTT
GCATACTGGTTGTGTTAATTTTCTTGTGGCGATGTCATTG
TGCGAAATTGCATATGTTTACGGAGACACACAGCAGATTC
CATACATCAATAGAGTTTCAGGATTCCCGTACCCCGCCCA
TTTTGCCAAATTGGAAGTTGACGAGGTGGAGACACGCAGA
ACTACTCTCCGTTGTCCAGCCGATGTCACACATTATCTGA
ACAGGAGATATGAGGGCTTTGTCATGAGCACTTCTTCGGT
TAAAAAGTCTGTTTCGCAGGAGATGGTCGGCGGAGCCGCC
GTGATCAATCCGATCTCAAAACCCTTGCATGGCAAGATCT
TGACTTTTACCCAATCGGATAAAGAAGCTCTGCTTTCAAG
AGGGTATTCAGATGTTCACACTGTGCATGAAGTGCAAGGC
GAGACATACTCTGATGTTTCACTAGTTAGGTTAACCCCTA
CACCGGTCTCCATCATTGCAGGAGACAGCCCACATGTTTT
GGTCGCATTGTCAAGGCACACCTGTTCGCTCAAGTACTAC
ACTGTTGTTATGGATCCTTTAGTTAGTATCATTAGAGATC
TAGAGAAACTTAGCTCGTACTTGTTAGATATGTATAAGGT
CGATGCAGGAACACAATAGCAATTACAGATTGACTCGGTG
TTCAAAGGTTCCAATCTTTTTGTTGCAGCGCCAAAGACTG
GTGATATTTCTGATATGCAGTTTTACTATGATAAGTGTCT
CCCAGGCAACAGCACCATGATGAATAATTTTGATGCTGTT
ACCATGAGGTTGACTGACATTTCATTGAATGTCAAAGATT
GCATATTGGATATGTCTAAGTCTGTTGCTGCGCCTAAGGA
TCAAATCAAACCACTAATACCTATGGTACGAACGGCGGCA
GAAATGCCACGCCAGACTGGACTATTGGAAAATTTAGTGG
CGATGATTAAAAGAAACTTTAACGCACCCGAGTTGTCTGG
CATCATTGATATTGAAAATACTGCATCTTTGGTTGTAGAT
AAGTTTTTTGATAGTTATTTGCTTAAAGAAAAAAGAAAAC
CAAATAAAAATGTTTCTTTGTTCAGTAGAGAGTCTCTCAA
TAGATGGTTAGAAAAGCAGGAACAGGTAACAATAGGCCAG
```

Figure 7B - 2

```
CTCGCAGATTTTGATTTTGTGGATTTGCCAGCAGTTGATC
AGTACAGACACATGATTAAAGCACAACCCAAACAAAAGTT
GGACACTTCAATCCAAACGGAGTACCCGGCTTTGCAGACG
ATTGTGTACCATTCAAAAAGATCAATGCAATATTCGGCC
CGTTGTTTAGTGAGCTTACTAGGCAATTACTGGACAGTGT
TGATTCGAGCAGATTTTGTTTTTCACAAGAAAGACACCA
GCGCAGATTGAGGATTTCTTCGGAGATCTCGACAGTCATG
TGCCGATGGATGTCTTGGAGCTGGATATATCAAAATACGA
CAAATCTCAGAATGAATTCCACTGTGCAGTAGAATACGAG
ATCTGGCGAAGATTGGGTTTCGAAGACTTCTTGGGAGAAG
TTTGGAAACAAGGGCATAGAAAGACCACCCTCAAGGATTA
TACCGCAGGTATAAAAACTTGCATCTGGTATCAAAGAAAG
AGCGGGACGTCACGACGTTCATTGGAAACACTGTGATCA
TTGCTGCATGTTTGGCCTCGATGCTTCCGATGGAGAAAAT
AATCAAAGGAGCCTTTTGCGGTGACGATAGTCTGCTGTAC
TTTCCAAAGGGTTGTGAGTTTCCGGATGTGCAACACTCCG
CGAATCTTATGTGGAATTTTGAAGCAAAACTGTTTAAAAA
ACAGTATGGATACTTTTGCGGAAGATATGTAATACATCAC
GACAGAGGATGCATTGTGTATTACGATCCCCTAAAGTTGA
TCTCGAAACTTGGTGCTAAACACATCAAGGATTGGGAACA
CTTGGAGGAGTTCAGAAGGTCTCTTTGTGATGTTGCTGTT
TCGTTGAACAATTGTGCGTATTACACACAGTTGGACGACG
CTGTATGGGAGGTTCATAAGACCGCCCCTCCAGGTTCGTT
TGTTTATAAAAGTCTGGTGAAGTATTTGTCTGATAAAGTT
CTTTTTAGAAGTTTGTTTATAGATGGCTCTAGTTGTTAAA
GGAAAAGTGAATATCAATGAGTTTATCGACCTGACAAAAA
TGGAGAAGATCTTACCGTCGATGTTTACCCCTGTAAAGAG
TGTTATGTGTTCCAAAGTTGATAAAATAATGGTTCATGAG
AATGAGTCATTGTCAGGGGTGAACCTTCTTAAAGGAGTTA
AGCTTATTGATAGTGGATACGTCTGTTTAGCCGGTTTGGT
CGTCACGGGCGAGTGGAACTTGCCTGACAATTGCAGAGGA
GGTGTGAGCGTGTGTCTGGTGGACAAAAGGATGGAAAGAG
CCGACGAGGCCACTCTCGGATCTTACTACACAGCAGCTGC
AAAGAAAAGATTTCAGTTCAAGGTCGTTCCCAATTATGCT
ATAACCACCCAGGACGCGATGAAAAACGTCTGGCAAGTTT
TAGTTAATATTAGAAATGTGAAGATGTCAGCGGGTTTCTG
TCCGCTTTCTCTGGAGTTTGTGTCGGTGTGTATTGTTTAT
AGAAATAATATAAAATTAGGTTTGAGAGAGAAGATTACAA
ACGTGAGAGACGGAGGGCCCATGGAACTTACAGAAGAAGT
CGTTGATGAGTTCATGGAAGATGTCCCTATGTCGATCAGG
CTTGCAAAGTTTCGATCTCGAACCGGAAAAAAGAGTGATG
TCCGCAAAGGGAAAAATAGTAGTAGTGATCGGTCAGTGCC
GAACAAGAACTATAGAAATGTTAAGGATTTTGGAGGAATG
AGTTTTAAAAGAATAATTTAATCGATGATGATTCGGAGG
CTACTGTCGCCGAATCGGATTCGTTTTAAATAGATCTTAC
AGTATCACTACTCCATCTCAGTTCGTGTTCTTGTCAttaa
ttaacggctagggcggccgcGGTCCTGCAACTTGAggta
gtcaagatgcataataaataacggattgtgtccgtaatca
cacgtggtgcgtacgataacgcatagtgttttccctcca
cttaaatcgaagggttgtgtcttggatcgcgcgggtcaaa
```

Figure 7B - 3

```
tgtatatggttcatatacatccgcaggcacgtaataaagc
gaggggttcgaatcccccgttaccccggtaggggccca
gGTACCcggAtgtgtttccgggctgatgagtccgtgagg
acgaaaccCTGCAGGCATGCAAGCTTGGCGTAATcatggt
catAGCctagctagagtccgcaaatcaccagtctctctct
acaaatctatctctctcttattttctccagaataatgtgtg
agtagttcccagataagggaattagggttcttataggggtt
tcgctcatgtgttgtgcatataagaaaccettagtatgta
tttgtatttgtaaatacttctatcaataaaatttctaat
tcctaaaaccaaatccagtgacctgcagcCCGGccgggg
gatccactagcAGATTGTCGTTTCCCGCCTTCAGTTTAAA
CTATCAGTGTTTGACAGGATATATTGGCGGGTAAACCTAA
GAGAAAAGAGCGTTTATTAGAATAATCGGATATTTAAAAG
GGCGTGAAAAGGTTTATCCGTTCGTCCATTTGTATGTGCA
TGCCAACCACAGGAGATCTCAgtaaagcgctggctgaacc
cccagccggaactgaccccacaaggccctagcgtttgcaa
tgcaccaggtcatcattgacccaggcgtgttccaccaggc
cgctgcctcgcaactcttcgcaggcttcgccgacctgctc
gcgccacttcttcacgcgggtggaatccgatccgcacatg
aggcggaaggttccagcttgagcgggtacggctcccggt
gcgagctgaatagtcgaacatccgtcgggccgtcggcga
cagctgcggtactctcccatatgaatttcgtgtagtgg
tcgccagcaaacagcacgacgattcctcgtcgatcagga
cctggcaacgggacgttttctgccacggtccaggacgcg
gaagcggtgcagcagcgacaccgattccaggtgccaacg
cggtcggacgtgaagccatcgccgtcgcctgtaggcgcg
acaggcattcctcggcctcgtgtaataccgccattgat
cgaccagccaggtcctggcaaagctcgtagaacgtgaag
gtgatcggctcgccgatagggtgcgttcgcgtactcca
acacctgctgccacaccagttcgtcatcgtcggcccgcag
ctcgacgccggtgtaggtgatcttcacgtccttgttgacg
tggaaaatgaccttgttttgcagcgcctcgcgcgggattt
tcttgttgcgcgtggtgaacagggcagagcgggccgtgtc
gtttggcatcgctcgcatcgtgtccggccacggcgcaata
tcgaacaaggaaaagctgcattcctgatctgctgcttcg
tgtgttcagcaacgcgggctgcttggcctcgctgaccctg
ttttgccaggtcctcgccggcggttttcgcttcttggtc
gtcatagttcctcgcgtgtcgatggtcatcgacttcgcca
aacctgccgcctcctgttcgagacgacgcgaacgctccac
ggcggccgatggcgcggcagggcgggggagccagttgc
acgctgtcgcgctcgatcttggcgtagcttgctggacca
tcgagccgacggactggaaggttcgcggggcgcacgcat
gacggtgcggcttgcgatggtttcggcatcctcggcggaa
aacccgcgtcgatcagttcttgcctgtatgccttccggt
caaacgtccgattcattcaccctcctgcgggattgcccc
gactcacgccggggcaatgtgccttattcctgattgac
ccgcctggtgccttggtgtccagataatccaccttatcgg
caatgaagtcggtccgtagaccgctggccgtccttctc
gtacttggtattccgaatcttgccctgcacgaataccagc
gacccttgcccaaatacttgccgtgggcctcggcctgag
```

Figure 7B - 4 agccaaaacacttgatgcggaagaagtcggtgcgctcctg
cttgtcgccggcatcgttgcgccacatctaggtactaaaa
caattcatccagtaaaatataatattttatttctcccaa
tcaggcttgatccccagtaagtcaaaaatagctcgacat
actgttcttccccgatatctccctgatcgacggacgca
gaaggcaatgtcataccacttgtccgccctgccgcttctc
ccaagatcaataaagccacttacttgccatcttcacaa
agatgttgctgtctcccaggtcgccgtgggaaaagacaag
ttcctcttcgggctttccgtctttaaaaatcatacagc
tcgcgcggatctttaaatggagtgtcttcttcccagtttt
cgcaatccacatcggccagatcgttattcagtaagtaatc
caattcggctaagcggctgtctaagctattcgtataggga
caatccgatatgtcgatggagtgaaagagcctgatgcact
ccgcatacagctcgataatctttcagggcttttgttcatc
ttcatactcttccgagcaaaggacgccatcggcctcactc
atgagcagattgctccagccatcatgccgttcaaagtgca
ggacctttggaacaggcagcttcctccagccatagcat
catgtcctttccgttccacatcataggtggtccctta
taccggctgtccgtcattttaaatataggttttcattt
ctcccaccagcttatataccttagcaggagacattcctc
cgtatcttttacgcagcggtattttcgatcagtttttc
aattccggtatattctcattttagccatttattattcc
ttcctcttttctacagtatttaaagatacccaagaagct
aattataacaagacgaactccaattcactgttccttgcat
tctaaaacctaaataccagaaaacagcttttttcaaagtt
gtttcaaagttggcgtataacatagtatcgacggagccg
attttgaaaccacaatatgggtgatgctgccaactcgag
atcgggccgggagggttcgagaagggggggcacccccctt
cggcgtgcgcggtcacgcgcacagggcgcagccctggtta
aaaacaaggtttataaatattggtttaaaagcaggttaaa
agacaggttagcggtgccgaaaaacgggcggaaaccctt
gcaaatgctggatttctgcctgtggacagccctcaaat
gtcaataggtgcgcccctcatctgtcagcactctgccct
caagtgtcaaggatcgcgccctcatctgtcagtagtcgc
gcccctcaagtgtcaataccgcagggcacttatccccagg
cttgtccacatcatctgtgggaaactcgcgtaaaatcagg
cgttttcgccgattgcgaggctggccagctccacgtcgc
cggccgaaatcgagcctgccctcatcgtcaacgccgcg
ccgggtgagtcggccctcaagtgtcaacgtccgccctc
atctgtcagtgagggccaagttttccgcgaggtatccaca
acgccggcggccggccgcggtgtctgcacacggcttcga
cggcgtttctggcgcgtttgcagggccatagacggccgcc
agcccagcggcgagggcaaccagcccgatgagctCTAGTG
GACTGATGGGCTGCCTGTATCGAGTGGTGATTTTGTGCCG
AGCTGCCGGTCGGGGAGCTGTTGGCTGGCTGGTGGCAGGA
TATATTGTGGTGTAAACAAATTGACGCTTAGACAACTTAA
TAACACATTGCGGACGTTTTTAATGTACTGgggtggttt
ggtaccgggccccctcgaggtcgacggtatcgataagc
ttgatatcgaattcctgcaggtcaacatggtggagcacGA
CACTCTCGTCTACTCCAAGAATATCAAAGATACAGTCTCA

Figure 7B - 5

```
GAAGACCAAAGGGCTATTGAGACTTTTCAACAAAGGGTAA
TATCGGGAAACCTCCTCGGATTCCATTGCCCAGCTATCTG
TCACTTCATCAAAAGGACAGTAGAAAAGGAAGGTGGCACC
TACAAATGCCATCATTGCGATAAAGGAAAGGCTATCGTTC
AAGATGCCTCTGCCGACAGTGGTCCCAAAGATGGACCCCC
ACCCACGAGGAGCATCGTGGAAAAAGAAGACGTTCCAACC
ACGTCTTCAAAGCAAGTGGATTGATGTGATAACATGGTGG
AGCACGACACTCTCGTCTACTCCAAGAATATCAAAGATAC
AGTCTCAGAAGACCAAAGGGCTATTGAGACTTTTCAACAA
AGGGTAATATCGGGAAACCTCCTCGGATTCCATTGCCCAG
CTATCTGTCACTTCATCAAAAGGACAGTAGAAAAGGAAGG
TGGCACCTACAAATGCCATCATTGCGATAAAGGAAAGGCT
ATCGTTCAAGATGCCTCTGCCGACAGTGGTCCCAAAGATG
GACCCCCACCCACGAGGAGCATCGTGGAAAAAGAAGACGT
TCCAACCACGTCTTCAAAGCAAGTGGATTGATGTGATATC
TCCACTGACGTAAGGGATGACGCACAATCCCACTATCCTT
CGCAAGACCTTCCTCTATATAAGGAAGTTCATTTCATTTG
GAGAGG
```

Figure 7B - 6

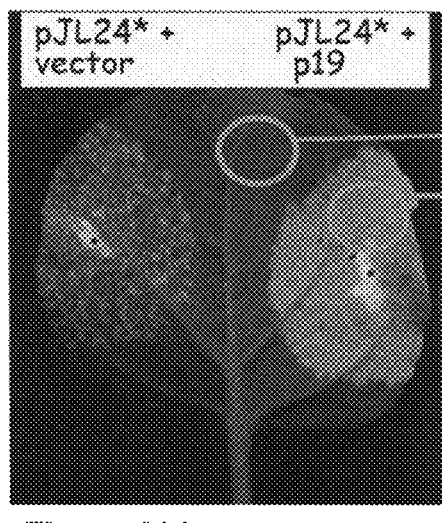
Figure 16A
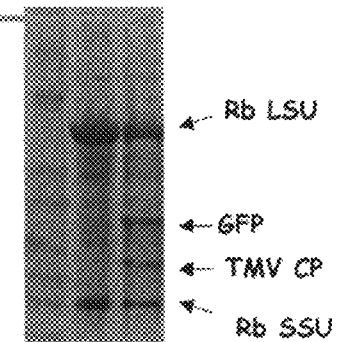
Figure 16C
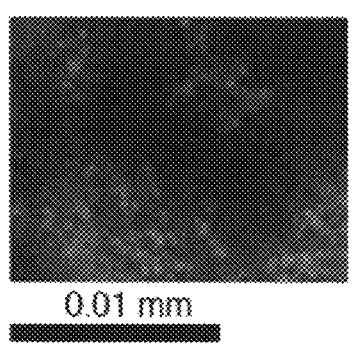 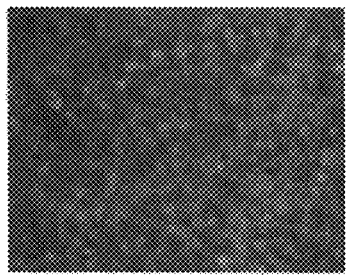
Figure 16B

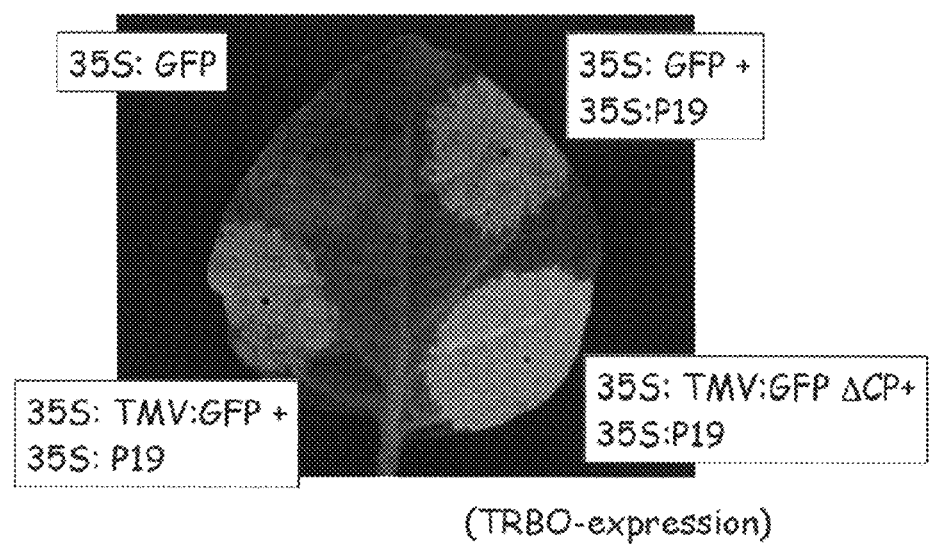
Figure 20
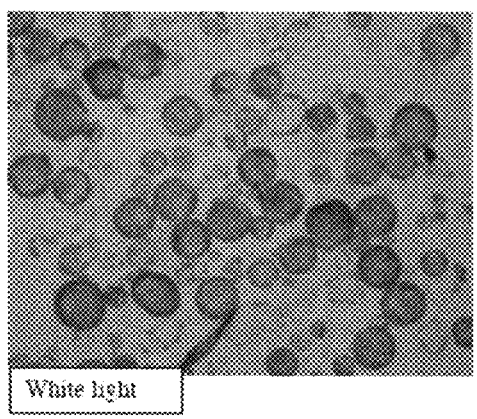 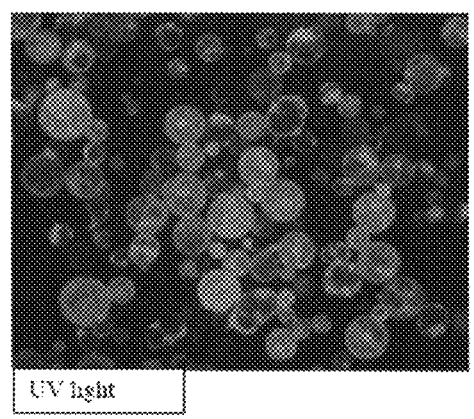
Figure 21A                    Figure 21B pJL 66 seq

```
GTATTTTTACAACAATTACCAACAACAACAAACAACAGAC
AACATTACAATTACTATTTACAATTACAATGGCATACACA
CAGACAGCTACCACATCAGCTTTGCTGGACACTGTCCGAG
GAAACAACTCCTTGGTCAATGATCTAGCAAAGCGTCGTCT
TTACGACACAGCGGTTGAAGAGTTTAACGCTCGTGACCGC
AGGCCCAAGGTGAACTTTTCAAAAGTAATAAGCGAGGAGC
AGACGCTTATTGCTACCCGGGCGTATCCAGAATTCCAAAT
TACATTTTATAACACGCAAAATGCCGTGCATTCGCTTGCA
GGTGGATTGCGATCTTTAGAACTGGAATATCTGATGATGC
AAATTCCCTACGGATCATTGACTTATGACATAGGCGGGAA
TTTTGCATCGCATCTGTTCAAGGGACGAGCATATGTACAC
TGCTGCATGCCCAACCTGGACGTTCGAGACATCATGCGGC
ACGAAGGCCAGAAAGACAGTATTGAACTATACCTTTCTAG
GCTAGAGAGAGGGGGGAAAACAGTCCCCAACTTCCAAAAG
GAAGCATTTGACAGATACGCAGAAATTCCTGAAGACGCTG
TCTGTCACAATACTTTCCAGACATGCGAACATCAGCCGAT
GCAGCAATCAGGCAGAGTGTATGCCATTGCGCTACACAGC
ATATATGACATACCAGCCGATGAGTTCGGGGCGGCACTCT
TGAGGAAAAATGTCCATACGTGCTATGCCGCTTTCCACTT
CTCCGAGAACCTGCTTCTTGAAGATTCATGCGTCAATTTG
GACGAAATCAACGCGTGTTTTCGCGCGATGGAGACAAGT
TGACCTTTTCTTTTGCATCAGAGAGTACTCTTAATTACTG
TCATAGTTATTCTAATATTCTTAAGTATGTGTGCAAAACT
TACTTCCCGGCCTCTAATAGAGAGGTTTACATGAAGGAGT
TTTTAGTCACCAGAGTTAATACCTGGTTTTGTAAGTTTTC
TAGAATAGATACTTTTCTTTTGTACAAAGGTGTGGCCCAT
AAAAGTGTAGATAGTGAGCAGTTTTATACTGCAATGGAAG
ACGCATGGCATTACAAAAAGACTCTTGCAATGTGCAACAG
CGAGAGAATCCTCCTTGAGGATTCATCATCAGTCAATTAC
TGGTTTCCCAAAATGAGGGATATGGTCATCGTACCATTAT
TCGACATTTCTTTGGAGACTAGTAAGAGGACGCGCAAGGA
AGTCTTAGTGTCCAAGGATTTCGTGTTTACAGTGCTTAAC
CACATTCGAACATACCAGGCGAAAGCTCTTACATACGCAA
ATGTTTTGTCCTTCGTCGAATCGATTCGATCGAGGGTAAT
CATTAACGGTGTGACAGCGAGGTCCGAATGGGATGTGGAC
AAATCTTTGTTACAATCCTTGTCCATGACGTTTTACCTGC
ATACTAAGCTTGCCGTTCTAAAGGATGACTTACTGATTAG
CAAGTTTAGTCTCGGTTCGAAAACGGTGTGCCAGCATGTG
TGGGATGAGATTTCGCTGGCGTTTGGGAACGCATTTCCCT
CCGTGAAAGAGAGGCTCTTGAACAGGAAACTTATCAGAGT
GGCAGGCGACGCATTAGAGATCAGGGTGCCTGATCTATAT
GTGACCTTCCACGACAGATTAGTGACTGAGTACAAGGCCT
CTGTGGACATGCCTGCGCTTGACATTAGGAAGAAGATGGA
AGAAACGGAAGTGATGTACAATGCACTTTCAGAATTATCG
GTGTTAAGGGAGTCTGACAAATTCGATGTTGATGTTTTTT
CCCAGATGTGCCAATCTTTGGAAGTTGACCCAATGACGGC
AGCGAAGGTTATAGTCGCGGTCATGAGCAATGAGAGCGGT
CTGACTCTCACATTTGAACGACCTACTGAGGCGAATGTTG
```

Figure 22 - 1

```
CGCTAGCTTTACAGGATCAAGAGAAGGCTTCAGAAGGTGC
ATTGGTAGTTACCTCAAGAGAAGTTGAAGAACCGTCCATG
AAGGGTTCGATGGCCAGAGGAGAGTTACAATTAGCTGGTC
TTGCTGGAGATCATCCGGAATCGTCCTATTCTAAGAACGA
GGAGATAGAGTCTTTAGAGCAGTTTCATATGGCGACGGCA
GATTCGTTAATTCGTAAGCAGATGAGCTCGATTGTGTACA
CGGGTCCGATTAAAGTTCAGCAAATGAAAAACTTTATCGA
TAGCCTGGTAGCATCACTATCTGCTGCGGTGTCGAATCTC
GTCAAGATCCTCAAAGATACAGCTCCTATTGACCTTGAAA
CCCGTCAAAAGTTTGGAGTCTTGGATGTTGCATCTAGGAA
GTGGTTAATCAAACCAACGGCCAAGAGTCATGCATGGGGT
GTTGTTGAAACCCACGCGAGGAAGTATCATGTGGCGCTTT
TGGAATATGATGAGCAGGGTGTGGTGACATGCGATGATTG
GAGAAGAGTAGCTGTTAGCTCTGAGTCTGTTGTTTATTCC
GACATGGCGAAACTCAGAACTCTGCGCAGACTGCTTCGAA
ACGGAGAACCGCATGTCAGTAGCGCAAAGGTTGTTCTTGT
GGACGGAGTTCCGGGCTGTGGAAAAACCAAAGAAATTCTT
TCCAGGGTTAATTTTGATGAAGATCTAATTTTAGTACCTG
GGAAGCAAGCCGCGGAAATGATCAGAAGACGTGCGAATTC
CTCAGGGATTATTGTGGCCACGAAGGACAACGTTAAAACC
GTTGATTCTTTCATGATGAATTTTGGGAAAAGCACACGCT
GTCAGTTCAAGAGGTTATTCATTGATGAAGGGTTGATGTT
GCATACTGGTTGTGTTAATTTTCTTGTGGCGATGTCATTG
TGCGAAATTGCATATGTTACGGAGACACACAGCAGATTC
CATACATCAATAGAGTTTCAGGATTCCCGTACCCCGCCCA
TTTTGCCAAATTGGAAGTTGACGAGGTGGAGACACGCAGA
ACTACTCTCCGTTGTCCAGCCGATGTCACACATTATCTGA
ACAGGAGATATGAGGGCTTTGTCATGAGCACTTCTTCGGT
TAAAAAGTCTGTTTCGCAGGAGATGGTCGGCGGAGCCGCC
GTGATCAATCCGATCTCAAAACCCTTGCATGGCAAGATCT
TGACTTTTACCCAATCGGATAAAGAAGCTCTGCTTTCAAG
AGGGTATTCAGATGTTCACACTGTGCATGAAGTGCAAGGC
GAGACATACTCTGATGTTCACTAGTTAGGTTAACCCCTA
CACCGGTCTCCATCATTGCAGGAGACAGCCCACATGTTTT
GGTCGCATTGTCAAGGCACACCTGTTCGCTCAAGTACTAC
ACTGTTGTTATGGATCCTTTAGTTAGTATCATTAGAGATC
TAGAGAAACTTAGCTCGTACTTGTTAGATATGTATAAGGT
CGATGCAGGAACACAATAGCAATTACAGATTGACTCGGTG
TTCAAAGGTTCCAATCTTTTTGTTGCAGCGCCAAAGACTG
GTGATATTTCTGATATGCAGTTTTACTATGATAAGTGTCT
CCCAGGCAACAGCACCATGATGAATAATTTTGATGCTGTT
ACCATGAGGTTGACTGACATTTCATTGAATGTCAAAGATT
GCATATTGGATATGTCTAAGTCTGTTGCTGCGCCTAAGGA
TCAAATCAAACCACTAATACCTATGGTACGAACGGCGGCA
GAAATGCCACGCCAGACTGGACTATTGGAAAATTTAGTGG
CGATGATTAAAAGAAACTTTAACGCACCCGAGTTGTCTGG
CATCATTGATATTGAAAATACTGCATCTTTGGTTGTAGAT
AAGTTTTTTGATAGTTATTTGCTTAAAGAAAAAAGAAAAC
CAAATAAAAATGTTTCTTTGTTCAGTAGAGAGTCTCTCAA
TAGATGGTTAGAAAAGCAGGAACAGGTAACAATAGGCCAG
```

Figure 22 - 2

```
CTCGCAGATTTTGATTTTGTGGATTTGCCAGCAGTTGATC
AGTACAGACACATGATTAAAGCACAACCCAAACAAAAGTT
GGACACTTCAATCCAAACGGAGTACCCGGCTTTGCAGACG
ATTGTGTACCATTCAAAAAAGATCAATGCAATATTCGGCC
CGTTGTTTAGTGAGCTTACTAGGCAATTACTGGACAGTGT
TGATTCGAGCAGATTTTTGTTTTTCACAAGAAAGACACCA
GCGCAGATTGAGGATTTCTTCGGAGATCTCGACAGTCATG
TGCCGATGGATGTCTTGGAGCTGGATATATCAAAATACGA
CAAATCTCAGAATGAATTCCACTGTGCAGTAGAATACGAG
ATCTGGCGAAGATTGGGTTTCGAAGACTTCTTGGGAGAAG
TTTGGAAACAAGGGCATAGAAAGACCACCCTCAAGGATTA
TACCGCAGGTATAAAAACTTGCATCTGGTATCAAAGAAAG
AGCGGGGACGTCACGACGTTCATTGGAAACACTGTGATCA
TTGCTGCATGTTTGGCCTCGATGCTTCCGATGGAGAAAAT
AATCAAAGGAGCCTTTTGCGGTGACGATAGTCTGCTGTAC
TTTCCAAAGGGTTGTGAGTTTCCGGATGTGCAACACTCCG
CGAATCTTATGTGGAATTTTGAAGCAAAACTGTTTAAAAA
ACAGTATGGATACTTTTGCGGAAGATATGTAATACATCAC
GACAGAGGATGCATTGTGTATTACGATCCCCTAAAGTTGA
TCTCGAAACTTGGTGCTAAACACATCAAGGATTGGGAACA
CTTGGAGGAGTTCAGAAGGTCTCTTTGTGATGTTGCTGTT
TCGTTGAACAATTGTGCGTATTACACACAGTTGGACGACG
CTGTATGGGAGGTTCATAAGACCGCCCCTCCAGGTTCGTT
TGTTTATAAAAGTCTGGTGAAGTATTTGTCTGATAAAGTT
CTTTTTAGAAGTTTGTTTATAGATGGCTCTAGTTGTTAAA
GGAAAAGTGAATATCAATGAGTTTATCGACCTGACAAAAA
TGGAGAAGATCTTACCGTCGATGTTTACCCCTGTAAAGAG
TGTTATGTGTTCCAAAGTTGATAAAATAATGGTTCATGAG
AATGAGTCATTGTCAGGGGTGAACCTTCTTAAAGGAGTTA
AGCTTATTGATAGTGGATACGTCTGTTTAGCCGGTTTGGT
CGTCACGGGCGAGTGGAACTTGCCTGACAATTGCAGAGGA
GGTGTGAGCGTGTGTCTGGTGGACAAAAGGATGGAAAGAG
CCGACGAGGCCACTCTCGGATCTTACTACACAGCAGCTGC
AAAGAAAAGATTTCAGTTCAAGGTCGTTCCCAATTATGCT
ATAACCACCCAGGACGCGATGAAAAACGTCTGGCAAGTTT
TAGTTAATATTAGAAATGTGAAGATGTCAGCGGGTTTCTG
TCCGCTTTCTCTGGAGTTTGTGTCGGTGTGTATTGTTTAT
AGAAATAATATAAAATTAGGTTTGAGAGAGAAGATTACAA
ACGTGAGAGACGGAGGGCCCATGGAACTTACAGAAGAAGT
CGTTGATGAGTTCATGGAAGATGTCCCTATGTCGATCAGG
CTTGCAAAGTTTCGATCTCGAACCGGAAAAAAGAGTGATG
TCCGCAAAGGGAAAAATAGTAGTAGTGATCGGTCAGTGCC
GAACAAGAACTATAGAAATGTTAAGGATTTGGAGGAATG
AGTTTTAAAAAGAATAATTTAATCGATGATGATTCGGAGG
CTACTGTCGCCGAATCGGATTCGTTTTAAATAGATCTTAC
AGTATCACTACTCCATCTCAGTTCGTGTTCTTGTCAttaa
TtaaATGGCTAGCAAAGGAGAAGAACTTTTCACTGGAGTT
GTCCCAATTCTTGTTGAATTAGATGGTGATGTTAATGGGC
ACAAATTTTCTGTCAGTGGAGAGGGTGAAGGTGATGCTAC
ATACGGAAAGCTTACCCTTAAATTTATTTGCACTACTGGA
```

Figure 22 - 3

```
AAACTACCTGTTCCATGGCCAACACTTGTCACTACTTTCT
CTTATGGTGTTCAATGCTTTTCCCGTTATCCGGATCATAT
GAAACGGCATGACTTTTTCAAGAGTGCCATGCCCGAAGGT
TATGTACAGGAACGCACTATATCTTTCAAAGATGACGGGA
ACTACAAGACGCGTGCTGAAGTCAAGTTTGAAGGTGATAC
CCTTGTTAATCGTATCGAGTTAAAAGGTATTGATTTTAAA
GAAGATGGAAACATTCTCGGACACAAACTCGAGTACAACT
ATAACTCACACAATGTATACATCACGGCAGACAAACAAAA
GAATGGAATCAAAGCTAACTTCAAAATTCGCCACAACATT
GAAGATGGATCCGTTCAACTAGCAGACCATTATCAACAAA
ATACTCCAATTGGCGATGGCCCTGTCCTTTTACCAGACAA
CCATTACCTGTCGACACAATCTGCCCTTTCGAAAGATCCC
AACGAAAAGCGTGACCACATGGGCCTTCTTGAGTTTGTAA
CTGCTGCTGGATTACACATGGCATGGATGAGCTCTACAA
ATAATGAggcggccgcACTCCGGCTACTTAGCTATTGTTG
TGAGATTTCCTAAAATAAAGTCACTGAAGACTTAAAATTC
AGGGTGGCTGATACCAAAATCAGCAGTGGTTGTTCGTCCA
CTTAAATATAACGATTGTCATATCTGGATCCAACAGTTAA
ACCATGTGATGGTGTATACTGTGGTATGGCGTAAAACAAC
GGAAAAGTCGCTGAAGACTTAAAATTCAGGGTGGCTGATA
CCAAAATCAGCAGTGGTTGTTCGTCCACTTAAAAATAACG
ATTGTCATATCTGGATCCAACAGTTAAACCATGTGATGGT
GTATACTGTGGTATGGCGTAAACAACGGAGAGGTTCGAAT
CCTCCCCTAACCGCGGGTAGCGGCCCAggtacccggAtgt
gtttccggctgatgagtccgtgaggacgaaaccCTGCA
GGCATGCAAGCTTGGCGTAATcatggtcatAGCctagcta
gagtccgcaaatcaccagtctctctctacaaatctatctc
tctctatttctccagaataatgtgtgagtagttcccaga
taagggaattagggttcttataggggtttcgctcatgtgtt
gagcatataagaaacccttagtatgtatttgtatttgtaa
aatacttcatcaataaaatttctaattctaaaaccaaa
atccagtgacctgcagcCCGGccggggggatccactagcAG
ATTGTCGTTTCCCGCCTTCAGTTTAAACTATCAGTGTTTG
ACAGGATATATTGGCGGGTAAACCTAAGAGAAAAGAGCGT
TTATTAGAATAATCGGATATTTAAAAGGGCGTGAAAAGGT
TTATCCGTTCGTCCATTTGTATGTGCATGCCAACCACAGG
AGATCTCAgtaaagcgctggctgaaccccagccggaact
gaccccacaaggccctagcgttgcaatgcaccaggtcat
cattgaccaggcgtgttccaccaggccgctgcctcgcaa
ctcttcgcaggcttgccgacctgctcgcgccacttcttc
acgcgggtggaatccgatccgacatgaggcggaaggttt
ccagcttgagcgggtacggctccggtgcgagctgaaata
gtcgaacatccgtcgggccgtcggcgacagcttgcggtac
ttctcccatatgaatttcgtgtagtggtcgccagcaaaca
gcacgacgattcctcgtcgatcaggacctggcaacggga
cgtttcttgccacggtccaggacgcggaagcggtgcagc
agcgacaccgattccggtgcccaacgcggtcggacgtga
agcccatcgccgtcgcctgtaggagcgacaggcattcctc
ggccttcgtgtaataccggccattgatgaccagcccagg
tcctggcaaagctcgtagaacgtgaaggtgatcggctcgc
```

Figure 22 - 4 cgataggggtgcgcttcgcgtactccaacacctgctgcca
caccagttcgtcatcgtcggcccgcagctcgacgccggtg
taggtgatcttcacgtccttgttgacgtggaaaatgacct
tgttttgcagcgcctcgcgcgggattttcttgttgcgcgt
ggtgaacagggcagagcgggccgtgtcgtttggcatcgct
cgcatcgtgtccggccacggcgcaatatcgaacaaggaaa
gctgcatttccttgatctgctgcttcgtgtgtttcagcaa
cgcggcctgcttggcctcgctgacctgttttgccaggtcc
tcgccggcggttttttcgcttcttggtcgtcatagttcctc
gcgtgtcgatggtcatcgacttcgccaaacctgccgcctc
ctgttcgagacgacgcgaacgctccacggcggccgatggc
gcgggcaggcaggggaagccagttgcacgctgtcgcgct
cgatcttggccgtagcttgctggaccatcgagccgacgga
ctggaaggtttcgcgggcgcacgcatgacggtgcggctt
gcgatggtttcggcatcctcggcggaaaacccgcgtcga
tcagttcttgcctgtatgccttccggtcaaacgtccgatt
cattcacctcttgcgggattgcccgactcacgccggg
gcaatgtgcccttattcctgatttgacccgcctggtgcct
tggtgtccagataatccaccttatcggcaatgaagtcggt
cccgtagaccgtctggccgtccttctcgtacttggtattc
cgaatcttgccctgcacgaataccagcgaccccttgccca
aatacttgccgtgggcctcggcctgagagccaaaacactt
gatgcggaagaagtcggtgcgctcctgcttgtcgccggca
tcgttgcgccacatctaggtactaaaacaattcatccagt
aaaatataatatttattttctcccaatcaggcttgatcc
ccagtaagtcaaaaatagctcgacatactgttcttcccc
gatatcctccctgatcgaccggacgcagaaggcaatgtca
taccacttgtccgccctgccgcttctcccaagatcaataa
agccacttactttgccatctttcacaaagatgttgctgtc
tcccaggtcgccgtgggaaaagacaagttcctcttcgggc
ttttccgtctttaaaaaatcatacagctcgcgcggatctt
taaatggagtgtcttcttcccagttttgcaatccacatc
ggccagatcgttattcagtaagtaatccaattcggctaag
cggctgtctaagctattcgtatagggacaatccgatatgt
cgatggagtgaagagcctgatgcactccgcatacagctc
gataatctttcagggctttgttcatcttcatactcttcc
gagcaaaggacgccatcggcctcactcatgagcagattgc
tccagccatcatgccgttcaaagtgcaggacctttggaac
aggcagcttccttccagccatagcatcatgtccttttcc
cgttccacatcataggtggtccctttataccggctgtccg
tcattttaaatataggtttcatttctcccaccagctt
atataccttagcaggagacattccttccgtatctttacg
cagcggtattttcgatcagttttttcaattccggtgata
ttctcatttagccatttattattccttcctctttctcta
cagtatttaaagatacccaagaagctaattataacaaga
cgaactccaattcactgttccttgcattctaaaaaccttaa
ataccagaaaacagcttttcaaagttgttttcaaagttg
gcgtataacatagtatcgacggagccgattttgaaaccac
aattatgggtgatgctgccaactcgagagcgggccgggag
ggttcgagaagggggggcaccccccttcggcgtgcgcggt

Figure 22 - 5

```
cacgcgcacagggcgcagccctggttaaaaacaaggttta
taaatattggtttaaaagcaaggtaaaagacaggttagcg
gtggccgaaaaacgggcggaaaaccttgcaaatgctggat
tttctgcctgtggacagcccctcaaatgtcaataggtgcg
cccctcatctgtcagcactctgcccctcaagtgtcaagga
tcgcgccctcatctgtcagtagtcgcgccctcaagtgt
caataccgcagggcacttatccccaggcttgtccacatca
tctgtgggaaactgcgtaaaatcaggcgttttgccgat
ttgcgaggctggccagctccacgtcgccggccgaaatcga
gcctgccctcatctgtcaacgccgcgccgggtgagtcgg
cccctcaagtgtcaacgtcgcccctcatctgtcagtgag
ggccaagttttccgcgaggtatccacaacgccggcggccg
gccgcggtgtctcgcacacggcttcgacggcgtttctggc
gcgtttgcagggccatagacggccgccagcccagcggcga
gggcaaccagcccggtgagctCTAGTGGACTGATGGGCTG
CCTGTATCGAGTGGTGATTTTGTGCCGAGCTGCCGGTCGG
GGAGCTGTTGGCTGGCTGGTGGCAGGATATATTGTGGTGT
AAACAAATTGACGCTTAGACAACTTAATAACACATTGCGG
ACGTTTTTAATGTACTGgggtggttttggtaccgggccc
ccctcgaggtcgacggtatcgataagcttgatatcgaatt
cctgcaggtcaacatggtggagcacGACACTCTCGTCTAC
TCCAAGAATATCAAAGATACAGTCTCAGAAGACCAAAGGG
CTATTGAGACTTTTCAACAAAGGGTAATATCGGGAAACCT
CCTCGGATTCCATTGCCCAGCTATCTGTCACTTCATCAAA
AGGACAGTAGAAAAGGAAGGTGGCACCTACAAATGCCATC
ATTGCGATAAAGGAAAGGCTATCGTTCAAGATGCCTCTGC
CGACAGTGGTCCCAAAGATGGACCCCACCCACGAGGAGC
ATCGTGGAAAAGAAGACGTTCCAACCACGTCTTCAAAGC
AAGTGGATTGATGTGATAACATGGTGGAGCACGACACTCT
CGTCTACTCCAAGAATATCAAAGATACAGTCTCAGAAGAC
CAAAGGGCTATTGAGACTTTTCAACAAAGGGTAATATCGG
GAAACCTCCTCGGATTCCATTGCCCAGCTATCTGTCACTT
CATCAAAAGGACAGTAGAAAAGGAAGGTGGCACCTACAAA
TGCCATCATTGCGATAAAGGAAAGGCTATCGTTCAAGATG
CCTCTGCCGACAGTGGTCCCAAAGATGGACCCCACCCAC
GAGGAGCATCGTGGAAAAGAAGACGTTCCAACCACGTCT
TCAAAGCAAGTGGATTGATGTGATATCTCCACTGACGTAA
GGGATGACGCACAATCCCACTATCCTTCGCAAGACCTTCC
TCTATATAAGGAAGTTCATTTCATTTGGAGAGG
```

Figure 22 - 6

SEQUENCE LISTING

```
<160> NUMBER OF SEQ ID NOS: 20

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gtatttttac aacaattacc aac                                              23

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gggcctaggc tatgaccatg attacgc                                          27
```

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
taacggccta gggcggccgc                                                    20

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tcgagcggcc gccctaggcc gttaat                                             26

<210> SEQ ID NO 5
<211> LENGTH: 11578
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 5
gtatttttac aacaattacc aacaacaaca acaacagac aacattacaa ttactattta         60
caattacaat ggcatacaca cagacagcta ccacatcagc tttgctggac actgtccgag       120
gaaacaactc cttggtcaat gatctagcaa agcgtcgtct ttacgacaca gcggttgaag       180
agtttaacgc tcgtgaccgc aggcccaagg tgaactttt aaaagtaata agcgaggagc        240
agacgcttat tgctacccgg gcgtatccag aattccaaat tacatttat aacacgcaaa        300 atgccgtgca ttcgcttgca ggtggattgc gatctttaga actggaatat ctgatgatgc       360
aaattcccta cggatcattg acttatgaca taggcgggaa ttttgcatcg catctgttca       420
agggacgagc atatgtacac tgctgcatgc ccaacctgga cgttcgagac atcatgcggc       480
acgaaggcca gaaagacagt attgaactat acctttctag gctagagaga gggggaaaaa       540
cagtccccaa cttccaaaag gaagcatttg acagatacgc agaaattcct gaagacgctg       600
tctgtcacaa tactttccag acatgcgaac atcagccgat gcagcaatca ggcagagtgt       660
atgccattgc gctacacagc atatatgaca taccagccga tgagttcggg gcggcactct       720
tgaggaaaaa tgtccatacg tgctatgccg ctttccactt ctccgagaac ctgcttcttg       780
aagattcatg cgtcaatttg gacgaaatca acgcgtgttt tcgcgcgat ggagacaagt        840 tgacctttc tttttgcatca gagagtactc ttaattactg tcatagttat tctaatattc       900
ttaagtatgt gtgcaaaact tacttcccgg cctctaatag agaggtttac atgaaggagt       960
ttttagtcac cagagttaat acctggtttt gtaagtttc tagaatagat acttttcttt      1020
tgtacaaagg tgtggcccat aaaagtgtag atagtgagca gttttatact gcaatggaag      1080
acgcatggca ttacaaaaag actcttgcaa tgtgcaacag cgagagaatc ctccttgagg      1140
attcatcatc agtcaattac tggtttccca aaatgaggga tatggtcatc gtaccattat      1200
tcgacatttc tttggagact agtaagagga cgcgcaagga agtcttagtg tccaaggatt      1260

-continued

```
tcgtgtttac agtgcttaac cacattcgaa cataccaggc gaaagctctt acatacgcaa      1320
atgttttgtc cttcgtcgaa tcgattcgat cgagggtaat cattaacggt gtgacagcga      1380
ggtccgaatg ggatgtggac aaatctttgt tacaatcctt gtccatgacg tttttacctgc     1440 atactaagct tgccgttcta aaggatgact tactgattag caagtttagt ctcggttcga      1500
aaacggtgtg ccagcatgtg tgggatgaga tttcgctggc gtttgggaac gcatttccct     1560
ccgtgaaaga gaggctcttg aacaggaaac ttatcagagt ggcaggcgac gcattagaga     1620
tcagggtgcc tgatctatat gtgaccttcc acgacagatt agtgactgag tacaaggcct     1680
ctgtggacat gcctgcgctt gacattagga agaagatgga agaaacggaa gtgatgtaca     1740
atgcactttc agaattatcg gtgttaaggg agtctgacaa attcgatgtt gatgtttttt     1800
cccagatgtg ccaatctttg gaagttgacc caatgacggc agcgaaggtt atagtcgcgg     1860
tcatgagcaa tgagagcggt ctgactctca catttgaacg acctactgag gcgaatgttg     1920
cgctagcttt acaggatcaa gagaaggctt cagaaggtgc attggtagtt acctcaagag     1980
aagttgaaga accgtccatg aagggttcga tggccagagg agagttacaa ttagctggtc     2040
ttgctggaga tcatccggaa tcgtcctatt ctaagaacga ggagatagag tctttagagc     2100
agtttcatat ggcgacggca gattcgttaa ttcgtaagca gatgagctcg attgtgtaca     2160
cgggtccgat taaagttcag caaatgaaaa actttatcga tagcctggta gcatcactat     2220
ctgctgcggt gtcgaatctc gtcaagatcc tcaaagatac agctgctatt gaccttgaaa     2280
cccgtcaaaa gtttggagtc ttggatgttg catctaggaa gtggttaatc aaaccaacgg     2340
ccaagagtca tgcatggggt gttgttgaaa cccacgcgag gaagtatcat gtggcgcttt     2400
tggaatatga tgagcagggt gtggtgacat gcgatgattg gagaagagta gctgttagct     2460
ctgagtctgt tgtttattcc gacatggcga aactcagaac tctgcgcaga ctgcttcgaa     2520
acggagaacc gcatgtcagt agcgcaaagg ttgttcttgt ggacggagtt ccgggctgtg     2580
gaaaaaccaa agaaattctt tccagggtta attttgatga agatctaatt ttagtacctg     2640
ggaagcaagc cgcggaaatg atcagaagac gtgcgaattc ctcagggatt attgtggcca     2700
cgaaggacaa cgttaaaacc gttgattctt tcatgatgaa ttttgggaaa agcacacgct     2760
gtcagttcaa gaggttattc attgatgaag ggttgatgtt gcatactggt tgtgttaatt     2820
ttcttgtggc gatgtcattg tgcgaaattg catatgttta cggagacaca cagcagattc     2880
catacatcaa tagagtttca ggattcccgt accccgccca ttttgccaaa ttggaagttg     2940
acgaggtgga gacacgcaga actactctcc gttgtccagc cgatgtcaca cattatctga     3000
acaggagata tgagggcttt gtcatgagca cttcttcggt taaaaagtct gtttcgcagg     3060
agatggtcgg cggagccgcc gtgatcaatc cgatctcaaa acccttgcat ggcaagatct     3120 tgactttac ccaatcggat aaagaagctc tgctttcaag agggtattca gatgttcaca     3180
ctgtgcatga agtgcaaggc gagacatact ctgatgtttc actagttagg ttaaccccta     3240
caccggtctc catcattgca ggagacagcc cacatgtttt ggtcgcattg tcaaggcaca     3300
cctgttcgct caagtactac actgttgtta tggatccttt agttagtatc attagagatc     3360
tagagaaact tagctcgtac ttgttagata tgtataaggt cgatgcagga acacaatagc     3420
aattacagat tgactcggtg ttcaaaggtt ccaatctttt tgttgcagcg ccaaagactg     3480
gtgatatttc tgatatgcag ttttactatg ataagtgtct cccaggcaac agcaccatga     3540
tgaataattt tgatgctgtt accatgaggt tgactgacat tcattgaat gtcaaagatt      3600 gcatattgga tatgtctaag tctgttgctg cgcctaagga tcaaatcaaa ccactaatac     3660
```

```
ctatggtacg aacggcggca gaaatgccac gccagactgg actattggaa aatttagtgg    3720
cgatgattaa aagaaacttt aacgcacccg agttgtctgg catcattgat attgaaaata    3780
ctgcatcttt ggttgtagat aagttttttg atagttattt gcttaaagaa aaagaaaaac    3840
caaataaaaa tgtttctttg ttcagtagag agtctctcaa tagatggtta gaaaagcagg    3900
aacaggtaac aataggccag ctcgcagatt ttgattttgt ggatttgcca gcagttgatc    3960
agtacagaca catgattaaa gcacaaccca aacaaaagtt ggacacttca atccaaacgg    4020
agtacccggc tttgcagacg attgtgtacc attcaaaaaa gatcaatgca atattcggcc    4080
cgttgtttag tgagcttact aggcaattac tggacagtgt tgattcgagc agattttgt     4140 ttttcacaag aaagacacca gcgcagattg aggatttctt cggagatctc gacagtcatg    4200
tgccgatgga tgtcttggag ctggatatat caaatacga caaatctcag aatgaattcc     4260
actgtgcagt agaatacgag atctggcgaa gattgggttt cgaagacttc ttgggagaag    4320
tttggaaaca agggcataga aagaccaccc tcaaggatta taccgcaggt ataaaaactt    4380
gcatctggta tcaaagaaag agcggggacg tcacgacgtt cattggaaac actgtgatca    4440
ttgctgcatg tttggcctcg atgcttccga tggagaaaat aatcaaagga gccttttgcg    4500
gtgacgatag tctgctgtac tttccaaagg gttgtgagtt tccggatgtg caacactccg    4560
cgaatcttat gtggaatttt gaagcaaaac tgtttaaaaa acagtatgga acttttgcg     4620 gaagatatgt aatacatcac gacagaggat gcattgtgta ttacgatccc ctaaagttga    4680
tctcgaaact tggtgctaaa cacatcaagg attgggaaca cttggaggag ttcagaaggt    4740
ctctttgtga tgttgctgtt tcgttgaaca attgtgcgta ttacacacag ttggacgacg    4800
ctgtatggga ggttcataag accgcccctc caggttcgtt tgtttataaa agtctggtga    4860
agtatttgtc tgataaagtt cttttttagaa gtttgtttat agatggctct agttgttaaa    4920
ggaaaagtga atatcaatga gtttatcgac ctgacaaaaa tggagaagat cttaccgtcg    4980
atgtttaccc ctgtaaagag tgttatgtgt tccaaagttg ataaaataat ggttcatgag    5040
aatgagtcat tgtcagggt gaaccttctt aaaggagtta agcttattga tagtggatac    5100
gtctgtttag ccggtttggt cgtcacgggc gagtggaact tgcctgacaa ttgcagagga    5160
ggtgtgagcg tgtgtctggt ggacaaaagg atggaaagag ccgacgaggc cactctcgga    5220
tcttactaca cagcagctgc aaagaaaaga tttcagttca aggtcgttcc caattatgct    5280
ataaccaccc aggacgcgat gaaaaacgtc tggcaagttt tagttaatat tagaaatgtg    5340
aagatgtcag cgggttctg tccgctttct ctggagtttg tgtcggtgtg tattgttat      5400 agaaataata taaaattagg tttgagagag aagattacaa acgtgagaga cggagggccc    5460
atggaactta cagaagaagt cgttgatgag ttcatggaag atgtccctat gtcgatcagg    5520
cttgcaaagt ttcgatctcg aaccggaaaa aagagtgatg tccgcaaagg gaaaaatagt    5580
agtagtgatc ggtcagtgcc gaacaagaac tatagaaatg ttaaggatt tggaggaatg      5640 agttttaaaa agaataattt aatcgatgat gattcggagg ctactgtcgc cgaatcggat    5700 tcgtttaaa tagatcttac agtatcacta ctccatctca gttcgtgttc ttgtcattaa      5760
ttaacggcct agggcggccg ctcgagggt agtcaagatc ataataaat aacgattgt        5820 gtccgtaatc acacgtggtg cgtacgataa cgcatagtgt ttttccctcc acttaaatcg    5880
aagggttgtg tcttggatcg cgcgggtcaa atgtatatgg ttcatataca tccgcaggca    5940
cgtaataaag cgaggggttc gggtcgaggt cggctgtgaa actcgaaaag gttccggaaa    6000
```

```
acaaaaaaga gagtggtagg taatagtgtt aataataaga aaataaataa tagtggtaag    6060
aaaggtttga aagttgagga aattgaggat aatgtaagtg atgacgagtc tatcgcgtca    6120
tcgagtacgt tttaatcaat atgccttata caatcaactc tccgagccaa tttgtttact    6180
taagttccgc ttatgcagat cctgtgcagc tgatcaatct gtgtacaaat gcattgggta    6240
accagtttca aacgcaacaa gctaggacaa cagtccaaca gcaatttgcg gatgcctgga    6300
aacctgtgcc tagtatgaca gtgagatttc ctgcatcgga tttctatgtg tatagatata    6360
attcgacgct tgatccgttg atcacggcgt tattaaatag cttcgatact agaaatagaa    6420
taatagaggt tgataatcaa cccgcaccga atactactga aatcgttaac gcgactcaga    6480
gggtagacga tgcgactgta gctataaggg cttcaatcaa taatttggct aatgaactgg    6540
ttcgtggaac tggcatgttc aatcaagcaa gctttgagac tgctagtgga cttgtctgga    6600
ccacaactcc ggctacttag ctattgttgt gagatttcct aaaataaagt cactgaagac    6660
ttaaaattca gggtggctga taccaaaatc agcagtggtt gttcgtccac ttaaatataa    6720
cgattgtcat atctggatcc aacagttaaa ccatgtgatg gtgtatactg tggtatggcg    6780
taaaacaacg gaaagtcgc tgaagactta aaattcaggg tggctgatac caaaatcagc    6840
agtggttgtt cgtccactta aaaataacga ttgtcatatc tggatccaac agttaaacca    6900
tgtgatggtg tatactgtgg tatgcgtaa acaacggaga ggttcgaatc ctcccctaac    6960
cgcgggtagc ggcccaggta cccgatgtg ttttccgggc tgatgagtcc gtgaggacga    7020
aaccctgcag gcatgcaagc ttggcgtaat catggtcata gcctagagtc cgcaaatcac    7080
cagtctctct ctacaaatct atctctctct attttctcca gaataatgtg tgagtagttc    7140
ccagataagg gaattagggt tcttataggg tttcgctcat gtgttgagca tataagaaac    7200
ccttagtatg tatttgtatt tgtaaaatac ttctatcaat aaaatttcta attcctaaaa    7260
ccaaaatcca gtgacctgca gcccggccgg gggatccact agcagattgt cgtttcccgc    7320
cttcagttta aactatcagt gtttgacagg atatattggc gggtaaacct aagagaaaag    7380
agcgtttatt agaataatcg gatatttaaa agggcgtgaa aaggtttatc cgttcgtcca    7440
tttgtatgtg catgccaacc acaggagatc tcagtaaagc gctggctgaa ccccagccg    7500
gaactgaccc cacaaggccc tagcgtttgc aatgcaccag gtcatcattg acccaggcgt    7560
gttccaccag gccgctgcct cgcaactctt cgcaggcttc gccgacctgc tcgcgccact    7620
tcttcacgcg ggtggaatcc gatccgcaca tgaggcggaa ggtttccagc ttgagcgggt    7680
acggctcccg gtgcgagctg aaatagtcga acatccgtcg ggccgtcggc gacagcttgc    7740
ggtacttctc ccatatgaat tcgtgtagt ggtcgccagc aaacagcacg acgatttcct    7800
cgtcgatcag gacctggcaa cgggacgttt tcttgccacg gtccaggacg cggaagcggt    7860
gcagcagcga caccgattcc aggtgcccaa cgcggtcgga cgtgaagccc atcgccgtcg    7920
cctgtaggcg cgacaggcat tcctcggcct tcgtgtaata ccggccattg atcgaccagc    7980
ccaggtcctg gcaaagctcg tagaacgtga aggtgatcgg ctcgccgata ggggtgcgct    8040
tcgcgtactc caacacctgc tgccacacca gttcgtcatc gtcggcccgc agctcgacgc    8100
cggtgtaggt gatcttcacg tccttgttga cgtggaaaat gaccttgttt tgcagcgcct    8160
cgcgcgggat tttcttgttg cgcgtggtga acagggcaga gcgggccgtg tcgtttggca    8220
tcgctcgcat cgtgtccggc cacggcgcaa tatcgaacaa ggaaagctgc atttccttga    8280
tctgctgctt cgtgtgtttc agcaacgcgg cctgcttggc ctcgctgacc tgttttgcca    8340
ggtcctcgcc ggcggttttt cgcttcttgg tcgtcatagt tcctcgcgtg tcgatggtca    8400
```

```
tcgacttcgc caaacctgcc gcctcctgtt cgagacgacg cgaacgctcc acggcggccg   8460
atggcgcggg cagggcaggg ggagccagtt gcacgctgtc gcgctcgatc ttggccgtag   8520
cttgctggac catcgagccg acggactgga aggtttcgcg gggcgcacgc atgacggtgc   8580
ggcttgcgat ggtttcggca tcctcggcgg aaaaccccgc gtcgatcagt tcttgcctgt   8640
atgccttccg gtcaaacgtc cgattcattc accctccttg cgggattgcc ccgactcacg   8700
ccggggcaat gtgcccttat tcctgatttg acccgcctgg tgccttggtg tccagataat   8760
ccaccttatc ggcaatgaag tcggtcccgt agaccgtctg gccgtccttc tcgtacttgg   8820
tattccgaat cttgccctgc acgaatacca gcgaccccct gcccaaatac ttgccgtggg   8880
cctcggcctg agagccaaaa cacttgatgc ggaagaagtc ggtgcgctcc tgcttgtcgc   8940
cggcatcgtt gcgccacatc taggtactaa acaattcat ccagtaaaat ataaatttt    9000 attttctccc aatcaggctt gatcccagt aagtcaaaaa atagctcgac atactgttct    9060
tccccgatat cctccctgat cgaccggacg cagaaggcaa tgtcatacca cttgtccgcc   9120
ctgccgcttc tcccaagatc aataaagcca cttactttgc catctttcac aaagatgttg   9180
ctgtctccca ggtcgccgtg ggaaaagaca agttcctctt cgggcttttc cgtctttaaa   9240
aaatcataca gctcgcgcgg atctttaaat ggagtgtctt cttcccagtt ttcgcaatcc   9300
acatcggcca gatcgttatt cagtaagtaa tccaattcgg ctaagcggct gtctaagcta   9360
ttcgtatagg gacaatccga tatgtcgatg gagtgaaaga gcctgatgca ctccgcatac   9420
agctcgataa tcttttcagg gctttgttca tcttcatact cttccgagca aaggacgcca   9480
tcggcctcac tcatgagcag attgctccag ccatcatgcc gttcaaagtg caggaccttt   9540
ggaacaggca gctttccttc cagccatagc atcatgtcct tttcccgttc cacatcatag   9600
gtggtccctt tataccggct gtccgtcatt tttaaatata ggttttcatt ttctcccacc   9660
agcttatata ccttagcagg agacattcct tccgtatctt ttacgcagcg gtattttttcg  9720 atcagttttt tcaattccgg tgatattctc attttagcca tttattattt ccttcctctt   9780
ttctacagta tttaaagata ccccaagaag ctaattataa caagacgaac tccaattcac   9840
tgttccttgc attctaaaac cttaaatacc agaaaacagc ttttttcaaag ttgtttttcaa 9900 agttggcgta taacatagta tcgacggagc cgattttgaa accacaatta tgggtgatgc   9960
tgccaactcg agagcgggcc gggagggttc gagaaggggg ggcaccccccc ttcggcgtgc  10020 gcggtcacgc gcacagggcg cagccctggt taaaaacaag gtttataaat attggtttaa  10080
aagcaggtta aaagacaggt tagcggtggc cgaaaaacgg gcggaaaccc ttgcaaatgc  10140
tggattttct gcctgtggac agcccctcaa atgtcaatag gtgcgcccct catctgtcag  10200
cactctgccc ctcaagtgtc aaggatcgcg cccctcatct gtcagtagtc gcgcccctca  10260
agtgtcaata ccgcagggca cttatcccca ggcttgtcca catcatctgt gggaaactcg  10320
cgtaaaatca ggcgttttcg ccgatttgcg aggctgccagctccacgtc gccggccgaa    10380 atcgagcctg cccctcatct gtcaacgccg cgccgggtga gtcggcccct caagtgtcaa  10440
cgtccgcccc tcatctgtca gtgagggcca agttttccgc gaggtatcca acgccggc     10500 ggccggccgc ggtgtctcgc acacggcttc gacggcgttt ctggcgcgtt tgcagggcca  10560
tagacggccg ccagcccagc ggcgagggca accagcccgg tgagctctag tggactgatg  10620
ggctgcctgt atcgagtggt gattttgtgc cgagctgccg gtcggggagc tgttggctgg  10680
ctggtggcag gatatattgt ggtgtaaaca aattgacgct tagacaactt aataacacat  10740
```

```
tgcggacgtt tttaatgtac tggggtggtt ttggtaccgg gccccccctc gaggtcgacg    10800
gtatcgataa gcttgatatc gaattcctgc aggtcaacat ggtggagcac gacactctcg    10860
tctactccaa gaatatcaaa gatacagtct cagaagacca aagggctatt gagactttc     10920 aacaaagggt aatatcggga aacctcctcg gattccattg cccagctatc tgtcacttca    10980 tcaaaggac agtagaaaag aaggtggca cctacaaatg ccatcattgc gataaaggaa      11040
aggctatcgt tcaagatgcc tctgccgaca gtggtcccaa agatggaccc ccacccacga    11100
ggagcatcgt ggaaaaagaa gacgttccaa ccacgtcttc aaagcaagtg gattgatgtg    11160
ataacatggt ggagcacgac actctcgtct actccaagaa tatcaaagat acagtctcag    11220
aagaccaaag ggctattgag acttttcaac aaagggtaat atcgggaaac ctcctcggat    11280
tccattgccc agctatctgt cacttcatca aaggacagt agaaaaggaa ggtggcacct     11340
acaaatgcca tcattgcgat aaaggaaagg ctatcgttca agatgcctct gccgacagtg    11400
gtcccaaaga tggacccca cccacgagga gcatcgtgga aaaagaagac gttccaacca     11460
cgtcttcaaa gcaagtggat tgatgtgata tctccactga cgtaagggat gacgcacaat    11520
cccactatcc ttcgcaagac cttcctctat ataaggaagt tcatttcatt tggagagg     11578

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Lys Pro Ile Pro Asn Pro Leu Leu Gly Leu Asp
  1               5                  10

<210> SEQ ID NO 7
<211> LENGTH: 118
<212> TYPE: DNA
<213> ORGANISM: Artificial Sequence
<220> FEATURE:
<223> OTHER INFORMATION: Description of Artificial Sequence: Synthetic
      DNA cassette

<400> SEQUENCE: 7
cgaggccaga agagcaacct ttacgtactt gctcttcagc ttgaaggtaa gcctatccct    60
aaccctctcc tcggtctcga ttctacgcgt accggtcatc atcaccatca ccattgac     118

<210> SEQ ID NO 8
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
atcgaggcca gaagagcaac ctttacgtac ttgctcttca gcttctc                  47

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 9
cccttaatta acatggaacg agctatacaa ggaaac                                    36

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ccctactagt cttactcgcc ttcttttcg aa                                         32

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggcctaaaat ggctagcaaa ggagaag                                              27

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcttatttgt agagctcatc cat                                                  23

<210> SEQ ID NO 13
<211> LENGTH: 10606
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 13
gtatttttac aacaattacc aacaacaaca acaacagac aacattacaa ttactattta           60
caattacaat ggcatacaca cagacagcta ccacatcagc tttgctggac actgtccgag         120
gaaacaactc cttggtcaat gatctagcaa agcgtcgtct ttacgacaca gcggttgaag         180
agtttaacgc tcgtgaccgc aggcccaagg tgaactttc aaaagtaata agcgaggagc          240
agacgcttat tgctacccgg gcgtatccag aattccaaat tacattttat aacacgcaaa         300
atgccgtgca ttcgcttgca ggtggattgc gatctttaga actggaatat ctgatgatgc         360
aaattcccta cggatcattg acttatgaca taggcgggaa ttttgcatcg catctgttca         420
agggacgagc atatgtacac tgctgcatgc ccaacctgga cgttcgagac atcatgcggc         480
acgaaggcca gaaagacagt attgaactat acctttctag gctagagaga ggggggaaaa         540
cagtccccaa cttccaaaag gaagcatttg acagatacgc agaaattcct gaagacgctg         600
tctgtcacaa tactttccag acatgcgaac atcagccgat gcagcaatca ggcagagtgt         660
atgccattgc gctacacagc atatatgaca taccagccga tgagttcggg gcggcactct         720
tgaggaaaaa tgtccatacg tgctatgccg ctttccactt ctccgagaac ctgcttcttg         780
```

-continued

```
aagattcatg cgtcaatttg gacgaaatca acgcgtgttt ttcgcgcgat ggagacaagt     840
tgacctttc tttgcatca gagagtactc ttaattactg tcatagttat tctaatattc       900
ttaagtatgt gtgcaaaact tacttcccgg cctctaatag agaggtttac atgaaggagt     960
ttttagtcac cagagttaat acctggtttt gtaagttttc tagaatagat acttttcttt    1020
tgtacaaagg tgtggcccat aaaagtgtag atagtgagca gttttatact gcaatggaag    1080
acgcatggca ttacaaaaag actcttgcaa tgtgcaacag cgagagaatc ctccttgagg    1140
attcatcatc agtcaattac tggtttccca aaatgaggga tatggtcatc gtaccattat    1200
tcgacatttc tttggagact agtaagagga cgcgcaagga agtcttagtg tccaaggatt    1260
tcgtgtttac agtgcttaac cacattcgaa cataccaggc gaaagctctt acatacgcaa    1320
atgttttgtc cttcgtcgaa tcgattcgat cgagggtaat cattaacggt gtgacagcga    1380
ggtccgaatg ggatgtggac aaatctttgt tacaatcctt gtccatgacg tttttacctgc   1440
atactaagct tgccgttcta aaggatgact tactgattag caagtttagt ctcggttcga    1500
aaacggtgtg ccagcatgtg tgggatgaga tttcgctggc gtttgggaac gcatttccct    1560
ccgtgaaaga gaggctcttg aacaggaaac ttatcagagt ggcaggcgac gcattagaga    1620
tcagggtgcc tgatctatat gtgaccttcc acgacagatt agtgactgag tacaaggcct    1680
ctgtggacat gcctgcgctt gacattagga agaagatggaa agaaacggaa gtgatgtaca   1740
atgcactttc agaattatcg gtgttaaggg agtctgacaa attcgatgtt gatgtttttt    1800
cccagatgtg ccaatctttg gaagttgacc caatgacggc agcgaaggtt atagtcgcgg    1860
tcatgagcaa tgagagcggt ctgactctca catttgaacg acctactgag gcgaatgttg    1920
cgctagcttt acaggatcaa gagaaggctt cagaaggtgc attggtagtt acctcaagag    1980
aagttgaaga accgtccatg aagggttcga tggccagagg agagttacaa ttagctggtc    2040
ttgctggaga tcatccggaa tcgtcctatt ctaagaacga ggagatagag tctttagagc    2100
agtttcatat ggcgacggca gattcgttaa ttcgtaagca gatgagctcg attgtgtaca    2160
cgggtccgat taaagttcag caaatgaaaa actttatcga tagcctggta gcatcactat    2220
ctgctgcggt gtcgaatctc gtcaagatcc tcaaagatac agctgctatt gaccttgaaa    2280
cccgtcaaaa gtttggagtc ttggatgttg catctaggaa gtggttaatc aaaccaacgg    2340
ccaagagtca tgcatggggt gttgttgaaa cccacgcgag gaagtatcat gtggcgcttt    2400
tggaatatga tgagcagggt gtggtgacat gcgatgattg gagaagagta gctgttagct    2460
ctgagtctgt tgtttattcc gacatggcga aactcagaac tctgcgcaga ctgcttcgaa    2520
acggagaacc gcatgtcagt agcgcaaagg ttgttcttgt ggacggagtt ccgggctgtg    2580
gaaaaaccaa agaattcctt tccagggtta attttgatga agatctaatt ttagtacctg    2640
ggaagcaagc cgcggaaatg atcagaagac gtgcgaattc ctcagggatt attgtggcca    2700
cgaaggacaa cgttaaaacc gttgattctt tcatgatgaa ttttgggaaa agcacacgct    2760
gtcagttcaa gaggttattc attgatgaag ggttgatgtt gcatactggt tgtgttaatt    2820
ttcttgtggc gatgtcattg tgcgaaattg catatgttta cggagacaca cagcagattc    2880
catacatcaa tagagtttca ggattcccgt acccgccca ttttgccaaa ttggaagttg     2940
acgaggtgga gacacgcaga actactctcc gttgtccagc cgatgtcaca cattatctga   3000
acaggagata tgagggcttt gtcatgagca cttcttcggt taaaaagtct gtttcgcagg    3060
agatggtcgg cggagccgcc gtgatcaatc cgatctcaaa acccttgcat ggcaagatct    3120
```

-continued

```
tgacttttac ccaatcggat aaagaagctc tgctttcaag agggtattca gatgttcaca    3180
ctgtgcatga agtgcaaggc gagacatact ctgatgtttc actagttagg ttaacccta     3240 caccggtctc catcattgca ggagacagcc cacatgtttt ggtcgcattg tcaaggcaca    3300
cctgttcgct caagtactac actgttgtta tggatccttt agttagtatc attagagatc    3360
tagagaaact tagctcgtac ttgttagata tgtataaggt cgatgcagga acacaatagc    3420
aattacagat tgactcggtg ttcaaaggtt ccaatctttt tgttgcagcg ccaaagactg    3480
gtgatatttc tgatatgcag ttttactatg ataagtgtct cccaggcaac agcaccatga    3540
tgaataattt tgatgctgtt accatgaggt tgactgacat tcattgaat gtcaaagatt      3600 gcatattgga tatgtctaag tctgttgctg cgcctaagga tcaaatcaaa ccactaatac    3660
ctatggtacg aacggcggca gaaatgccac gccagactgg actattggaa aatttagtgg    3720
cgatgattaa aagaaacttt aacgcacccg agttgtctgg catcattgat attgaaaata    3780
ctgcatcttt ggttgtagat aagttttttg atagttattt gcttaaagaa aaaagaaaac    3840
caaataaaaa tgtttctttg ttcagtagag agtctctcaa tagatggtta gaaaagcagg    3900
aacaggtaac aataggccag ctcgcagatt ttgattttgt ggatttgcca gcagttgatc    3960
agtacagaca catgattaaa gcacaaccca acaaaagtt ggacacttca atccaaacgg      4020
agtacccggc tttgcagacg attgtgtacc attcaaaaaa gatcaatgca atattcggcc    4080
cgttgtttag tgagcttact aggcaattac tggacagtgt tgattcgagc agattttgt     4140 ttttcacaag aaagacacca gcgcagattg aggatttctt cggagatctc gacagtcatg    4200
tgccgatgga tgtcttggag ctggatatat caaaatacga caaatctcag aatgaattcc    4260
actgtgcagt agaatacgag atctggcgaa gattgggttt cgaagacttc ttgggagaag    4320
tttgaaaaca agggcataga aagaccaccc tcaaggatta taccgcaggt ataaaaactt    4380
gcatctggta tcaaagaaag agcggggacg tcacgacgtt cattggaaac actgtgatca    4440
ttgctgcatg tttggcctcg atgcttccga tggagaaaat aatcaaagga gcctttgcg     4500 gtgacgatag tctgctgtac tttccaaagg gttgtgagtt tccggatgtg caacactccg    4560
cgaatcttat gtggaatttt gaagcaaaac tgtttaaaaa acagtatgga acttttgcg     4620 gaagatatgt aatacatcac gacagaggat gcattgtgta ttacgatccc ctaaagttga    4680
tctcgaaact tggtgctaaa cacatcaagg attgggaaca cttggaggag ttcagaaggt    4740
ctctttgtga tgttgctgtt tcgttgaaca attgtgcgta ttacacacag ttggacgacg    4800
ctgtatggga ggttcataag accgcccctc caggttcgtt tgtttataaa agtctggtga    4860
agtatttgtc tgataaagtt cttttagaa gtttgtttat agatggctct agttgttaaa     4920
ggaaaagtga atatcaatga gtttatcgac ctgacaaaaa tggagaagat cttaccgtcg    4980
atgtttaccc ctgtaaagag tgttatgtgt tccaaagttg ataaaataat ggttcatgag    5040
aatgagtcat tgtcaggggt gaaccttctt aaaggagtta agcttattga tagtggatac    5100
gtctgtttag ccggtttggt cgtcacgggc gagtggaact tgcctgacaa ttgcagagga    5160
ggtgtgagcg tgtgtctggt ggacaaaagg atggaaagag ccgacgaggc cactctcgga    5220
tcttactaca cagcagctgc aaagaaaaga tttcagttca aggtcgttcc caattatgct    5280
ataaccaccc aggacgcgat gaaaaacgtc tggcaagttt tagttaatat tagaaatgtg    5340
aagatgtcag cgggtttctg tccgctttct ctggagtttg tgtcggtgtg tattgtttat    5400
agaaataata taaaattagg tttgagagag aagattacaa acgtgagaga cggagggccc    5460
atggaactta cagaagaagt cgttgatgag ttcatggaag atgtccctat gtcgatcagg    5520
```

```
cttgcaaagt ttcgatctcg aaccggaaaa aagagtgatg tccgcaaagg gaaaaatagt   5580
agtagtgatc ggtcagtgcc gaacaagaac tatagaaatg ttaaggattt tggaggaatg   5640
agttttaaaa agaataattt aatcgatgat gattcggagg ctactgtcgc cgaatcggat   5700
tcgttttaaa tagatcttac agtatcacta ctccatctca gttcgtgttc ttgtcattaa   5760
ttaacggcct agggcggccg cggtcctgca acttgaggta gtcaagatgc ataataaata   5820
acggattgtg tccgtaatca cacgtggtgc gtacgataac gcatagtgtt tttccctcca   5880
cttaaatcga agggttgtgt cttggatcgc gcgggtcaaa tgtatatggt tcatatacat   5940
ccgcaggcac gtaataaagc gaggggttcg aatccccccg ttaccccggg tagggcccca   6000
ggtacccgga tgtgttttcc gggctgatga gtccgtgagg acgaaaccct gcaggcatgc   6060
aagcttggcg taatcatggt catagcctag ctagagtccg caaatcacca gtctctctct   6120
acaaatctat ctctctctat tttctccaga ataatgtgtg agtagttccc agataaggga   6180
attagggttc ttatagggtt tcgctcatgt gttgagcata taagaaaccc ttagtatgta   6240
tttgtatttg taaaatactt ctatcaataa aatttctaat tcctaaaacc aaaatccagt   6300
gacctgcagc ccggccgggg gatccactag cagattgtcg tttcccgcct tcagtttaaa   6360
ctatcagtgt ttgacaggat atattggcgg gtaaacctaa gagaaaagag cgtttattag   6420
aataatcgga tatttaaaag ggcgtgaaaa ggtttatccg ttcgtccatt tgtatgtgca   6480
tgccaaccac aggagatctc agtaaagcgc tggctgaacc cccagccgga actgacccca   6540
caaggcccta gcgtttgcaa tgcaccaggt catcattgac ccaggcgtgt tccaccaggc   6600
cgctgcctcg caactcttcg caggcttcgc cgacctgctc gcgccacttc ttcacgcggg   6660
tggaatccga tccgcacatg aggcggaagg tttccagctt gagcgggtac ggctcccggt   6720
gcgagctgaa atagtcgaac atccgtcggg ccgtcggcga cagcttgcgg tacttctccc   6780
atatgaattt cgtgtagtgg tcgccagcaa acagcacgac gatttcctcg tcgatcagga   6840
cctggcaacg ggacgttttc ttgccacggt ccaggacgcg gaagcggtgc agcagcgaca   6900
ccgattccag gtgcccaacg cggtcggacg tgaagcccat cgccgtcgcc tgtaggcgcg   6960
acaggcattc ctcggccttc gtgtaatacc ggccattgat cgaccagccc aggtcctggc   7020
aaagctcgta gaacgtgaag gtgatcggct cgccgatagg ggtgcgcttc gcgtactcca   7080
acacctgctg ccacaccagt tcgtcatcgt cggcccgcag ctcgacgccg gtgtaggtga   7140
tcttcacgtc cttgttgacg tggaaaatga ccttgttttg cagcgcctcg cgcgggattt   7200
tcttgttgcg cgtggtgaac agggcagagc gggccgtgtc gtttggcatc gctcgcatcg   7260
tgtccggcca cggcgcaata tcgaacaagg aaagctgcat ttccttgatc tgctgcttcg   7320
tgtgtttcag caacgcggcc tgcttggcct cgctgacctg ttttgccagg tcctcgccgg   7380 cggttttcg cttcttggtc gtcatagttc ctcgcgtgtc gatggtcatc gacttcgcca   7440
aacctgccgc ctcctgttcg agacgacgcg aacgctccac ggcggccgat ggcgcgggca   7500
gggcaggggg agccagttgc acgctgtcgc gctcgatctt ggccgtagct tgctggacca   7560
tcgagccgac ggactggaag gtttcgcggg gcgcacgcat gacggtgcgg cttgcgatgg   7620
tttcggcatc ctcggcggaa accccgcgct cgatcagttc ttgcctgtat gcttccggt   7680 caaacgtccg attcattcac cctccttgcg ggattgcccc gactcacgcc ggggcaatgt   7740
gcccttattc ctgatttgac ccgcctggtg ccttggtgtc cagataatcc accttatcgg   7800
caatgaagtc ggtcccgtag accgtctggc cgtccttctc gtacttggta ttccgaatct   7860
```

```
tgccctgcac gaataccagc gaccccttgc ccaaatactt gccgtgggcc tcggcctgag   7920
agccaaaaca cttgatgcgg aagaagtcgg tgcgctcctg cttgtcgccg catcgttgc   7980
gccacatcta ggtactaaaa caattcatcc agtaaaatat aatattttat tttctcccaa   8040
tcaggcttga tccccagtaa gtcaaaaaat agctcgacat actgttcttc cccgatatcc   8100
tccctgatcg accggacgca gaaggcaatg tcataccact tgtccgccct gccgcttctc   8160
ccaagatcaa taaagccact tactttgcca tctttcacaa agatgttgct gtctcccagg   8220
tcgccgtggg aaaagacaag ttcctcttcg ggcttttccg tctttaaaaa atcatacagc   8280
tcgcgcggat ctttaaatgg agtgtcttct tcccagtttt cgcaatccac atcggccaga   8340
tcgttattca gtaagtaatc caattcggct aagcggctgt ctaagctatt cgtatatggga  8400
caatccgata tgtcgatgga gtgaaagagc ctgatgcact ccgcatacag ctcgataatc   8460
ttttcagggc tttgttcatc ttcatactct tccgagcaaa ggacgccatc ggcctcactc   8520
atgagcagat tgctccagcc atcatgccgt tcaaagtgca ggacctttgg aacaggcagc   8580
tttccttcca gccatagcat catgtccttt tcccgttcca catcataggt ggtcccttta   8640
taccggctgt ccgtcatttt taaatatagg ttttcatttt ctcccaccag cttatatacc   8700
ttagcaggag acattccttc cgtatctttt acgcagcggt attttcgat cagttttttc    8760
aattccggtg atattctcat tttagccatt tattatttcc ttcctctttt ctacagtatt   8820
taaagatacc ccaagaagct aattataaca agacgaactc caattcactg ttccttgcat   8880
tctaaaacct taaataccag aaaacagctt ttcaaagtt gttttcaaag ttggcgtata    8940
acatagtatc gacggagccg attttgaaac cacaattatg ggtgatgctg ccaactcgag   9000
agcgggccgg gagggttcga aagggggggg cacccccctt cggcgtgcgc ggtcacgcgc   9060
acagggcgca gccctggtta aaaacaaggt ttataaatat tggtttaaaa gcaggttaaa   9120
agacaggtta gcggtggccg aaaaacgggc ggaaacccct gcaaatgctg gattttctgc   9180
ctgtggacag cccctcaaat gtcaataggt gcgcccctca tctgtcagca ctctgccccct  9240
caagtgtcaa ggatcgcgcc cctcatctgt cagtagtcgc gcccctcaag tgtcaataccc  9300
gcagggcact tatccccagg cttgtccaca tcatctgtgg gaaactcgcg taaaatcagg   9360
cgttttcgcc gatttgcgag gctggccagc tccacgtcgc cggccgaaat cgagcctgcc   9420
cctcatctgt caacgccgcg ccgggtgagt cggcccctca gtgtcaacg tccgcccctc    9480
atctgtcagt gagggccaag ttttccgcga ggtatccaca acgccggcgg ccggccgcgg   9540
tgtctcgcac acggcttcga cggcgtttct ggcgcgtttg cagggccata gacggccgcc   9600
agcccagcgg cgagggcaac cagcccggtg agctctagtg gactgatggg ctgcctgtat   9660
cgagtggtga ttttgtgccg agctgccggt cggggagctg ttggctggct ggtggcagga   9720
tatattgtgg tgtaaacaaa ttgacgctta gacaacttaa taacacattg cggacgtttt   9780
taatgtactg gggtggtttt ggtaccgggc ccccccctcga ggtcgacggt atcgataagc   9840
ttgatatcga attcctgcag gtcaacatgg tggagcacga cactctcgtc tactccaaga   9900
atatcaaaga tacagtctca gaagaccaaa gggctattga acttttcaa caaagggtaa   9960
tatcgggaaa cctcctcgga ttccattgcc cagctatctg tcacttcatc aaaaggacag   10020
tagaaaagga aggtggcacc tacaaatgcc atcattgcga taaaggaaag gctatcgttc   10080
aagatgcctc tgccgacagt ggtcccaaag atggaccccc acccacgagg agcatcgtgg   10140
aaaaagaaga cgttccaacc acgtcttcaa agcaagtgga ttgatgtgat aacatggtgg   10200
agcacgacac tctcgtctac tccaagaata tcaaagatac agtctcagaa gaccaaaggg   10260
```

```
ctattgagac ttttcaacaa agggtaatat cgggaaacct cctcggattc cattgcccag    10320
ctatctgtca cttcatcaaa aggacagtag aaaaggaagg tggcacctac aaatgccatc    10380
attgcgataa aggaaaggct atcgttcaag atgcctctgc cgacagtggt cccaaagatg    10440
gacccccacc cacgaggagc atcgtggaaa agaagacgt tccaaccacg tcttcaaagc     10500
aagtggattg atgtgatatc tccactgacg taagggatga cgcacaatcc cactatcctt    10560
cgcaagacct tcctctatat aaggaagttc atttcatttg gagagg                   10606

<210> SEQ ID NO 14
<211> LENGTH: 11473
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 14
gtatttttac aacaattacc aacaacaaca aacaacagac aacattacaa ttactattta      60
caattacaat ggcatacaca cagacagcta ccacatcagc tttgctggac actgtccgag     120
gaaacaactc cttggtcaat gatctagcaa agcgtcgtct ttacgacaca gcggttgaag     180
agtttaacgc tcgtgaccgc aggcccaagg tgaacttttc aaaagtaata agcgaggagc     240
agacgcttat tgctacccgg gcgtatccag aattccaaat tacattttat aacacgcaaa     300
atgccgtgca ttcgcttgca ggtggattgc gatctttaga actggaatat ctgatgatgc     360
aaattcccta cggatcattg acttatgaca taggcgggaa ttttgcatcg catctgttca     420
agggacgagc atatgtacac tgctgcatgc ccaacctgga cgttcgagac atcatgcggc     480
acgaaggcca gaaagacagt attgaactat acctttctag gctagagaga ggggggaaaa     540
cagtccccaa cttccaaaag gaagcatttg acagatacgc agaaattcct gaagacgctg     600
tctgtcacaa tactttccag acatgcgaac atcagccgat gcagcaatca ggcagagtgt     660
atgccattgc gctacacagc atatatgaca taccagccga tgagttcggg gcggcactct     720
tgaggaaaaa tgtccatacg tgctatgccg ctttccactt ctccgagaac ctgcttcttg     780
aagattcatg cgtcaatttg gacgaaatca acgcgtgttt ttcgcgcgat ggagacaagt     840
tgaccttttc ttttgcatca gagagtactc ttaattactg tcatagttat tctaatattc     900
ttaagtatgt gtgcaaaact tacttcccgg cctctaatag agaggtttac atgaaggagt     960
ttttagtcac cagagttaat acctggtttt gtaagttttc tagaatagat acttttcttt    1020
tgtacaaagg tgtggcccat aaaagtgtag atagtgagca gttttatact gcaatggaag    1080
acgcatggca ttacaaaaag actcttgcaa tgtgcaacag cgagagaatc ctccttgagg    1140
attcatcatc agtcaattac tggtttccca aaatgaggga tatggtcatc gtaccattat    1200
tcgacatttc tttggagact agtaagagga cgcgcaagga agtcttagtg tccaaggatt    1260
tcgtgtttac agtgcttaac cacattcgaa cataccaggc gaaagctctt acatacgcaa    1320 atgtttttgtc cttcgtcgaa tcgattcgat cgagggtaat cattaacggt gtgacagcga    1380
ggtccgaatg ggatgtggac aaatctttgt tacaatcctt gtccatgacg ttttacctgc    1440
atactaagct tgccgttcta aaggatgact tactgattag caagtttagt ctcggttcga    1500
aaacggtgtg ccagcatgtg tgggatgaga tttcgctggc gtttgggaac gcatttccct    1560
ccgtgaaaga gaggctcttg aacaggaaac ttatcagagt ggcaggcgac gcattagaga    1620
tcagggtgcc tgatctatat gtgaccttcc acgacagatt agtgactgag tacaaggcct    1680
```

```
ctgtggacat gcctgcgctt gacattagga agaagatgga agaaacggaa gtgatgtaca   1740
atgcactttc agaattatcg gtgttaaggg agtctgacaa attcgatgtt gatgtttttt   1800
cccagatgtg ccaatctttg aagttgacc caatgacggc agcgaaggtt atagtcgcgg    1860
tcatgagcaa tgagagcggt ctgactctca catttgaacg acctactgag gcgaatgttg   1920
cgctagcttt acaggatcaa gagaaggctt cagaaggtgc attggtagtt acctcaagag   1980
aagttgaaga accgtccatg aagggttcga tggccagagg agagttacaa ttagctggtc   2040
ttgctggaga tcatccggaa tcgtcctatt ctaagaacga ggagatagag tctttagagc   2100
agtttcatat ggcgacggca gattcgttaa ttcgtaagca gatgagctcg attgtgtaca   2160
cgggtccgat taaagttcag caaatgaaaa actttatcga tagcctggta gcatcactat   2220
ctgctgcggt gtcgaatctc gtcaagatcc tcaaagatac agctgctatt gaccttgaaa   2280
cccgtcaaaa gtttggagtc ttggatgttg catctaggaa gtggttaatc aaaccaacgg   2340
ccaagagtca tgcatggggt gttgttgaaa cccacgcgag gaagtatcat gtggcgcttt   2400
tggaatatga tgagcagggt gtggtgacat gcgatgattg gagaagagta gctgttagct   2460
ctgagtctgt tgtttattcc gacatggcga aactcagaac tctgcgcaga ctgcttcgaa   2520
acggagaacc gcatgtcagt agcgcaaagg ttgttcttgt ggacggagtt ccgggctgtg   2580
gaaaaaccaa agaaattctt tccagggtta attttgatga agatctaatt ttagtacctg   2640
ggaagcaagc cgcggaaatg atcagaagac gtgcgaattc ctcagggatt attgtggcca   2700
cgaaggacaa cgttaaaacc gttgattctt tcatgatgaa ttttgggaaa agcacacgct   2760
gtcagttcaa gaggttattc attgatgaag ggttgatgtt gcatactggt tgtgttaatt   2820
ttcttgtggc gatgtcattg tgcgaaattg catatgttta cggagacaca cagcagattc   2880
catacatcaa tagagtttca ggattcccgt accccgccca ttttgccaaa ttggaagttg   2940
acgaggtgga gacacgcaga actactctcc gttgtccagc cgatgtcaca cattatctga   3000
acaggagata tgagggcttt gtcatgagca cttcttcggt taaaaagtct gtttcgcagg   3060
agatggtcgg cggagccgcc gtgatcaatc cgatctcaaa acccttgcat ggcaagatct   3120 tgactttac ccaatcggat aaagaagctc tgctttcaag agggtattca gatgttcaca    3180
ctgtgcatga agtgcaaggc gagacatact ctgatgtttc actagttagg ttaacccta    3240 caccggtctc catcattgca ggagacagcc cacatgtttt ggtcgcattg tcaaggcaca   3300
cctgttcgct caagtactac actgttgtta tggatccttt agttagtatc attagagatc   3360
tagagaaact tagctcgtac ttgttagata tgtataaggt cgatgcagga acacaatagc   3420
aattacagat tgactcggtg ttcaaaggtt ccaatctttt tgttgcagcg ccaaagactg   3480
gtgatatttc tgatatgcag ttttactatg ataagtgtct cccaggcaac agcaccatga   3540
tgaataattt tgatgctgtt accatgaggt tgactgacat ttcattgaat gtcaaagatt   3600
gcatattgga tatgtctaag tctgttgctg cgcctaagga tcaaatcaaa ccactaatac   3660
ctatggtacg aacggcggca gaaatgccac gccagactgg actattggaa aatttagtgg   3720
cgatgattaa aagaaacttt aacgcacccg agttgtctgg catcattgat attgaaaata   3780
ctgcatcttt ggttgtagat aagtttttg atagttattt gcttaaagaa aaagaaaac    3840 caaataaaaa tgtttctttg ttcagtagag agtctctcaa tagatggtta gaaaagcagg   3900
aacaggtaac aataggccag ctcgcagatt ttgattttgt ggatttgcca gcagttgatc   3960
agtacagaca catgattaaa gcacaaccca aacaaaagtt ggacacttca atccaaacgg   4020
```

```
agtacccggc tttgcagacg attgtgtacc attcaaaaaa gatcaatgca atattcggcc    4080
cgttgtttag tgagcttact aggcaattac tggacagtgt tgattcgagc agattttgt     4140 ttttcacaag aaagacacca gcgcagattg aggatttctt cggagatctc gacagtcatg    4200
tgccgatgga tgtcttggag ctggatatat caaaatacga caaatctcag aatgaattcc    4260
actgtgcagt agaatacgag atctggcgaa gattgggttt cgaagacttc ttgggagaag    4320
tttggaaaca agggcataga aagaccaccc tcaaggatta taccgcaggt ataaaaactt    4380
gcatctggta tcaaagaaag agcggggacg tcacgacgtt cattggaaac actgtgatca    4440
ttgctgcatg tttggcctcg atgcttccga tggagaaaat aatcaaagga gccttttgcg    4500
gtgacgatag tctgctgtac tttccaaagg gttgtgagtt tccggatgtg caacactccg    4560
cgaatcttat gtggaatttt gaagcaaaac tgtttaaaaa acagtatgga tacttttgcg    4620
gaagatatgt aatacatcac gacagaggat gcattgtgta ttacgatccc ctaaagttga    4680
tctcgaaact tggtgctaaa cacatcaagg attgggaaca cttggaggag ttcagaaggt    4740
ctctttgtga tgttgctgtt tcgttgaaca attgtgcgta ttacacacag ttggacgacg    4800
ctgtatggga ggttcataag accgcccctc caggttcgtt tgtttataaa agtctggtga    4860
agtatttgtc tgataaagtt ctttttagaa gtttgtttat agatggctct agttgttaaa    4920
ggaaaagtga atatcaatga gtttatcgac ctgacaaaaa tggagaagat cttaccgtcg    4980
atgtttaccc ctgtaaagag tgttatgtgt tccaaagttg ataaataat ggttcatgag    5040 aatgagtcat tgtcaggggt gaaccttctt aaaggagtta agcttattga tagtggatac    5100
gtctgtttag ccggtttggt cgtcacgggc gagtggaact tgcctgacaa ttgcagagga    5160
ggtgtgagcg tgtgtctggt ggacaaaagg atggaaagag ccgacgaggc cactctcgga    5220
tcttactaca cagcagctgc aaagaaaaga tttcagttca aggtcgttcc caattatgct    5280
ataaccaccc aggacgcgat gaaaaacgtc tggcaagttt tagttaatat tagaaatgtg    5340
aagatgtcag cgggttttctg tccgcttttct ctggagtttg tgtcggtgtg tattgtttat    5400
agaaataata taaaattagg tttgagagag aagattacaa acgtgagaga cggagggccc    5460
atggaactta cagaagaagt cgttgatgag ttcatggaag atgtccctat gtcgatcagg    5520
cttgcaaagt ttcgatctcg aaccggaaaa aagagtgatg tccgcaaagg gaaaaatagt    5580
agtagtgatc ggtcagtgcc gaacaagaac tatagaaatg ttaaggattt tggaggaatg    5640
agttttaaaa agaataattt aatcgatgat gattcggagg ctactgtcgc cgaatcggat    5700
tcgttttaaa tagatcttac agtatcacta ctccatctca gttcgtgttc ttgtcattaa    5760
ttaaatggct agcaaaggag aagaactttt cactggagtt gtcccaattc ttgttgaatt    5820
agatggtgat gttaatgggc acaaattttc tgtcagtgga gagggtgaag gtgatgctac    5880
atacggaaag cttacccctta aatttatttg cactactgga aaactacctg ttccatggcc    5940
aacacttgtc actactttct cttatggtgt tcaatgcttt tcccgttatc cggatcatat    6000
gaaacggcat gactttttca agagtgccat gcccgaaggt tatgtacagg aacgcactat    6060
atctttcaaa gatgacggga actacaagac gcgtgctgaa gtcaagtttg aaggtgatac    6120
ccttgttaat cgtatcgagt taaaaggtat tgattttaaa gaagatggaa acattctcgg    6180
acacaaactc gagtacaact ataactcaca caatgtatac atcacggcag acaaacaaaa    6240
gaatggaatc aaagctaact tcaaaattcg ccacaacatt gaagatggat ccgttcaact    6300
agcagaccat tatcaacaaa atactccaat tggcgatggc cctgtccttt taccagacaa    6360
ccattacctg tcgacacaat ctgccctttc gaaagatccc aacgaaaagc gtgaccacat    6420
```

```
gggccttctt gagtttgtaa ctgctgctgg gattacacat ggcatggatg agctctacaa    6480
ataatgaggc ggccgcactc cggctactta gctattgttg tgagatttcc taaaataaag    6540
tcactgaaga cttaaaattc agggtggctg ataccaaaat cagcagtggt tgttcgtcca    6600
cttaaatata acgattgtca tatctggatc caacagttaa accatgtgat ggtgtatact    6660
gtggtatggc gtaaaacaac ggaaaagtcg ctgaagactt aaaattcagg gtggctgata    6720
ccaaaatcag cagtggttgt tcgtccactt aaaaataacg attgtcatat ctggatccaa    6780
cagttaaacc atgtgatggt gtatactgtg gtatggcgta acaacggag aggttcgaat    6840 cctcccctaa ccgcgggtag cggcccaggt acccggatgt gttttccggg ctgatgagtc    6900
cgtgaggacg aaaccctgca ggcatgcaag cttggcgtaa tcatggtcat agcctagcta    6960
gagtccgcaa atcaccagtc tctctctaca aatctatctc tctctatttt ctccagaata    7020
atgtgtgagt agttcccaga taagggaatt agggttctta tagggtttcg ctcatgtgtt    7080
gagcatataa gaaaccctta gtatgtattt gtatttgtaa aatacttcta tcaataaaat    7140
ttctaattcc taaaaccaaa atccagtgac ctgcagcccg gccgggggat ccactagcag    7200
attgtcgttt cccgccttca gtttaaacta tcagtgtttg acaggatata ttggcgggta    7260
aacctaagag aaaagagcgt ttattagaat aatcggatat ttaaaagggc gtgaaaaggt    7320
ttatccgttc gtccatttgt atgtgcatgc caaccacagg agatctcagt aaagcgctgg    7380 ctgaacccc agccggaact gaccccacaa ggccctagcg tttgcaatgc accaggtcat    7440
cattgaccca ggcgtgttcc accaggccgc tgcctcgcaa ctcttcgcag gcttcgccga    7500
cctgctcgcg ccacttcttc acgcgggtgg aatccgatcc gcacatgagg cggaaggttt    7560
ccagcttgag cgggtacggc tcccggtgcg agctgaaata gtcgaacatc cgtcgggccg    7620
tcggcgacag cttgcggtac ttctcccata tgaatttcgt gtagtggtcg ccagcaaaca    7680
gcacgacgat ttcctcgtcg atcaggacct ggcaacggga cgttttcttg ccacggtcca    7740
ggacgcggaa gcggtgcagc agcgacaccg attccaggtg cccaacgcgg tcggacgtga    7800
agcccatcgc cgtcgcctgt aggcgcgaca ggcattcctc ggccttcgtg taataccggc    7860
cattgatcga ccagcccagg tcctggcaaa gctcgtagaa cgtgaaggtg atcggctcgc    7920 cgatagggt gcgcttcgcg tactccaaca cctgctgcca caccagttcg tcatcgtcgg    7980
cccgcagctc gacgccggtg taggtgatct tcacgtcctt gttgacgtgg aaaatgacct    8040
tgttttgcag cgcctcgcgc gggattttct tgttgcgcgt ggtgaacagg gcagagcggg    8100
ccgtgtcgtt tggcatcgct cgcatcgtgt ccggccacgg cgcaatatcg aacaaggaaa    8160
gctgcatttc cttgatctgc tgcttcgtgt gtttcagcaa cgcggcctgc ttggcctcgc    8220
tgacctgttt tgccaggtcc tcgccggcgg ttttcgcttc ttggtcgtc atagttcctc    8280 gcgtgtcgat ggtcatcgac ttcgccaaac ctgccgcctc ctgttcgaga cgacgcgaac    8340
gctccacggc ggccgatggc gcgggcaggg caggggagc cagttgcacg ctgtcgcgct    8400
cgatcttggc cgtagcttgc tggaccatcg agccgacgga ctggaaggtt tcgcggggcg    8460
cacgcatgac ggtgcggctt gcgatggttt cggcatcctc ggcggaaaac cccgcgtcga    8520
tcagttcttg cctgtatgcc ttccggtcaa acgtccgatt cattcaccct ccttgcggga    8580
ttgccccgac tcacgccggg gcaatgtgcc cttattcctg atttgacccg cctggtgcct    8640
tggtgtccag ataatccacc ttatcggcaa tgaagtcggt cccgtagacc gtctggccgt    8700
ccttctcgta cttggtattc cgaatcttgc cctgcacgaa taccagcgac cccttgccca    8760
```

```
aatacttgcc gtgggcctcg gcctgagagc caaaacactt gatgcggaag aagtcggtgc    8820
gctcctgctt gtcgccggca tcgttgcgcc acatctaggt actaaaacaa ttcatccagt    8880
aaaatataat attttatttt ctcccaatca ggcttgatcc ccagtaagtc aaaaaatagc    8940
tcgacatact gttcttcccc gatatcctcc ctgatcgacc ggacgcagaa ggcaatgtca    9000
taccacttgt ccgccctgcc gcttctccca agatcaataa agccacttac tttgccatct    9060
ttcacaaaga tgttgctgtc tcccaggtcg ccgtgggaaa agacaagttc ctcttcgggc    9120
ttttccgtct ttaaaaaatc atacagctcg cgcggatctt taaatggagt gtcttcttcc    9180
cagttttcgc aatccacatc ggccagatcg ttattcagta agtaatccaa ttcggctaag    9240
cggctgtcta agctattcgt atagggacaa tccgatatgt cgatggagtg aaagagcctg    9300
atgcactccg catacagctc gataatcttt tcagggcttt gttcatcttc atactcttcc    9360
gagcaaagga cgccatcggc ctcactcatg agcagattgc tccagccatc atgccgttca    9420
aagtgcagga cctttggaac aggcagcttt ccttccagcc atagcatcat gtccttttcc    9480
cgttccacat cataggtggt cccttatac cggctgtccg tcattttaa atataggttt    9540
tcattttctc ccaccagctt atataccta gcaggagaca ttccttccgt atcttttacg    9600
cagcggtatt tttcgatcag ttttttcaat tccggtgata ttctcatttt agccatttat    9660
tatttccttc ctcttttcta cagtatttaa agataccccca agaagctaat tataacaaga    9720
cgaactccaa ttcactgttc cttgcattct aaaaccttaa ataccagaaa acagcttttt    9780
caaagttgtt ttcaaagttg gcgtataaca tagtatcgac ggagccgatt ttgaaaccac    9840
aattatgggt gatgctgcca actcgagagc gggccgggag ggttcgagaa ggggggggcac    9900
cccccttcgg cgtgcgcggt cacgcgcaca gggcgcagcc ctggttaaaa acaaggttta    9960
taaatattgg tttaaaagca ggttaaaaga caggttagcg gtggccgaaa aacgggcgga   10020
aacccttgca aatgctggat tttctgcctg tggacagccc ctcaaatgtc aataggtgcg   10080
cccctcatct gtcagcactc tgcccctcaa gtgtcaagga tcgcgcccct catctgtcag   10140
tagtcgcgcc cctcaagtgt caataccgca gggcacttat ccccaggctt gtccacatca   10200
tctgtgggaa actcgcgtaa aatcaggcgt tttcgccgat ttgcgaggct ggccagctcc   10260
acgtcgccgg ccgaaatcga gcctgcccct catctgtcaa cgccgcgccg ggtgagtcgg   10320
cccctcaagt gtcaacgtcc gcccctcatc tgtcagtgag ggccaagttt ccgcgaggt    10380
atccacaacg ccggcggccg gccgcggtgt ctcgcacacg gcttcgacgg cgtttctggc   10440
gcgtttgcag ggccatagac ggccgccagc ccagcggcga gggcaaccag cccggtgagc   10500
tctagtggac tgatgggctg cctgtatcga gtggtgattt tgtgccgagc tgccggtcgg   10560
ggagctgttg gctggctggt ggcaggatat attgtggtgt aaacaaattg acgcttagac   10620
aacttaataa cacattgcgg acgtttttaa tgtactgggg tggttttggt accgggcccc   10680
ccctcgaggt cgacggtatc gataagcttg atatcgaatt cctgcaggtc aacatggtgg   10740
agcacgacac tctcgtctac tccaagaata tcaaagatac agtctcagaa gaccaaaggg   10800
ctattgagac ttttcaacaa agggtaatat cgggaaacct cctcggattc cattgcccag   10860
ctatctgtca cttcatcaaa aggacagtag aaaaggaagg tggcacctac aaatgccatc   10920
attgcgataa aggaaaggct atcgttcaag atgcctctgc cgacagtggt cccaaagatg   10980
gacccccacc cacgaggagc atcgtggaaa aagaagacgt tccaaccacg tcttcaaagc   11040
aagtggattg atgtgataac atggtggagc acgacactct cgtctactcc aagaatatca   11100
aagatacagt ctcagaagac caaagggcta ttgagacttt tcaacaaagg gtaatatcgg   11160
```

-continued

```
gaaacctcct cggattccat tgcccagcta tctgtcactt catcaaaagg acagtagaaa    11220
aggaaggtgg cacctacaaa tgccatcatt gcgataaagg aaaggctatc gttcaagatg    11280
cctctgccga cagtggtccc aaagatggac ccccacccac gaggagcatc gtggaaaaag    11340
aagacgttcc aaccacgtct tcaaagcaag tggattgatg tgatatctcc actgacgtaa    11400
gggatgacgc acaatcccac tatccttcgc aagaccttcc tctatataag gaagttcatt    11460
tcatttggag agg                                                      11473
```

<210> SEQ ID NO 15
<211> LENGTH: 3
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15 aga                                                                  3

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ttaattaacg gcctagggcg gccgc                                          25

<210> SEQ ID NO 17
<211> LENGTH: 219
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
ggtcctgcaa cttgaggtag tcaagatgca taataaataa cggattgtgt ccgtaatcac    60
acgtggtgcg tacgataacg catagtgttt ttccctccac ttaaatcgaa gggttgtgtc    120
ttggatcgcg cgggtcaaat gtatatggtt catatacatc cgcaggcacg taataaagcg    180
aggggttcga atcccccgt taccccggt aggggccca                             219
```

<210> SEQ ID NO 18
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
atcgaggcct t                                                         11

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

```
<400> SEQUENCE: 19

His His His His His His
 1               5

<210> SEQ ID NO 20
<211> LENGTH: 9
<212> TYPE: PRT
<213> ORGANISM: Influenza A virus

<400> SEQUENCE: 20

Tyr Pro Tyr Asp Val Pro Asp Tyr Ala
 1               5
```

SYSTEM FOR EXPRESSION OF GENES IN PLANTS FROM A VIRUS-BASED EXPRESSION VECTOR

CROSS-REFERENCE TO RELATED APPLICATIONS

This application claims the benefit of the PCT/US2008/001101 filed Jan. 28, 2008, which claims priority to the U.S. Provisional Application Nos. 60/898,051 filed Jan. 29, 2007, and 60/961,728 filed Jul. 24, 2007, the entire disclosures of which are expressly incorporated herein by reference.

STATEMENT REGARDING FEDERALLY SPONSORED RESEARCH

This invention was not made with any Government support and the Government has no rights in this invention.

TECHNICAL FIELD AND INDUSTRIAL APPLICABILITY OF THE INVENTION

This invention is directed to novel expression vectors, including Tobacco Mosaic Virus (TMV) expression vectors, methods for modifying such vectors, and uses of the same.

BACKGROUND OF THE INVENTION

Plant virus-based vectors allow for the rapid, transient expression of proteins in whole plants (Pogue et al. 2002; Scholthof et al. 2002). Although many different plant viruses have been modified to function as expression vectors, Tobacco Mosaic Virus (TMV) based vectors express the highest levels of foreign protein in plants (Pogue et al. 1998; Yusibov et al. 1999). TMV-based vectors were among the first viral vectors to be used for either gene expression or gene silencing in plants (Fitzmaurice et al. 2002; Kumagai et al. 1995; Kumagai et al. 1993). They have been effective vectors for the production of many different kinds of proteins in plants including allergens (Breiteneder et al. 2001; Krebitz et al. 2000), antibodies (Giritch et al. 2006) or antibody fragments (McCormick et al. 1999), and vaccine candidates (Gleba et al. 2005; Turpen et al. 1995).

TMV is an RNA virus that expresses large amounts of coat protein (CP), from a subgenomic promoter. To convert TMV to an efficient expression vector, an additional, heterologous coat protein subgenomic promoter and restriction enzyme sites for cloning of foreign DNA sequences were inserted into a T7 promoter driven cDNA clone of TMV (Shivprasad et al. 1999). In vitro transcription of this plasmid with T7 RNA polymerase is needed to generate biologically active transcripts. Transcripts are typically rub-inoculated by hand onto plants to initiate an infection (Pogue et al. 1998). The in vitro transcription and rub inoculation steps, in particular, add significantly to the cost and complexity of using TMV vectors.

Agroinfection (Grimsley 1995; Grimsley et al. 1986) is an alternative, less-expensive strategy for infecting plants with RNA viruses. In agroinfection, a plant functional promoter and RNA virus cDNA are transferred as T-DNA from *Agrobacterium* into plant cells. The T-DNA is transcribed in planta, to generate biologically active viral RNAs that can initiate self-replication. Although agroinfection has been used for many different plant RNA viruses, it has not been routinely used with TMV-based vectors.

Recently, an agroinfection-compatible TMV expression vector was constructed with extensive modifications to the TMV cDNA. These alterations included multiple mutations, to destroy cryptic introns, and insertion of multiple plant-gene introns into the TMV cDNA sequences in a binary vector (Marillonnet et al. 2005). These mutations improved the efficiency by which TMV vectors can be introduced into plants by agroinfection and are used in a process called "magnifection" (Gleba et al. 2005; Marillonnet et al. 2004). In magnifection, whole plants are submerged and infiltrated with *Agrobacterium* cultures carrying intron-modified TMV sequences in a binary vector. While the magnifection process is efficient, it is not easily adapted to a high throughput workflow. Also, the increased size of the intron-modified vectors can make cloning into these vectors more challenging. In addition, it is not clear if the intron-modified vectors are absolutely required for efficient local and systemic infection of plants with TMV when using standard agroinfection procedures.

In addition, as interest in proteomics, biochemistry and protein structure increases there is an increasing need for efficient, easy-to-use recombinant protein expression systems. Improving transient expression vectors so they are easier to use, more cost-effective and produce higher levels of recombinant proteins will be of great use.

Certain transient expression systems take advantage of the ability of *Agrobacterium tumefaciens* to transfer DNAs into plant cells. *A. tumefaciens* cell suspensions simply infiltrated (or injected) into leaves can efficiently transfer sequences from the T-DNA region of a modified *A. tumefaciens* Ti (binary) plasmid into plant cells. If the T-DNA transferred into the plant cell contains a DNA sequence of interest joined to a plant-functional promoter, the transferred DNA would be transcribed in the plant nucleus. One disadvantage of this approach, however, is that the expression of the T-DNA is generally quite low and transient and expression drops off after 5 days or so.

It was recently demonstrated that one reason for this was that post-transcriptional gene silencing (PTGS) directed toward the transcribed T-DNA was being induced in the plant after agroinfiltration. It was determined that this could be at least partially overcome by using two different *A. tumefaciens* cultures to simultaneously co-introduce T-DNAs for both a cauliflower mosaic virus 35S promoter (35S) driven gene of interest and a 35S driven RNA silencing suppressor gene into cells. Ectopic transient expression of an RNA silencing suppressor protein (such as the p19 protein from tomato bushy stunt virus) suppressed the PTGS of the introduced T-DNA. This resulted in an increase in the amount of recombinant protein expressed. For some proteins, ectopic co-expression of p19 resulted in a nearly 50-fold increase in recombinant protein expression levels (Voinnet et al., 2003).

Partially because of this improvement, this strategy has become one of the more commonly used plant transient expression systems. Using this strategy, hundreds of plant proteins have been expressed in a relatively high-throughput fashion (Popescu et al., 2007). One limitation of this strategy, however, is that relatively high concentrations of *A. tumefaciens* cell suspensions must be infiltrated into leaves in order to get the highest expression levels possible. For some plant species the infiltration of such high concentrations of *A. tumefaciens* can elicit negative (hypersensitive) responses from the plant (unpublished observations).

Other transient expression systems are based on plant viruses such as TMV, tobacco mosaic virus. TMV is a rod-shaped virus that has a single stranded 'plus sense' RNA genome. TMV expresses four proteins from three open reading frames. Two viral genes (the viral 'movement protein' and the capsid protein) are expressed from separate subgenomic promoters. To convert TMV into an expression vector, an additional subgenomic promoter was inserted into the viral genome to drive the expression of an inserted foreign gene. Plants can be inoculated with TMV vectors through a process called "agroinfection." In agroinfection, *A. tumefaciens* was used to deliver a T-DNA comprised of a 35S promoter driven TMV cDNA to plant cells. Transcription of the T-DNA in the plant nucleus gave rise to an RNA that was capable of initiating self-replication in the cytoplasm. Multiple reports have documented the low agroinfection efficiency of the typical 35S-driven TMV vector (Turpen et al., 1993; Marillonnet et al., 2005; Man and Epel, 2006).

Therefore, in spite of intron-modified TMV vectors that have been recently constructed, there remains a need for TMV expression vectors with at least one or more of the following features: 1) contains convenient cloning sites for genes of interest; 2) can be used to infect plants in an easy and cost-effective manner; and, 3) leads to efficient systemic infection of inoculated plants.

SUMMARY OF THE INVENTION

In one aspect, there are provided novel Tobacco Mosaic Virus (TMV) expression vectors and novel methods for modifying TMV vectors. The methods provide modifications that improve both the options for cloning genes into TMV and the ease and efficiency of infecting plants with TMV vectors.

In one particular aspect, a 35S-promoter driven TMV based expression vector was constructed in the mini-binary plasmid pCB301. Plants were reliably infected by TMV vectors via an agroinfection method. In one embodiment, the agroinfection efficiency was dramatically increased when the gene for the RNA silencing suppressor p19 was co-introduced along with the 35S driven TMV clone. This modification makes it possible to recover TMV-expressed recombinant proteins from the agroinfiltrated tissue itself.

In another aspect, the cloning options were improved by the development of a simple, novel and inexpensive method for cloning DNA inserts into the agroinfection-compatible TMV expression vector. The cloning method allows for the efficient, directional cloning of PCR products, without the need for restriction enzyme digestion of PCR products. The cloning method does not rely on expensive topoisomerase or recombinase enzymes and uses commonly available enzymes.

In another aspect, there is provided a TMV-based expression vector system that facilitates the use of TMV vectors, especially in high-throughput experiments.

In another aspect, the vectors and methods can easily be applied to other expression vector systems.

In one particular aspect, there is provided an improvement to transient expression, which is a rapid, useful approach for producing proteins of interest in plants.

In particular, there is described herein a system for improving the TMV-based transient expression vectors in order to express very high levels of foreign proteins in plants where the TMV vectors are efficiently delivered to plant cells by agroinfection.

In one particular aspect, there is provided an agroinfection method that is very efficient and which uses a 35S promoter-driven TMV replicon that lacks the TMV coat protein (CP) gene sequence.

In another particular aspect, there is provided a "CP deletion" TMV expression vector that has several useful features as a transient expression system including: improved ease of use, higher protein expression rates, and improved biocontainment. In one embodiment, by using the CP deletion TMV expression vector, foreign proteins were expressed at levels of 3-5 mg/gm fresh weight of plant tissue.

In another particular aspect, there is provided a transient expression vector that is a useful tool for expressing recombinant proteins in plants. In one embodiment, the transient expression vector is especially useful for high-throughput expression applications.

There is also provided herein a process where the DNA sequence encoding the RNA replicon is stably integrated into a plant cell genome. In yet another aspect, there is provided herein a vector where the DNA encoding the RNA replicon is stably integrated into the genome of the plant cell. In still another aspect, there is provided herein a method where introducing the vector comprises performing Agro bacteria-mediated transformation, biolistic-mediated transformation or Whiskers-mediated transformation.

Various objects and advantages of this invention will become apparent to those skilled in the art from the following detailed description of the preferred embodiment, when read in light of the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

pJL22 contains the TMV 5' and 3' ends and Rz sequence in an *Agrobacterium* binary vector. pJL 22 lacks approximately 4 kb of internal TMV vector sequence. T-DNA borders (T, black boxes) are shown in all binary vector diagrams. Locations of individual restriction enzyme sites used in vector construction are identified.

Sequence of multiple cloning sites (MCS) in pJL36 [SEQ ID NO: 16] and 43 [SEQ ID NO: 8] are presented. Restriction enzyme recognition sequences are underlined. Because SapI is non-palindromic (GCTCTTC N1/4) both strands of the MCS of pJL43 are presented for clarity. Location of gene sequences for Replicase (Replicase), movement protein (MP), Green Fluorescent Protein (GFP) and coat protein (CP) are identified. Other Abbreviations used: T7, T7 RNA polymerase promoter; 35S, Cauliflower mosaic virus (CaMV) 35S promoter; 3'T, CaMV 3' terminator sequence. Location of subgenomic promoters are only identified in the p30BGFP diagram. Drawings not to scale.

FIG. 2: Diagram of a Sticky RICE cloning reaction into pJL43. Sticky RICE uses mixtures of DNA polymerase and ligase (and, optionally, polynucleotide kinase) with specially designed vector and insert DNAs to directionally ligate DNAs. Single stranded 3 nt, 5' overhangs are generated on pJL43 [SEQ ID NO: 8] by digestion the restriction endonuclease SapI (underlined). Vector is treated with phosphatase after digestion to remove phosphates from 5' ends of DNA. I. Purified PCR product [amplified with 5' phosphorylated primers that begin with 5'GGCCWW and 5'GCWW (W=A or T)] is added to SapI cut pJL43. II. A mixture of T4 DNA polymerase, the nucleotides dATP/dTTP and T4 DNA ligase are added to combined vector and PCR product. During this step the 5' overhangs of SapI cut pJL43 are altered by the T4

DNA polymerase. A single G residue is removed from the 3' end of the left end of the SapI cut vector, to generate a 5' overhang of GGCC. A single A residue is added to the 3' end of the right end of the SapI cut vector, to generate a 5' overhang of GC. Similarly, the 3' to 5' exonuclease activity of T4 DNA polymerase in the presence of dATP and dTTP removes G or C residues from the 3' ends of the PCR product. Complementary 5' overhangs in vector and PCR product (insert) guide annealing of DNAs. III. Annealed DNAs are joined by T4 DNA ligase. Sequences of the PCR product are in bold type. Vector sequences in final joined product are in all caps. The recognition sequences for the restriction endonucleases StuI (AGGCCT) and Hind III (AAGCTT) are generated at the vector-insert junctions. ATCGAggcctt is disclosed as SEQ ID NO: 18.

Figure 3A:
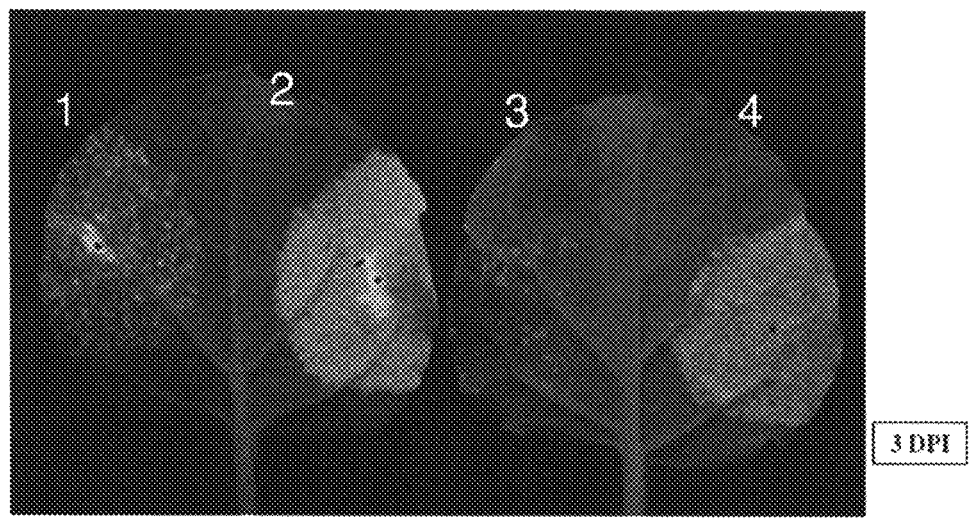
Figure 3B:
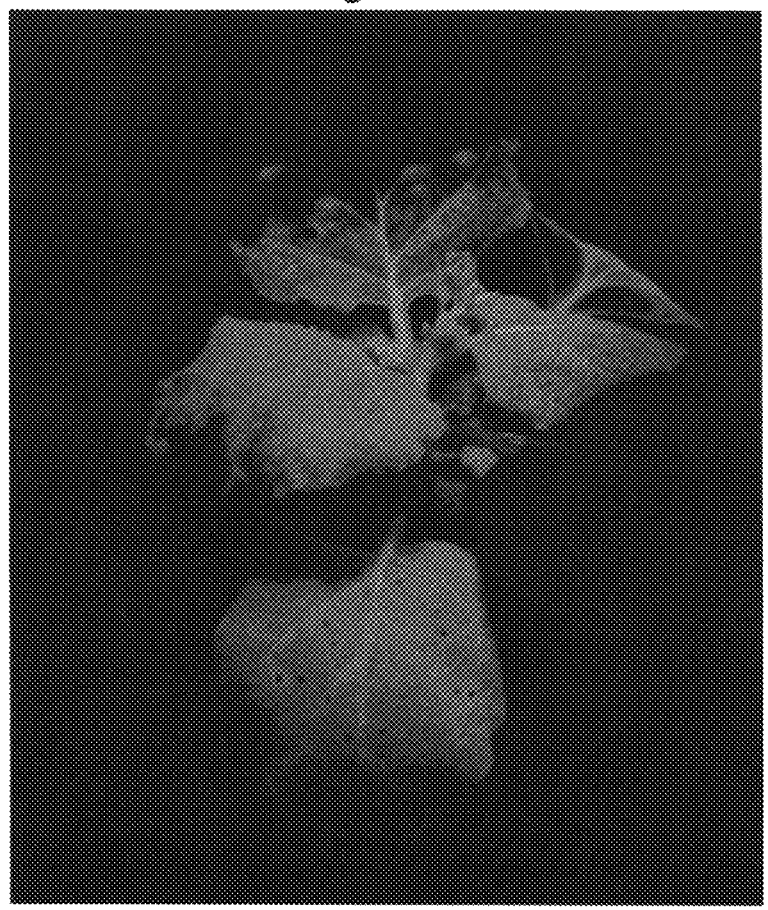

FIGS. 3A-3B: Agroinfection of plants with pJL43:GFP vector. FIG. 3A: Effect of p19 on agroinfection efficiency of a 35S driven TMV expression vector. *Agrobacterium* cultures containing plasmids pJL43:GFP (35S driven TMV expression vector with GFP insert), pJL4 (empty vector control), or pJL3:p19 (35S driven p19 gene) were suspended at an $OD_{600}$ of 1.0 in induction media. Cultures sat at room temperature overnight prior to infiltration into *N. benthamiana* leaves. Leaves were infiltrated with a 1:1 mixture of pJL43:GFP with pJL4 (FIG. 3A-1) or pJL3:p19 (FIG. 3A-2) culture. Leaves infiltrated with 1:50 dilution of pJL43:GFP combined 1:1 with undiluted pJL4 (FIG. 3A-3) or pJL3:p19 (FIG. 3A-4) cultures. Leaves were photographed under UV illumination approximately 3 days post infiltration. FIG. 3B: Systemic infection of *N. benthamiana* plant with TMV:GFP approximately 11 days after infiltration with *Agrobacterium*/pJL43:GFP. Plant photographed under UV light.

Figure 4A:
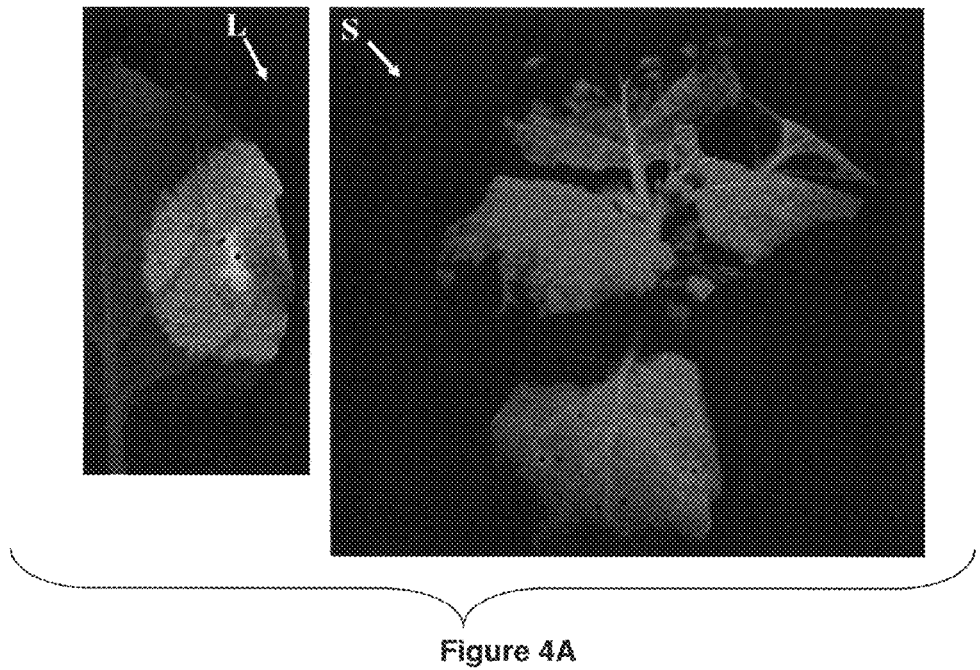

FIG. 4A: Photographs showing expression of Green fluorescent protein (GFP) from TMV:GFP in local or systemically infected tissue. *N. benthamiana* plants were infiltrated with a 1:1 mixture of pJL43:GFP and pJL3:p19 *Agrobacterium* cultures (both at an $OD_{600}$ of 1.0). Five days post infiltration (DPI) infiltrated tissue was collected and extracted (local, or L-sample). About 14 days post infiltration a leaf systemically infected with TMV:GFP was collected and extracted (S-sample). Extraction conditions: leaf tissue was ground in the presence of 2 mls 50 mM Acetate buffer, pH 5.0 per gram fresh weight. Extract was heated at 42° C. 10 minutes and centrifuged 10 minutes at 13K×g to clarify. Supernatants (5 µl aliquots) were analyzed on 4-20% SDS-PAGE gradient gel. Gel was stained with Coomassie blue.

Figure 4B:
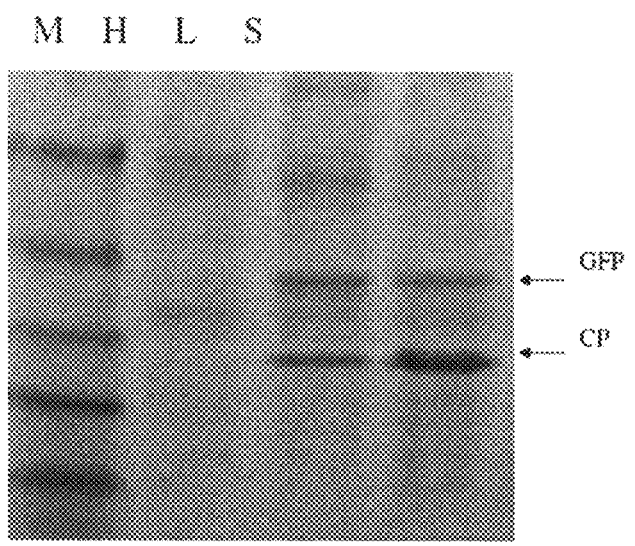

FIG. 4B: SDS-PAGE showing Lane M; MW marker; H, healthy plant extract; L, Local extract; S, Systemic extract. CP, 17 kDa TMV coat protein, GFP, 26.8 kDa GFP. Local protein sample was a 5 DPI leaf. Systemic leaf was from a plant agroinfected with pJL43:GFP 14 days prior to harvest.

Figure 5A:
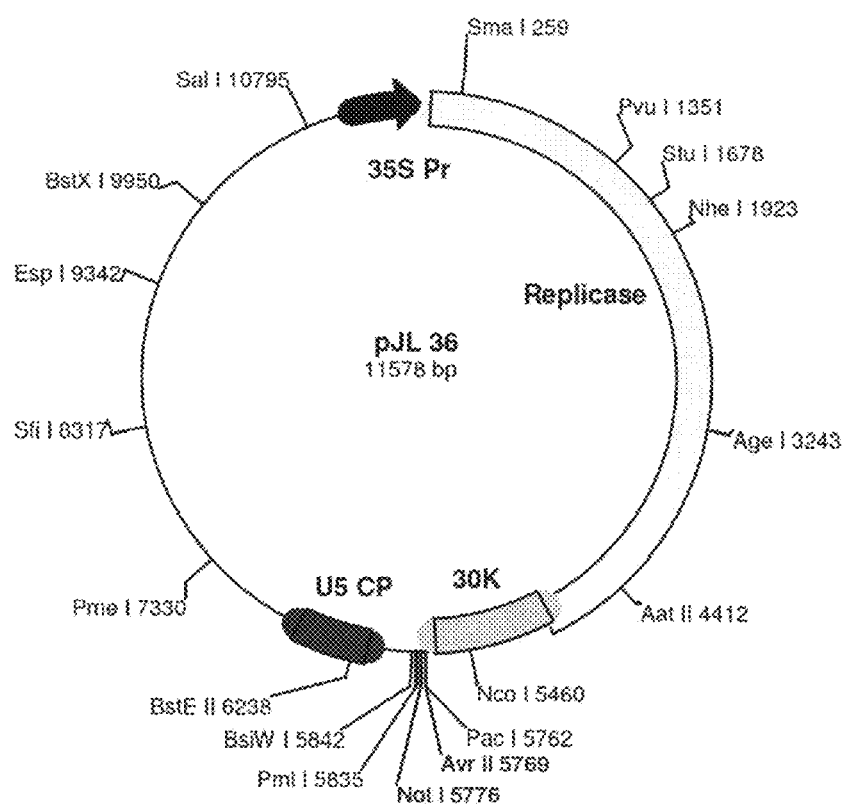

FIG. 5A: pJL36-35S driven 30B type TMV based expression vector. Has PacI-AvrII and NotI sites for cloning. Kan resistant vector replicates in *E. coli* or *Agrobacterium*. Agroinfiltration vector. T-DNA borders not shown in map. Vector backbone=pCB301.

FIG. 5B: pJL36 vector DNA sequence [SEQ ID NO: 5]: nt #1=first nt of TMV U1. Description: 35S promoter driven TMV based expression vector in *Agrobacterium* compatible binary vector. Has PacI (ttaattaa), AvrII (cctagg) and NotI (gcggccgc) sites for cloning.

Figure 6:
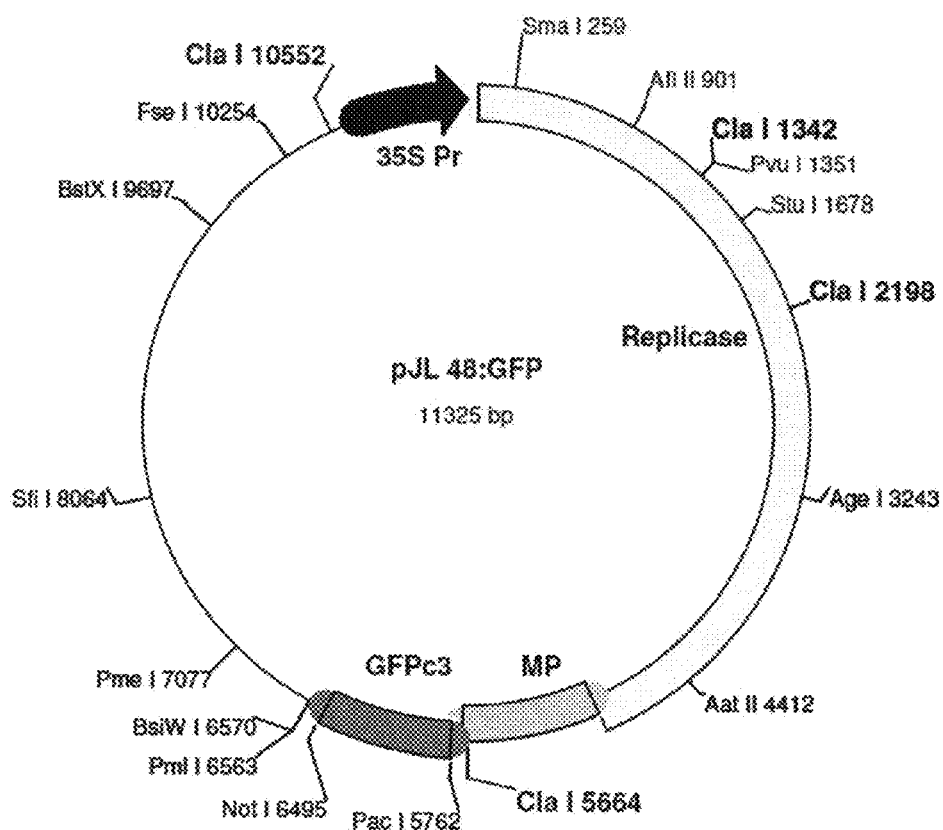

FIG. 6: pJL48 (pJL-TRBO)— GFP 35S driven TMV in binary vector with deletion of the CP gene. Kan resistance marker and T-DNA borders not shown in map. Plasmid replicates in either *Agrobacterium* or *E. coli*. Construction: GFPc3 gene (PCR product of oligos JAL 12 and 13). Digested with PacI-SpeI. Ligated into PacI-AvrII cut pJL48 (pJL-TRBO). Use: infiltrate *Agrobacterium* containing this plasmid into *N. benth* plants to produce GFP.

Figure 7A:
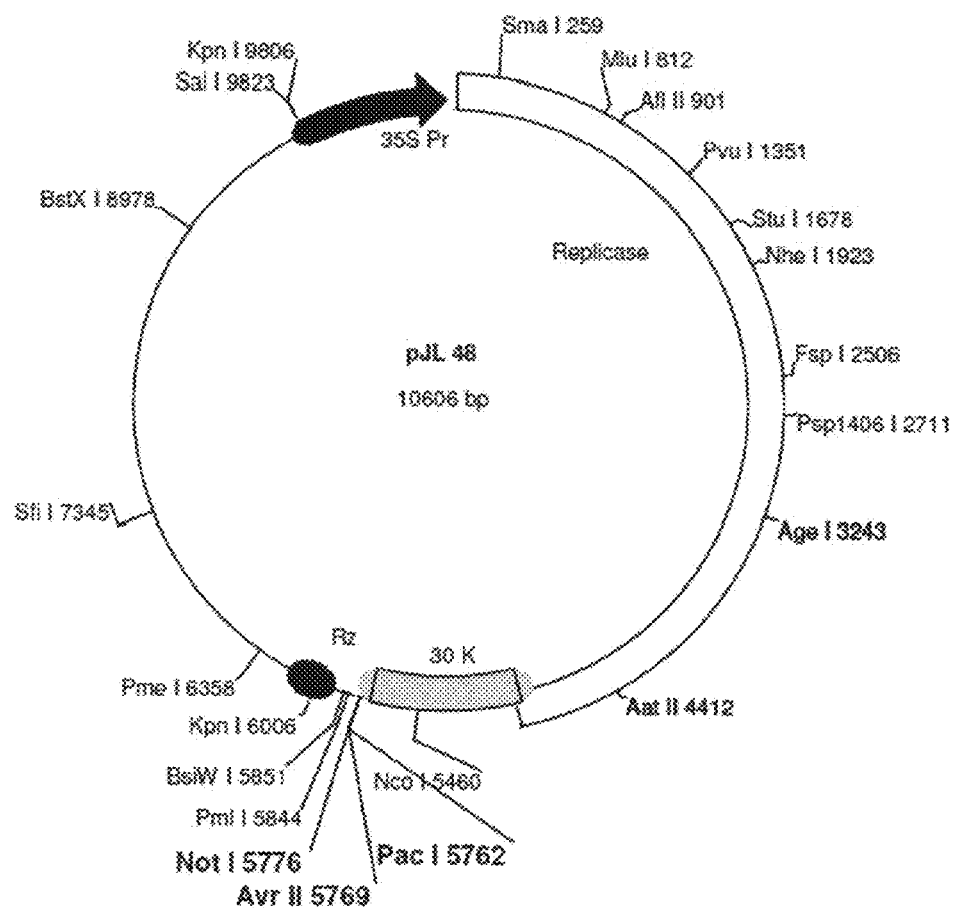
Figure 7A:
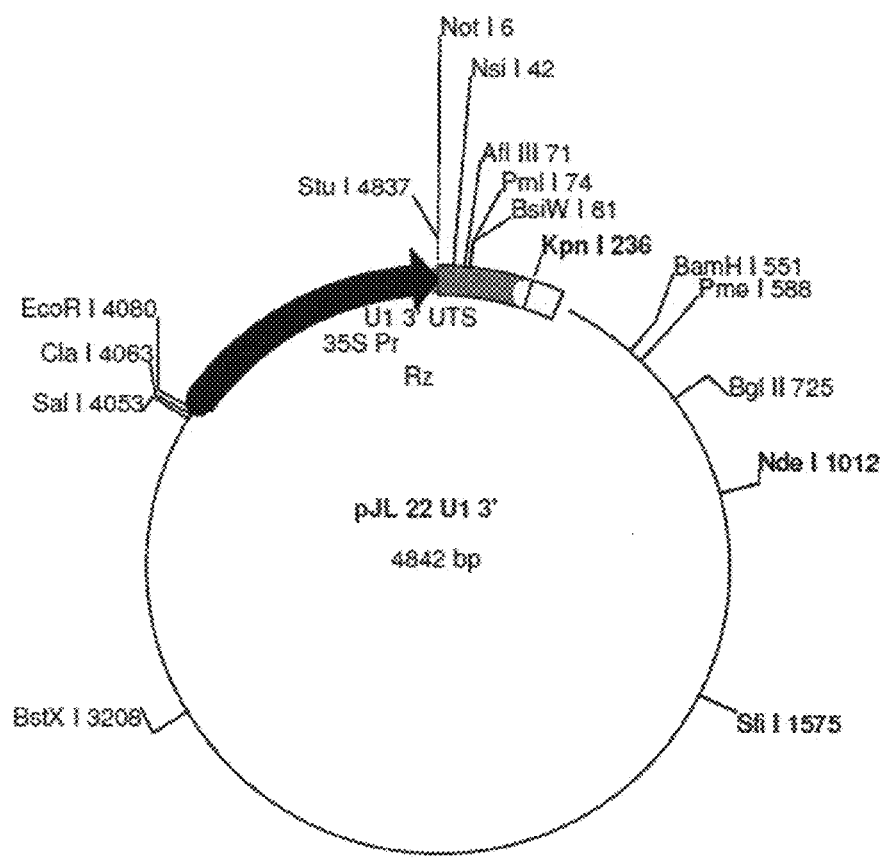
Figure 7A:
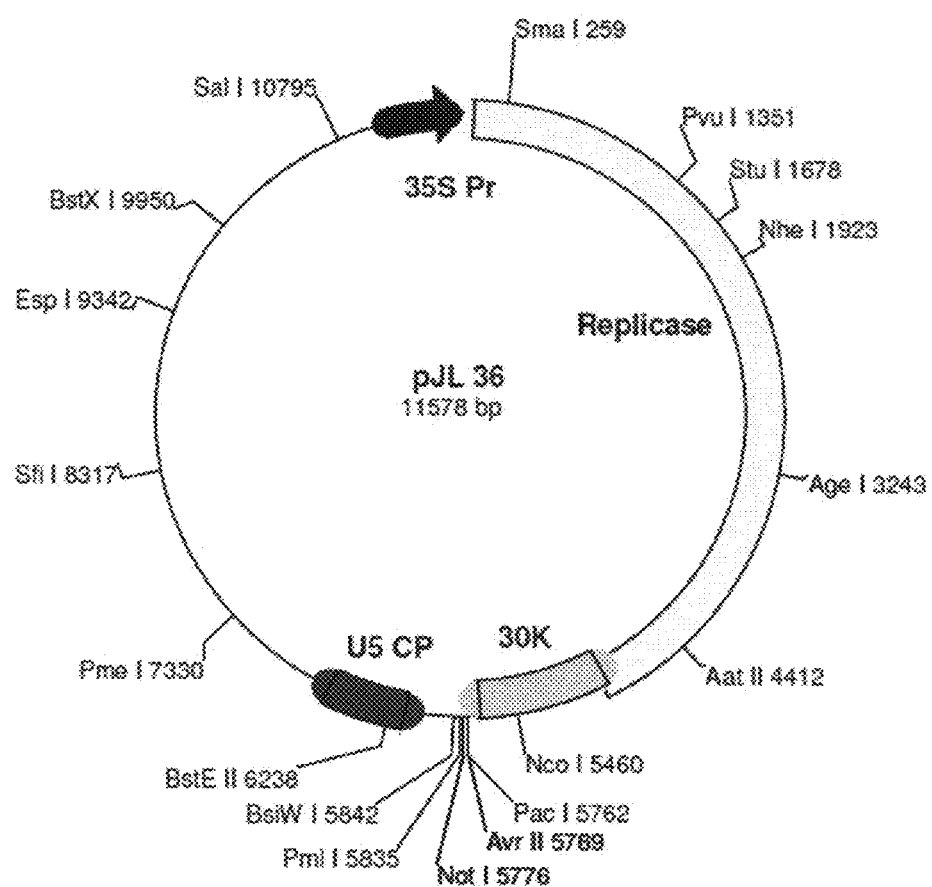

FIG. 7A: Plasmid maps of pJL22 U1 3', pJL36, and pJL48 (pJL-TRBO)=35S driven TMV expression vector in binary vector backbone. Clone is lacking a CP orf and is capable of high-level expression of protein in plants. T-DNA borders not shown in map. Construction: vector backbone=pJL36 NotI-SfiI cut. Insert=1.5 kb NotI-SfiI fragment of pJL 22 U1 3'.

FIG. 7B: DNA Sequence of pJL48 (pJL-TRBO) expression vector [SEQ ID NO: 13]. Nt 1=first nt of TMV U1 strain. PacI (TTAATTAA), AvrII (CCTAGG) and NotI (gcggccgc) sites for cloning. After NotI site, U1 nts 6177 to 6396 (number according to Goelet et al 1982, Proc. Natl. Acad. Sci.) Vector has No CP gene, and is composed only of TMV U1 strain sequences, and other (non-viral) sequences for cloning, etc.

Figure 8:
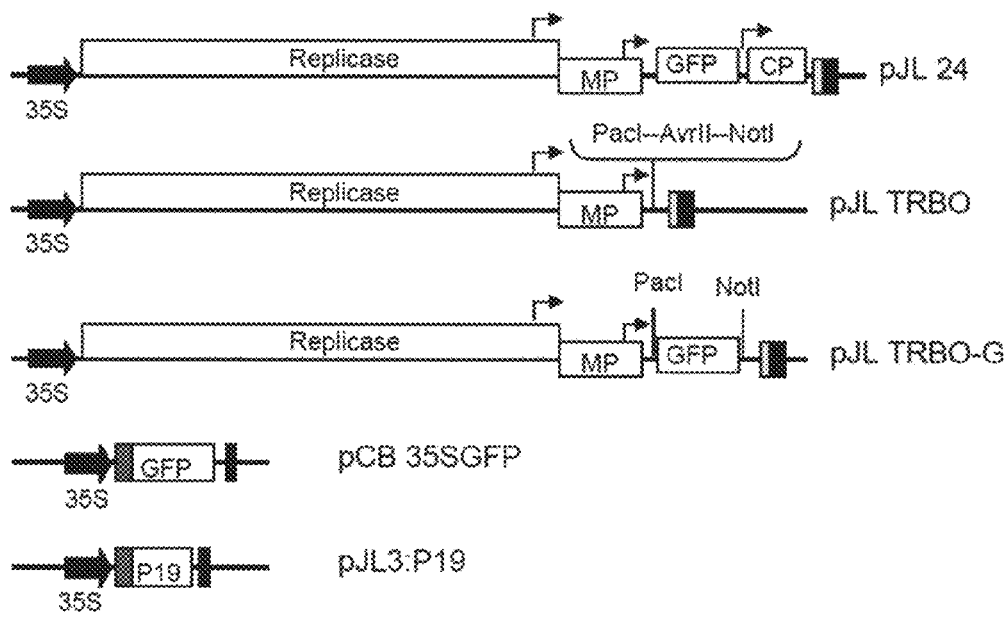

FIG. 8: Maps of plasmids used in Example II. The T-DNA regions of binary plasmids used in this example are represented. Cauliflower mosaic virus (CaMV) duplicated 35S promoter (block arrow), CaMV polyA signal sequence/terminator (black box). TEV 5' non-translated leader sequence (dark gray box); Ribozyme (light gray box); Bent arrows, subgenomic promoters. Open reading frames (ORFs) are represented by open boxes. Identities of ORFs are labeled in open boxes. Replicase; TMV 126K1183K orf; MP, movement protein; CP, coat protein; GFP, green fluorescent protein; P19, 19 kDa RNA silencing suppressor gene from tomato bushy stunt virus.

Figure 9:
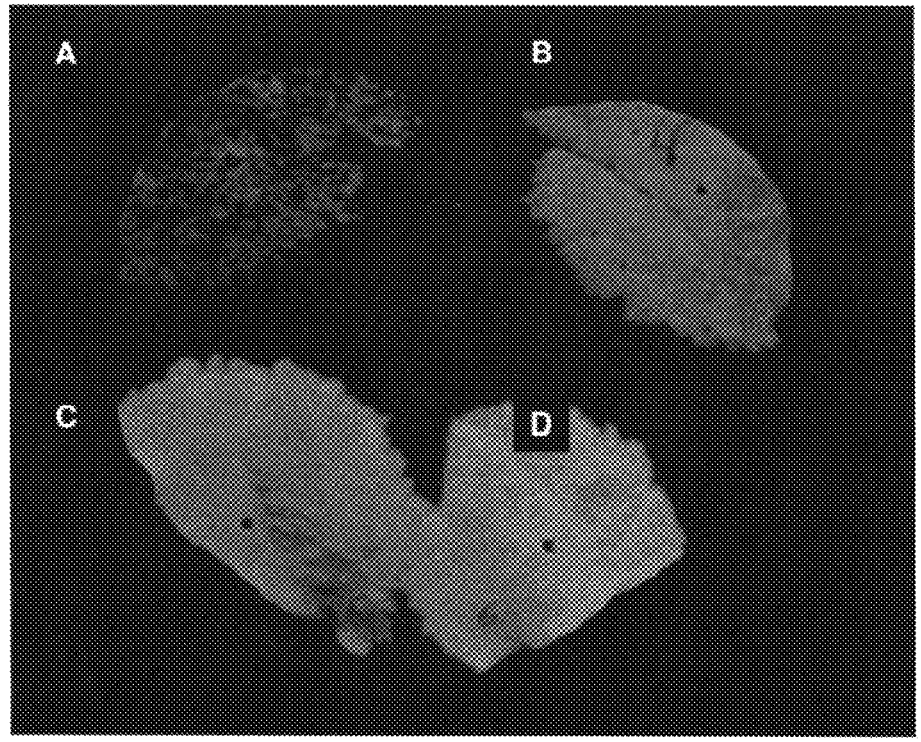

FIGS. 9A-9D: Comparison of agroinfection efficiency of pJL24 and pJL-TRBO vectors. T-DNAs of TMV-based expression vectors were introduced into *N. benthamiana* by agroinfection. Sections of an *N. benthamiana* leaf were infiltrated with *Agrobacterium tumefaciens* (A.t) cell suspensions transformed with plasmids as follows: FIG. 9A, A.t/pJL24 ($OD_{600}$ 1.0); FIG. 9B. Mixture of A.t./pJL24+A.t./pJL3:p19 (each at final $OD_{600}$ of 0.5); FIG. 9c. A.t./pJL-TRBO-G ($OD_{600}$ 1.0); FIG. 9D. Mixture of A.t./pJL-TRBO-G+A.t./pJL3:p19 (each at final $OD_{600}$ of 0.5). Photo taken under UV illumination 4 days post infiltration. In greyscale, GFP fluorescence appears as a light color.

Figure 10A:
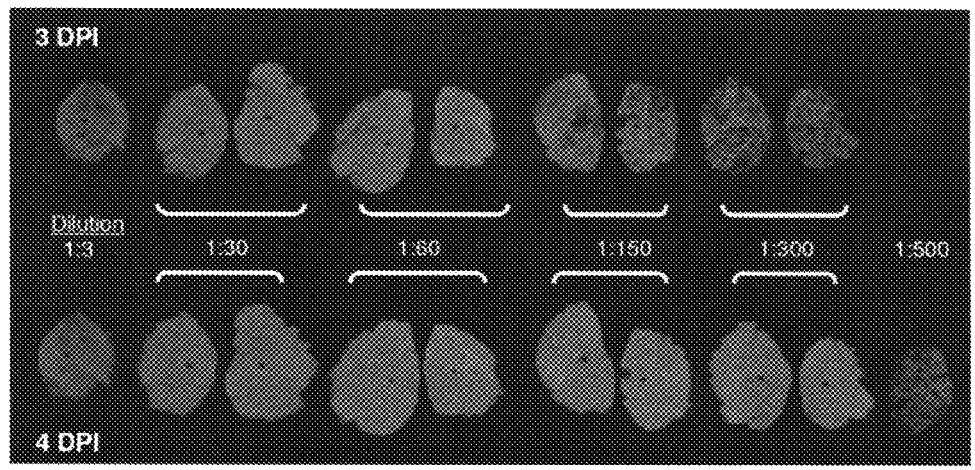
Figure 10B:
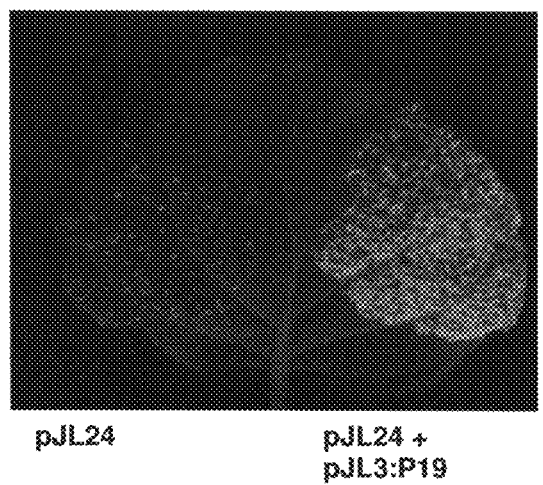

FIGS. 10A and 10B: Effect of *A. tumefaciens* (A.t.) cell density on agroinfection of plants with pJL-TRBO expression vector. Leaves of *N. benthamiana* plants were infiltrated with A.t. cell suspensions transformed with various binary (modified Ti) plasmids. A.t. cell suspensions were diluted, as noted in figure, from an initial $OD_{600}$ of 1.0.

FIG. 10A. Individual leaves infiltrated with A.t./pJL-TRBO-G cell suspensions were photographed under UV illumination at 3 and 4 days post infiltration (DPI) as noted.

FIG. 10B. Left half of leaf infiltrated with 1:100 dil of A.t./pJL24. Right half of leaf infiltrated with a mixture of 1:100 dil of A.t./pJL24 and 1:10 dil of A.t./pJL3:P19. Photo taken under UV illumination 3 DPI.

Figure 11A:
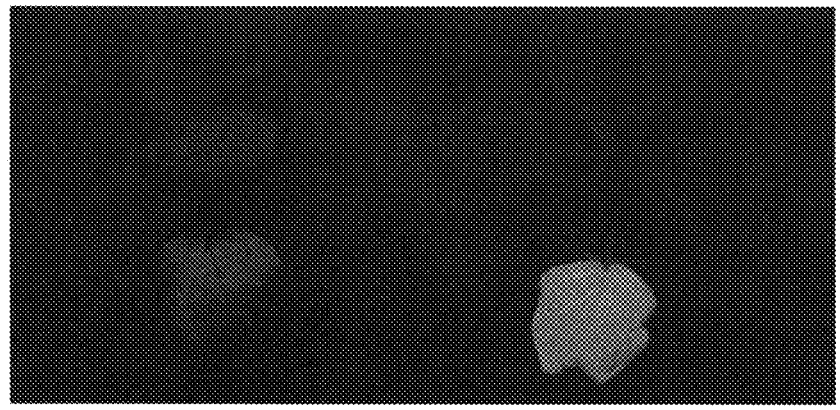
Figure 11B:
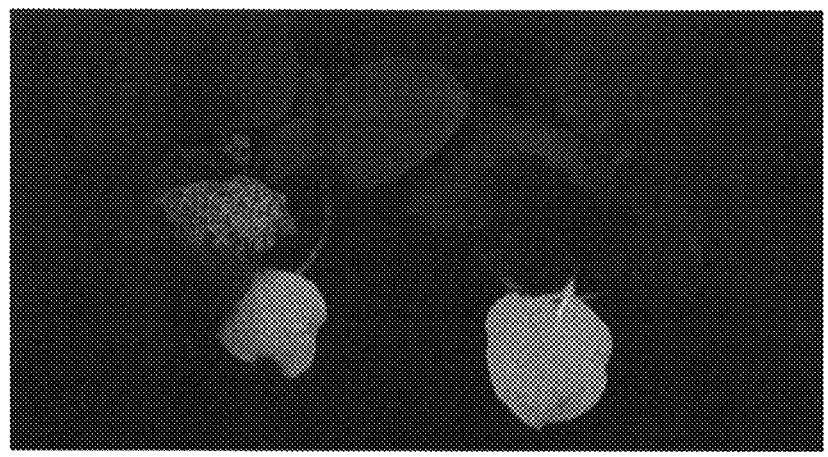
Figure 11C:

FIGS. 11A-11C: JL-TRBO-G replicon does not move systemically in plants. One leaf of an *N. benthamiana* plant was infiltrated with *A. tumefaciens* carrying pJL24 or pJL-TRBO-G plasmids. Plants were photographed under UV light to visualize the GFP expressed by either expression vector. Abbreviations used: DPI, days post infiltration.

Figure 12:
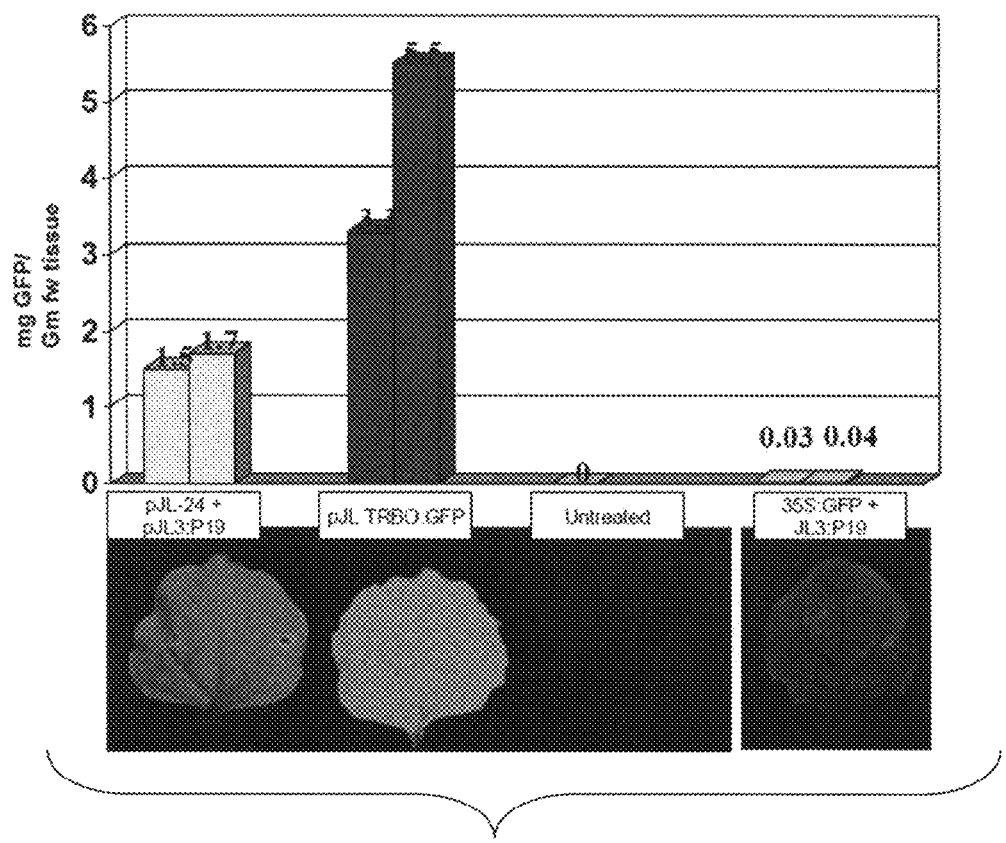

FIG. 12: Quantitative analysis of GFP expression levels from TMV vectors JL-24 and JLTRBO. Leaves of *N. benthamiana* were infiltrated with *A. tumefaciens* cells transformed with plasmids identified in figure. Bottom: images of individual infiltrated leaves photographed under UV illumination at 4 DPI. Top: Quantitation of GFP fluorescence activity levels in extracts prepared from infiltrated leaves six days post infiltration. Extracts were analyzed by a plate-based GFP fluorescence assay. Purified recombinant His6-tagged GFP (6×His tag disclosed as [SEQ ID NO: 19]) was used to generate a standard curve. Results are presented in micrograms GFP produced per gram of infiltrated tissue.

Figure 13:
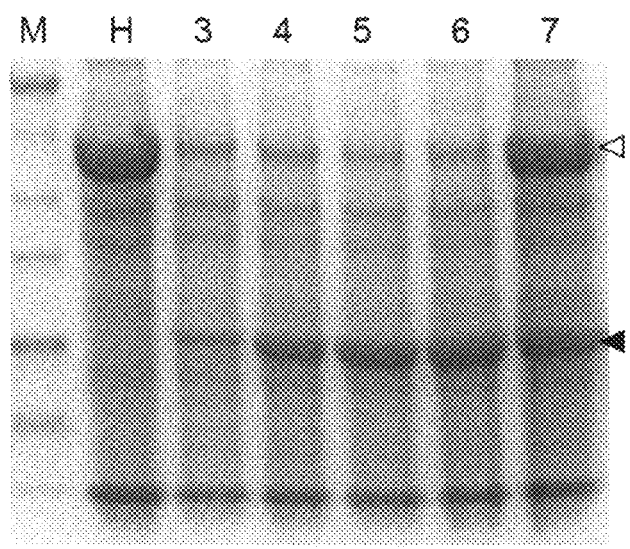

FIG. 13: GFP expression from JL-TRBO vector. *N. benthamiana* leaves were infiltrated with *A. tumefaciens* cultures transformed with pJL-TRBO-G. Total protein extracts were prepared from infiltrated leaf tissue from 3 to 7 days post infiltration (DPI). Equal volumes of extracts were analyzed by SDS-PAGE followed by staining with Coomassie blue. Location of TRBO-expressed GFP is noted by filled arrowhead. Amount of Rubisco large subunit protein (open arrowhead) is greatly reduced in 3 to 6 DPI samples because they were subjected to a freeze-thaw. MW's of protein standards (in kDa) are noted at left of image. Lanes: M, MW marker; H, healthy plant extract; 3-7 extracts from JL-TRBO-G infiltrated leaves 3-7 DPI, respectively.

Figure 14A:
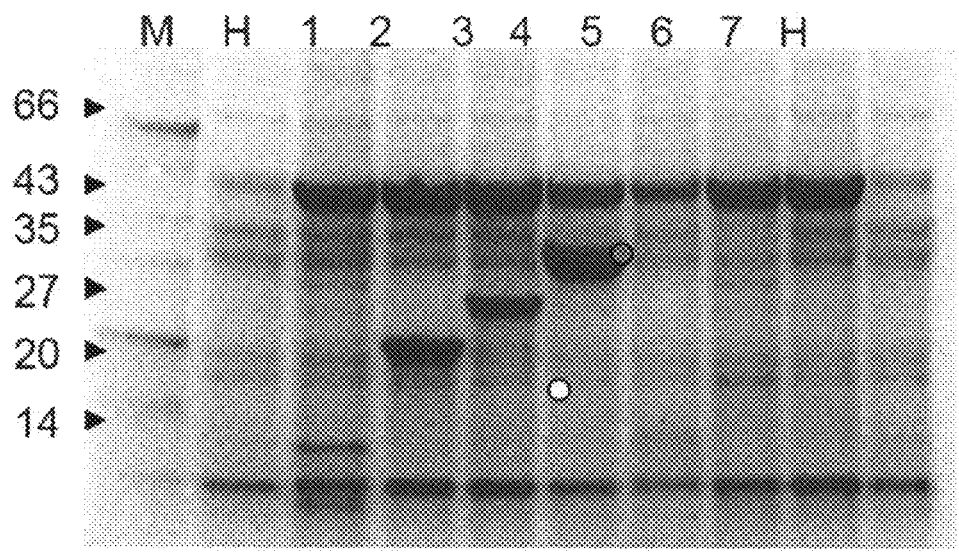
Figure 14B:
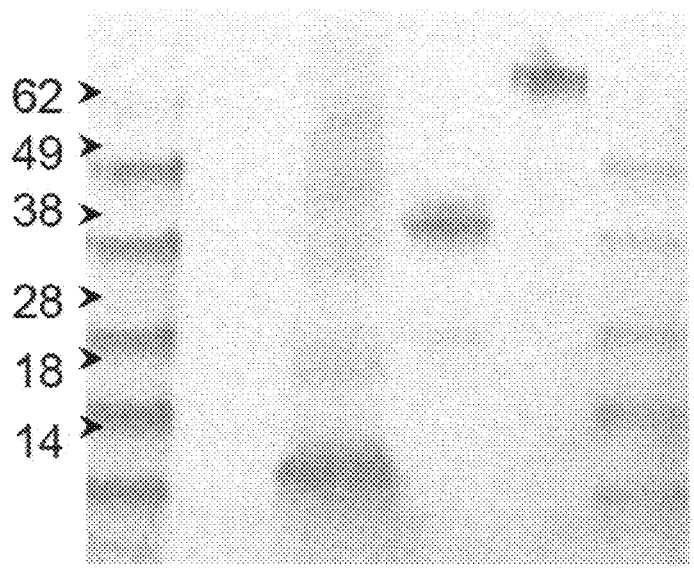

FIGS. 14A and 14B: Expression of various proteins from the JL-TRBO vector. *N. benthamiana* leaves were agroinoculated with JL-TRBO vectors expressing various genes. Total soluble protein extracts were prepared ca. 5 days post inoculation (DPI). Equal volumes of extract were loaded per lane. In some cases proteins were expressed as fusions to a peptide tag of His-6-Hemaglutinin peptide (6×His tag disclosed as [SEQ ID NO: 19]) (duplicated), $H_6HA_2$.

FIG. 14A: Coomassie blue stained SDS-PAGE gel of extracts.

FIG. 14B: Western (immuno-) blot analysis of extracts using anti-HA peptide primary antibody. Lanes: M, Molecular weight marker; $M_2$, See Blue molecular weight marker; H=healthy plant extract; Extracts from tissue infected with JL-TRBO vector expressing the following genes: 1, *Phytopthora infestans* Avr3a; 2, *Aequorea victoria* GFP; 3, GFP-$H_6HA_2$ fusion; 4, *A. thaliana* Adenosine Kinase; 5, $10^{th}$ type III (FN10) domain from human fibronectin; 6 *L. esculentum* RCR-3 proteinase; 7, *L. esculentum* P69b proteinase. White and grey circles denote location of FN10 and RCR-3 proteins on Coomassie blue stained gel, respectively.

Figure 15A:
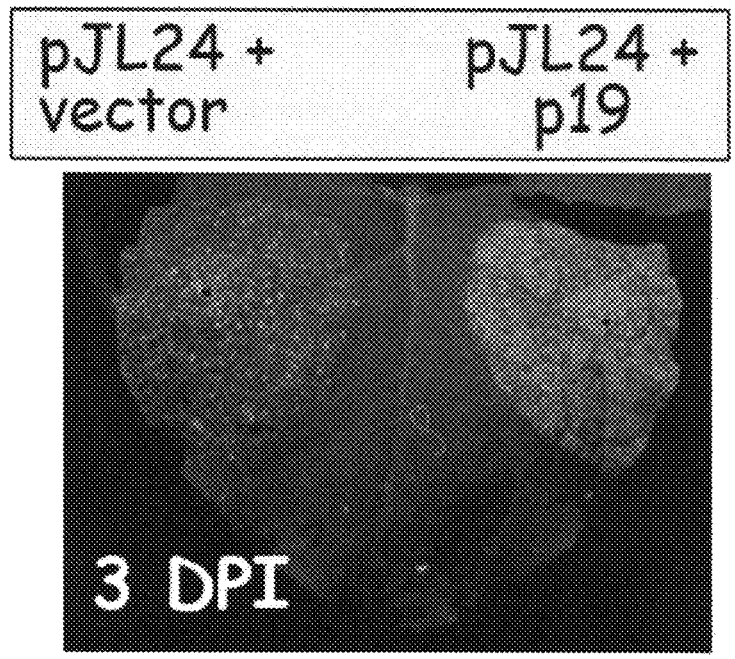

FIG. 15A: a photograph, taken at 3 DPI, showing agroinfection with pJL24+ vector, left image, and with pJL24+p19, right image; pJL24=35S:TMV:GFP.

Figure 15B:
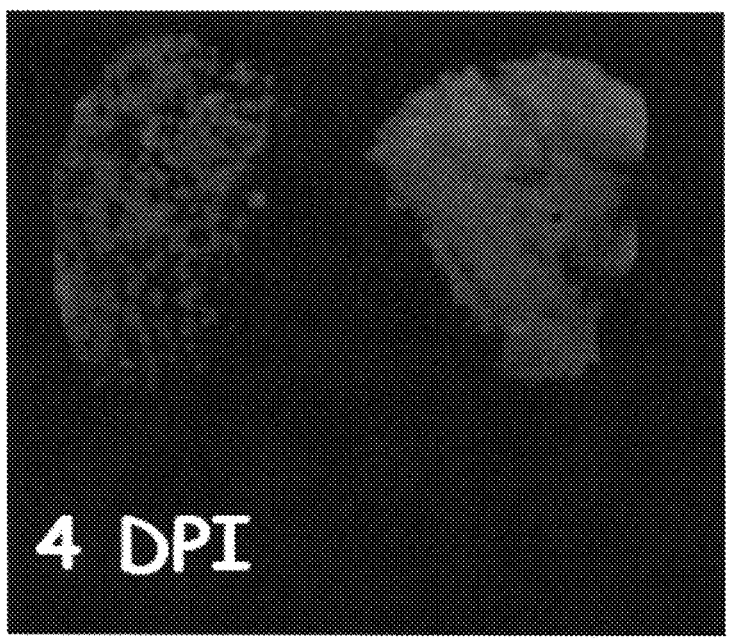

FIG. 15B: a photograph, taken at 4 DPI, showing agroinfection with pJL24+ vector, left image, and with pJL24+p19, right image; pJL24=35S:TMV:GFP.

FIG. 16A: a photograph, taken under fluorescent light at 4 DPI, showing agroinfection with pJL24+vector, left image, and with pJL24+p19, right image; pJL24=35S:TMV:GFP.

FIG. 16B: a photograph at 0.01 mm, taken under fluorescent light at 4 DPI, showing agroinfection with pJL24+vector, left image, and with pJL24+p19, right image.

FIG. 16C: SDS-PAGE showing that GFP is detectable by SDS PAGE in crude plant extracts.

Figure 17A:
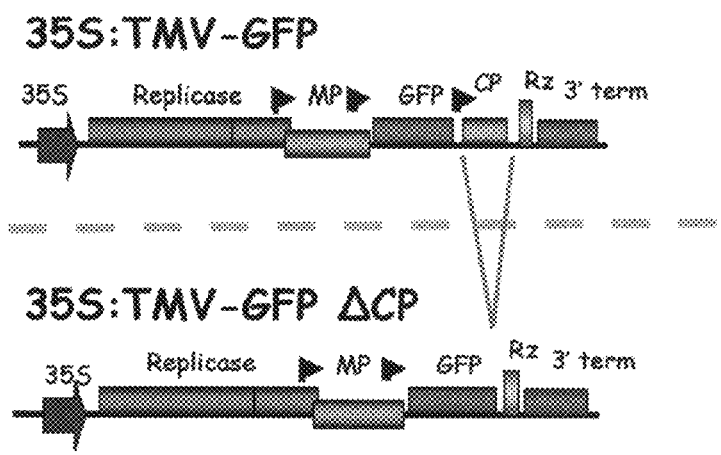

FIG. 17A: plasmid maps of pJL24=35S:TMV-GFP; and pJL48=pJL-TRBO=35S:TMV-GFP ΔCP [SEQ ID NO:13].

Figure 17B:
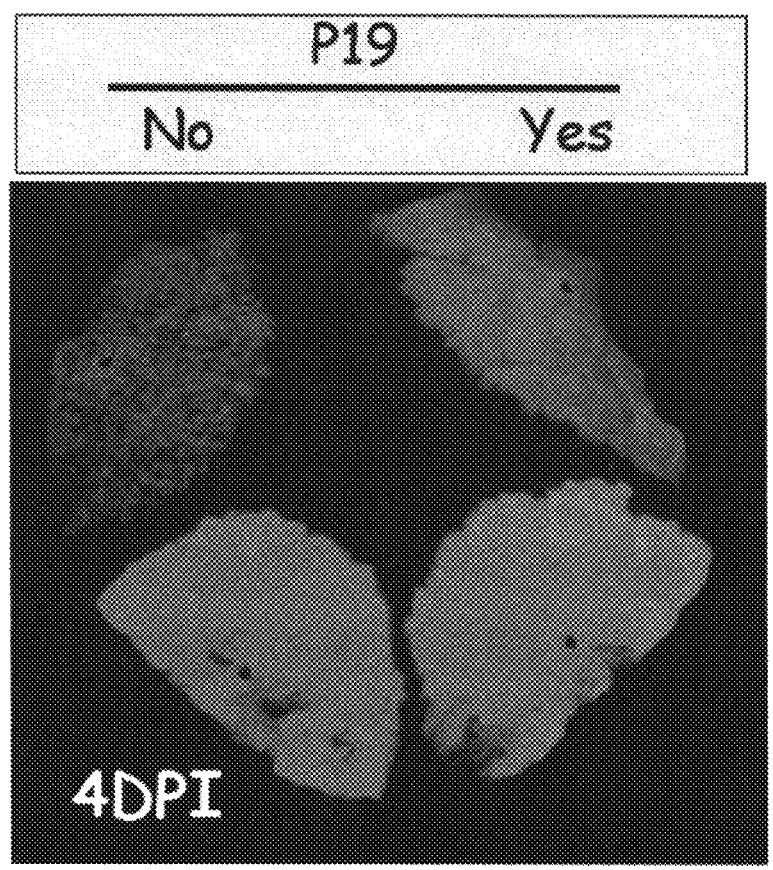

FIG. 17B: a photograph showing: upper left quadrant—35S:TMV-GFP with no p19; upper right quadrant—35S:TMV-GFP with p19; lower left quadrant—35S:TMV-GFP ΔCP with no p19; and, lower right quadrant—35S:TMV-GFP ΔCP (aka pJL48-G, aka pJL-TRBO-G) with p19.

Figure 18:
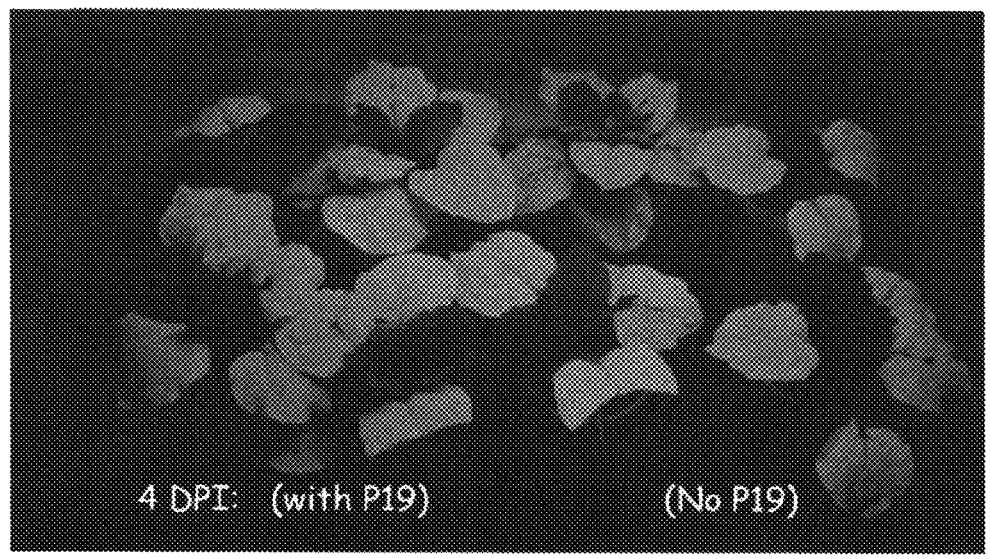

FIG. 18: a photograph showing *N. benthamiana* leaves infiltrated with 1:50 dilution of Agro/35S:TMV-GFP ΔCP.

Figure 19:
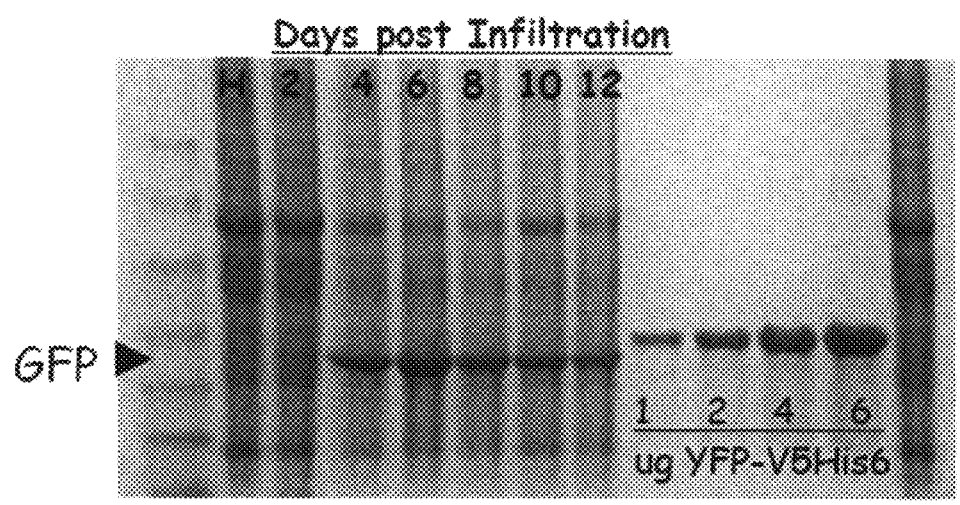

FIG. 19: shows the SDS-PAGE analysis of protein extract where plants were infiltrated with Agro/35S:TMV-GFP ΔCP, extracts were made at various times post infiltration, the SDS-PAGE was run with 50 µl protein/lane, and stained with Coomassie Blue.

FIG. 20: a photograph showing the comparison of protein expression vectors on the same leaf: 35S:GFP, in the upper left quadrant of the leaf; 35S:GFP+35S:p19, in the upper right quadrant; 35S:TMV:GFP+35S:p19, in the lower left quadrant; and 25S:TMV:GFP ΔCP+35S:p19, in the lower right quadrant.

FIG. 21A: a photograph, taken under white light, showing protoplasts were generated from pJL48 (pJL-TRBO):GFP infiltrated *N. benthamiana* leaf, showing protoplasts made 6 DPI, 2.5 hour digest in enzyme solution.

FIG. 21B: a photograph, taken under UV light, showing protoplasts were generated from pJL48 (pJL-TRBO):GFP infiltrated *N. benthamiana* leaf, showing protoplasts made 6 DPI, 2.5 hour digest in enzyme solution.

FIG. 22: pJL66 DNA sequence [SEQ ID NO:14] which includes a 35S driven DNA encoding for a replicon comprised of sequences from the U1 and U5 strains of TMV in a binary vector backbone, where the replicon generated from the transcription of pJL66 is lacking a CP off.

Figure 23:
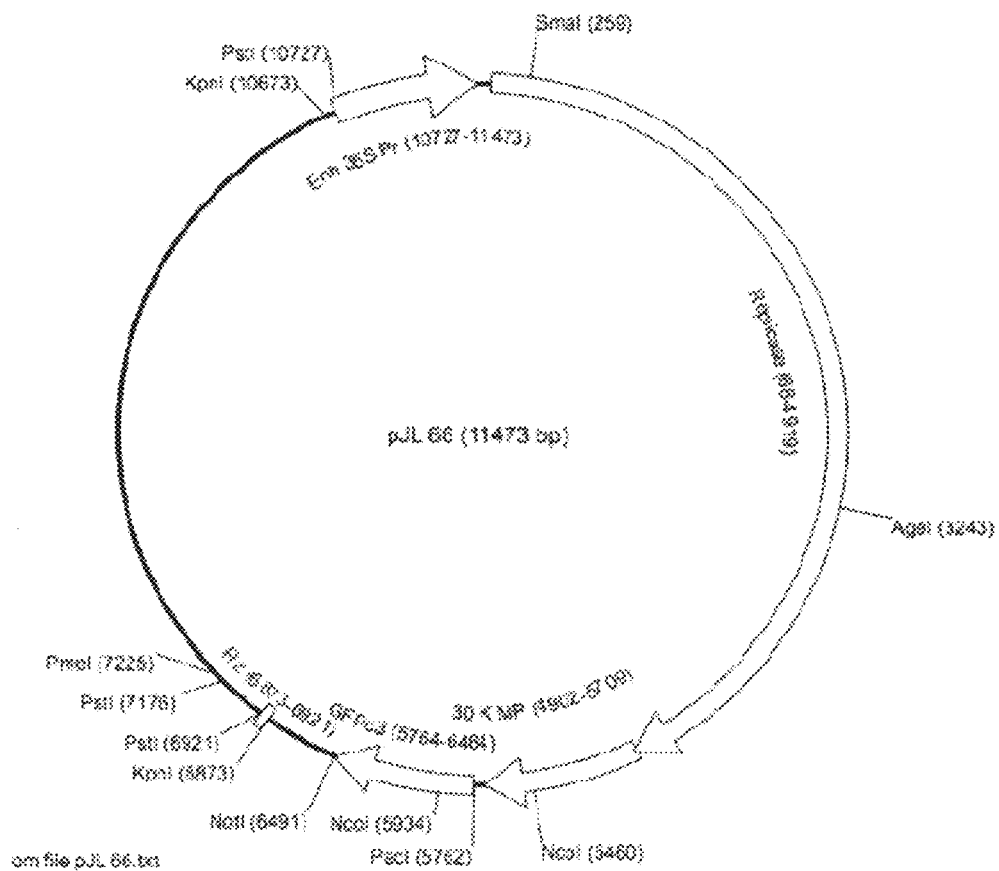

FIG. 23: pJL66-Binary vector, Kan resistance, T-DNA borders not shown in map. pJL66 is a deletion mutant of pJL24. All sequences downstream of GFP stop codon to last 4 codons of U5 CP were deleted from pJL24.

Figure 24:
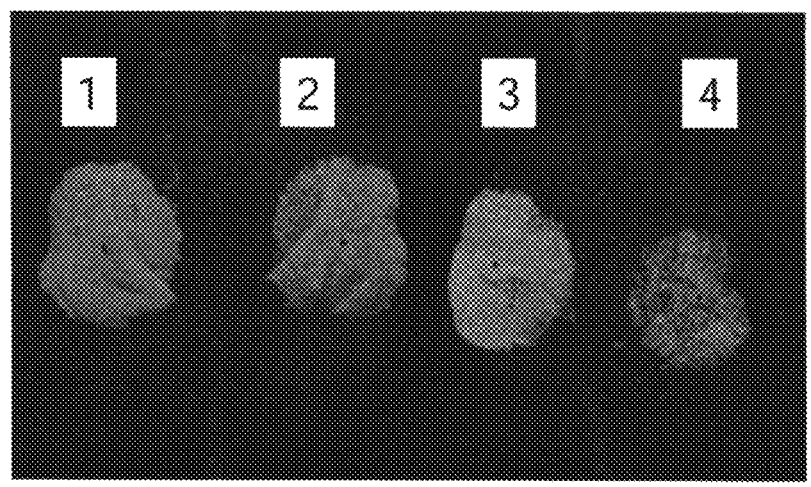

FIG. 24: photographs of plants infected with the TMV vector encoded in pJL66 via agroinfiltration/agroinfection.

DETAILED DESCRIPTION OF THE PREFERRED EMBODIMENT

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains. For example, the general teaching for constructing viral plant vectors and using them to infect plants and express heterologous proteins therefrom is disclosed in the references cited herein, the entire disclosures of which are hereby incorporated herein by reference.

As used in the specification and claims, the singular form "a", "an" and "the" include plural references unless the context clearly dictates otherwise. For example, the term "a cell" includes a plurality of cells, including mixtures thereof.

A "host" encompasses a cell, tissue or organism capable of being infected by and capable of replicating a nucleic acid such as a plant viral nucleic acid and which is capable of being infected by a virus containing the viral vector or viral nucleic acid. As used herein, host is intended to include generally whole plant, plant protoplast, plant cell, and plant tissues, plant organ or plant part such as root, stem leaf, flower or seed. This term is intended to include prokaryotic and eukaryotic cells, organs, tissues, organisms, or in vitro extracts thereof, where appropriate. One preferred host cell is a plant cell.

Providing a plant cell with the DNA sequences of the present invention is not limited to any particular method for transforming plant cells and tissues. In addition to virus-mediated transient expression of non-integrating DNA, the invention includes stably integrating the DNA of the invention into the genome of a plant cell to effect expression of the RNA replicon. Technology for introducing DNA into plant cells is well-known to those of skill in the art. Four basic methods for delivering foreign DNA into plant cells have been described, all of which are consistent with the methods of the present invention. Chemical methods (Graham and van der Eb, *Virology*, 54(02):536-539, 1973; Zatloukal, Wagner, Cotten, Phillips, Plank, Steinlein, Curiel, Birnstiel, *Ann. N.Y. Acad. Sci.*, 660:136-153, 1992); Physical methods including microinjection (Capecchi, *Cell*, 22(2):479-488, 1980), electroporation (Wong and Neumann, *Biochim. Biophys. Res. Commun.* 107(2):584-587, 1982; Fromm, Taylor, Walbot, *Proc. Natl. Acad. Sci. USA,* 82(17):5824-5828, 1985; U.S. Pat. No. 5,384,253), WHISKERS (U.S. Pat. Nos. 5,302,523 and 5,464,765), and biolistics (aka "the gene gun") (Johnston and Tang, *Methods Cell. Biol.,* 43(A):353-365, 1994; Fynan, Webster, Fuller, Haynes, Santoro, Robinson, *Proc. Natl. Acad. Sci. USA* 90(24):11478-11482, 1993); Viral methods (Clapp, *Clin. Perinatol.,* 20(1):155-168, 1993; Lu, Xiao, Clapp, Li, Broxmeyer, *J. Exp. Med.* 178(6):2089-2096, 1993; Eglitis and Anderson, *Biotechniques,* 6(7):608-614, 1988; Eglitis, Kantoff, Kohn, Karson, Moen, Lothrop, Blaese, Anderson, *Avd. Exp. Med. Biol.,* 241:19-27, 1988); and Receptor-mediated methods (Curiel, Agarwal, Wagner, Cotten, *Proc. Natl. Acad. Sci. USA,* 88(19):8850-8854, 1991; Curiel, Wagner, Cotten, Birnstiel, Agarwal, Li, Loechel, Hu, *Hum. Gen. Ther.,* 3(2):147-154, 1992; Wagner et al., *Proc. Natl. Acad. Sci. USA,* 89 (13):6099-6103, 1992); *Agrobacterium*-Ti plasmid (White et al., *Plant Biotechnology* Kung and Arntzen eds. Butterworth Pub., Boston, Mass., 1989).

"Infection" includes the ability of a virus to transfer its nucleic acid to a host or the introduction of a viral nucleic acid into a host, such that the viral nucleic acid is replicated, viral proteins are synthesized. In this context, the terms "transmissible" and "infective" are used interchangeably herein. The term is also meant to include the ability of a selected nucleic acid sequence to integrate into a genome, chromosome or gene of a target organism.

The term "non-viral" is used here in a special sense to include any RNA segment which is not normally contained within the virus whose modification is exploited for effecting gene transfer and is therefore used synonymously with "exogenous". Therefore, a gene derived from a different virus species than that modified is included within the meaning of the terms "non-viral" and "exogenous" for the purposes of describing the invention. For example, a non-viral gene as the term is used herein could include a gene derived from a bacterial virus, an animal virus, or a plant virus of a type distinguishable from the virus modified to effect transformation. In addition, a non-viral gene may be a structural gene derived from any prokaryotic or eukaryotic organism.

It will be understood by those ordinarily skilled in the art that there may exist certain genes whose transfer does not result in obvious phenotypic modification of the host cell. A phenotypic modification may occur, for example, if the translation product of the non-viral gene is toxic to the host cell, is degraded or processed in a manner which renders it non-functional or possesses structural features which render it impossible for the host cell to translate in sufficient quantities to confer a detectable phenotype on the transformed cells. However, the invention does not depend upon any specific property of an RNA segment or gene being transferred. Therefore, the possible existence of RNA segments or genes which fail to confer a readily observable phenotypic trait on recipient cells or plants is not relevant to the invention and, in any case, will be readily recognizable by those of ordinary skill in the art without undue experimentation.

"Phenotypic Trait" is an observable, measurable or detectable property resulting from the expression or suppression of a gene or genes. Phenotype includes both easily observable traits and biochemical processes.

"Plant Cell" is the structural and physiological unit of plants, consisting of a protoplast and the cell wall. "Plant Organ" is a distinct and visibly differentiated part of a plant, such as root, stem, leaf or embryo. "Plant Tissue" is any tissue of a plant in planta or in culture. This term is intended to include a whole plant, plant cell, plant organ, protoplast, cell culture, or any group of plant cells organized into a structural and functional unit. "Protoplast" is an isolated cell without cell walls, having the potency for regeneration into cell culture, tissue or whole plant.

"Promoter" is the 5'-flanking, non-coding sequence substantially adjacent a coding sequence which is involved in the initiation of transcription of the coding sequence.

The terms "nucleic acid sequence", "polynucleotide", "nucleotides" and "oligonucleotides" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

A "gene" refers to a polynucleotide containing at least one open reading frame that is capable of encoding a particular polypeptide sequence after being transcribed and translated.

"Expression" refers to the process by which a polynucleotide is transcribed into mRNA and/or the process by which the transcribed mRNA (also referred to as "transcript") is subsequently being translated into peptides, polypeptides, or proteins. The transcripts and the encoded polypeptides are collectedly referred to as gene product. If the polynucleotide is derived from genomic DNA, expression may include splicing of the mRNA in a eukaryotic cell.

"Exogenous RNA segment" describes a segment of RNA to be inserted into the virus RNA to be modified, the source of the exogenous RNA segment being different from the RNA virus itself. The source may be another virus, a living organism such as a plant, animal, bacteria, virus or fungus, the exogenous RNA may be a chemically synthesized RNA or it may be a combination of the foregoing. The exogenous RNA segment may provide any function that is appropriate and known to be provided by an RNA segment. Such functions include, but are not limited to, a coding function in which the RNA acts as a messenger RNA encoding a sequence which, translated by the host cell, results in synthesis of a peptide or protein having useful or desired properties. The RNA segment may also be structural, as for example in ribosomal RNA, it may be regulatory, as for example with small nuclear RNAs or anti-sense RNA, or it may be catalytic. An exogenous RNA segment can be a complete or partial coding sequence.

It is to be understood that various aspects of the method described herein can be modified as needed, depending upon specific aspects of the virus selected as the transforming agent and of the RNA segment to be inserted. For example, if the inserted gene is in the form of messenger-sense RNA to be directly translated by the transformed cell, the gene must be free of intervening, nontranslated sequences, such as introns. On the other hand, the inserted gene need not be a naturally occurring gene, but it may be modified, it may be a composite of more than one coding segment, or it may encode more than one protein. Combining insertions and deletions in order to control the total length or other properties of the modified RNA molecule may also modify the RNA. The inserted non-viral gene may be either prokaryotic or eukaryotic in origin as long as it is in a form, which can be directly translated by the translation machinery of the recipient cell. Eukaryotic genes containing introns within the coding sequence must therefore be inserted in the form of a cDNA copy of the eukaryotic messenger RNA encoding the gene. The inserted gene may contain its own translation start signals, for example, a ribosomal binding site and start (AUG) codon, or it may be inserted in a manner which takes advantage of one or more of these components preexisting in the viral RNA to be modified. Certain structural constraints must be observed to preserve correct translation of the inserted sequence, according to principles well understood in the art. For example, if it is intended that the exogenous coding segment be combined with an endogenous coding segment, the coding segment to be inserted must be inserted in reading frame phase therewith and in the same translational direction.

In a broad aspect, there is described herein plasmids that include a 35S promoter driven version of the TMV expression vector "30BGFP" which was constructed in the T-DNA region of the mini-binary vector pCB301. This plasmid was then modified to contain rare restriction endonuclease sites for standard restriction enzyme based cloning approaches.

The 35S driven TMV vector was also modified to be compatible with a novel and rapid cloning method. In this method PCR products were directly cloned into a specially designed TMV vector, without the need for digesting PCR products with restriction enzymes. Two SapI type IIS restriction enzyme sites were inserted into the TMV cDNA in the binary vector. SapI cuts outside of its recognition sequence to leave 5' overhangs of 3 nucleotides. The two SapI sites were engineered to generate G/C rich 5' overhangs after digestion. PCR primers were designed with short, 5' G/C rich 'clamps' complementary to the sticky ends of the SapI cut vector. Purified PCR products were treated with a proofreading DNA polymerase in the presence of dATP and dTTP to generate 5' GC rich sticky ends on the PCR product. As described herein, in order to reflect that sticky ends were generated in a restriction enzyme independent manner, this method is called "sticky RICE" (Restriction enzyme Independent Cohesive Ends). The sticky RICE method allows for directional cloning of PCR products in 30 minutes with cloning efficiencies approaching 90%, and does not use expensive recombinase or topoisomerase enzymes.

It is to be understood that modification of the TMV vector to be compatible with sticky RICE cloning thus enables the cloning of a PCR product regardless of the restriction enzyme sites that may be present in the PCR product. This simplifies PCR primer design and is particularly useful when cloning DNA sequences in which the complete DNA sequence is not known.

In one particular aspect, it is described herein that the TMV vectors constructed all reliably infect Nicotiana bentharniana plants by the standard agroinfection procedure. It was determined that co-expression of a suppressor of RNA silencing dramatically increases the infection efficiency of the 35S driven TMV vector construct.

The co-introduction of a 35S-driven TMV:GFP vector and an RNA silencing suppressor gene resulted in GFP expression in nearly every cell in the infiltrated tissue by 3 days post infiltration. This high transfection efficiency makes it possible to recover high levels of recombinant GFP from the Agroinfiltrated tissue itself. This result further extends the utility of the TMV expression vector system.

The cloning and/or Agroinfection procedure methods described herein can be readily applied to other cloning and expression vector systems and are especially amenable to high-throughput cloning workflows. These improved methods also make it easier and more cost effective to use TMV-based plant expression vectors.

The vectors, cloning methods and efficient agroinfection procedures described herein represent a significant advance in both cloning genes into a TMV expression vector and in infecting plants with recombinant TMV expression vectors. The improvements in the cloning methods and in the infection of plants are significantly less costly than alternative strategies and are highly efficient, scalable and require less hands-on time than previous approaches. The present TMV expression vector system now allows for the more effective use of TMV expression vectors since the TMV expression vectors are now faster, more reliable and easier to use than prior strategies. In addition, the present TMV expression vector system presented herein can also be used to improve other expression and cloning vector systems.

It is to be understood that the vectors can be introduced into a plant cell by one or more of hand inoculations where drops of the preparation are put onto a surface of a leaf and gently rubbed; mechanized inoculations of plants where plant bed inoculations are performed by spraying the vector solution onto the plants (which can have cut leaves); high pressure spray of single leaves which provides single plant inoculations by spraying the leaves with a narrow, directed spray; and vacuum infiltration where the inoculations may be accomplished by subjecting a host organism to a substantially vacuum pressure environment in order to facilitate infection.

Various suitable assays can be used to determine expression of the transgene. For example, non-limiting examples include detecting and/or quantifying the presence of transcribed sense or anti-sense strands of the transgene by conventional hybridization assays (e.g. Northern blot analysis), amplification procedures (e.g. RT-PCR), and array-based technologies. Expression of the transgene can also be determined by examining the protein product. A variety of techniques are available in the art for protein analysis. Non-limiting examples include radioimmunoassays, ELISA (enzyme linked immunoradiometric assays), "sandwich" immunoassays, immunoradiometric assays, in situ immunoassays (using e.g., colloidal gold, enzyme or radioisotope labels), western blot analysis, immunoprecipitation assays, immunofluorescent assays, and SDS-PAGE. It is to be generally understood that determining the protein level involves (a) providing a biological sample containing polypeptides; and (b) measuring the amount of any immunospecific binding that occurs between an antibody reactive to the transgene product and a component in the sample, in which the amount of immunospecific binding indicates the level of expressed proteins. Antibodies that specifically recognize and bind to the protein products of the transgene are required for immunoassays. These may be purchased from commercial vendors or generated and screened using methods well known in the art. The sample of test proteins can be prepared by homogenizing the eukaryotic transformants (e.g. plant cells) or their progenies made therefrom, and optionally solubilizing the test protein using any suitable detergents. Results obtained using any such assay on a sample from a plant transformant or a progeny thereof is compared with those from a non-transformed source as a control.

'In a broad aspect, there is provided herein a process for expressing a sequence of interest in a plant cell, including a plant, plant part, or plant cell culture. The process includes providing a cell with a DNA sequence comprised of: i) a DNA sequence encoding an RNA replicon operably linked to a plant-functional promoter (capable of initiating transcription in a plant cell), and ii) a sequence of interest.

The sequences encoding the RNA replicon are derived from a plant virus. The RNA replicon generated by transcription of the DNA sequence is not a full-length virus sequence, but is deleted of certain virus sequences. The absence of these virus sequences causes an increased frequency of replicon formation compared to a full length virus RNA from which the replicon was derived. The process further includes causing the expression of the sequence of interest.

In one embodiment, the RNA replicon is derived from tobacco mosaic virus. In other embodiments, the RNA replicon is derived from a plant virus other than tobacco mosaic virus.

In a particular aspect, the RNA replicon can lack the coat protein gene sequence or at least lack a portion of the coat protein gene sequence.

In certain embodiments, the virus is lacking a sequence or sequences such that the lack of these sequences causes an increased frequency of replicon formation.

In a particular embodiment, the RNA replicon can be composed of RNA sequences from two different RNA viruses. In one embodiment, the RNA replicon is composed of RNA sequences from two different tobamoviruses. In another embodiment, the RNA replicon is composed of RNA sequences from the U1 and U5 strains of tobacco mosaic virus.

Also, in certain embodiments, the RNA replicon is not capable of systemically infected a host plant.

Also provided herein is a vector pJL48 (pJL-TRBO) which includes a 35S driven TMV expression vector in a binary vector backbone, where the replicon generated from the transcription of pJL48 (pJL-TRBO) is lacking a CP orf and is capable of expression of a desired product in plants. In one embodiment, the vector is substantially as shown in FIG. 7A and FIG. 8 and contains an inserted sequence of interest such that the sequence will be expressed from the RNA replicon derived from this DNA.

Also provided herein is a vector pJL66 [SEQ ID NO: 14] which includes a 35S driven DNA encoding for a replicon comprised of sequences from the U1 and U5 strains of TMV in a binary vector backbone, where the replicon generated from the transcription of pJL66 is lacking a CP orf.

In yet another aspect, there is provided herein a method for constructing pJL66 [SEQ ID NO: 14] which comprises deleting nucleotides 5788 to 6608 from pJL36.

In a particular aspect, there is provided herein a vector comprising the nucleotide sequence selected from the group consisting of: the nucleotide sequence as shown in SEQ ID NO:13; and a nucleotide sequence which encodes the same sequence of amino acids as encoded by the nucleotide sequence shown in SEQ ID NO: 13.

In a particular aspect, there is provided herein a vector comprising the nucleotide sequence selected from the group consisting of: the nucleotide sequence as shown in SEQ ID NOs: 15, 16, 17; and a nucleotide sequence which encodes the same sequence of amino acids as encoded by the nucleotide sequence shown in SEQ ID NOs: 15, 16, 17.

The host cell can comprise a whole plant, an isolated plant cell, or a protoplast. In certain embodiments, the plant host cell can comprise a natural host for *Agrobacterium*, and wherein introducing the replicon comprises performing *Agrobacterium*-mediated plant transformation. Also, in certain embodiments, the promoter can be the Cauliflower mosaic virus CaVM35S promoter. Thus, there is also provided herein a plant cell that is transformed with a vector as described herein.

In a particular aspect, there is provided herein an isolated nucleotide sequence of SEQ ID NO: 5.

In a particular aspect, there is provided herein an isolated nucleotide sequence of SEQ ID NO: 13.

In a particular aspect, there is provided herein an isolated nucleotide sequence of SEQ ID NO: 14.

In a particular aspect, there is provided herein an isolated nucleotide sequence of SEQ ID NOs: 15, 16, 17.

In a particular aspect, there is provided herein a method for recovering the product of an expressed gene of interest from a host cell, the method comprising: providing an expression vector comprising a promoter driven tobacco mosaic virus (TMV) vector, capable of non-systemically infecting a host cell, wherein the vector encodes the gene of interest; introducing the expression vector into the host cell to produce a transformed host cell; growing the transformed host cell under conditions suitable to effect transcription of the gene of interest; and recovering the product of the expressed gene of interest.

The method can include infecting the plants using one or more of agroinfiltration or agroinfection procedures. Also, the method can include introducing the vector by performing pressure infiltration of plant tissues, hand inoculation of a surface of a leaf, a mechanical inoculation of a plant bed, a high pressure spray of a leaf, or a vacuum infiltration.

In another aspect, there is provided herein a method for extracting at least one recombinant product produced from a TMV based vector from an agroinfiltrated tissue, without having causing any systemic viral vector movement.

In another aspect, there is provided herein a method for making pJL48 (pJL-TRBO) comprising: deleting a coat protein gene and 3' non-translated tobamovirus sequences in pJL36, and replacing the deleted sequences with nts 6177 to 6395 of TMV U1 strain.

In another aspect, there is provided herein plants infected with one or more of the TMV expression vector as in any of the preceding claims wherein the plant is infected by one or more of agroinfiltration or agroinfection procedures.

In another aspect, there is provided herein a method of agroinfection with pJL48 (pJL-TRBO) wherein co-expression of an RNA silencing suppressor is not needed.

In another aspect, there is provided herein a method of agroinfection with pJL48 (pJL-TRBO) wherein foreign protein expression levels from pJL48 (pJL-TRBO) are different than foreign protein expression levels from pJL36.

In another aspect, there is provided herein a pJL48 (pJL-TRBO) vector having no coat protein, wherein the pJL48 vector cannot move off an infiltrated plant, and cannot be easily/reliably transferred from one plant to another.

In another aspect, there is provided herein a method for agroinfection comprising using pJL48 (pJL-TRBO) in *Agrobacterium* cultures diluted 10, 20, 50 or 100 or more fold (from an initial culture OD 600 of 1.0).

In another aspect, there is provided herein a method for improving agroinfiltration frequency comprising: deleting the CP gene sequence and the viral 3' non translated sequences encoded in pJL36, and replacing the deleted sequences with TMV U1 nts 6177-6395.

In another aspect, there is provided herein a process for expressing a sequence of interest in a plant cell, including a plant, plant part, or plant cell culture, comprising: (A) providing a cell with a DNA sequence comprised of: i) a DNA sequence encoding an RNA replicon operably linked to a plant-functional promoter (capable of initiating transcription in a plant cell), and ii) a sequence of interest, wherein the sequences encoding the replicon are derived from a plant virus or plant viruses, (B) co-expressing in same plant cells a second sequence that causes an increased frequency of replicon formation compared to cells that do not express the second sequence; and (C) causing expression of said sequence of interest.

In one embodiment, the second sequence encodes for a protein that has RNA silencing suppression functions. In another embodiment, the second sequence encodes for the protein P19 from Tomato bushy stunt virus. In still another embodiment, the second sequence encodes for any gene from viral or cellular origins that has RNA silencing suppression functions.

Also, in certain embodiments, the sequence encodes for one or more of the following genes: PO protein gene from a polerovirus, HC-Pro protein gene from a potyvirus, CP from turnip crinkle or related viruses, P21 from beet yellows closterovirus.

In another aspect, there is provided herein a protein expression vectors (replicons) in plants comprising one or more of pJL36, pJL48 (pJL-TRBO), which are capable of expressing proteins in plants. In certain embodiments, the protein expression vector is useful for expressing proteins that can be used as pharmaceuticals, nutraceuticals, for research purposes, for diagnostic assays, enzymes for synthesis/industrial use enzymes. In certain embodiments, the protein can include (but is not limited to) proteins that are antibodies, or antibody fragments, enzymes, hormones, peptides.

In yet another broad aspect, there is provided herein derivatives of the vectors as described herein that enable high-level expression of secreted proteins in plants, or proteins targeted to various subcellular locations. In yet another broad aspect, there is provided herein use one or more such expression vectors in an agroinfiltration procedure to express multiple proteins in the same cell. In yet another broad aspect, there is provided herein use of a promoter driven version of a first gene of interest that is introduced into plant cells by agroinfiltration at the same time, or either before or after, introduction of the 35S promoter driven version of the pJL36 or pJL48 (pJL-TRBO) vectors expressing a second gene of interest.

In yet another broad aspect, there is provided herein a method for the expression of multiple recombinant proteins in the same plant cell comprising using one or more of the expression vectors of any of the preceding claims.

In yet another broad aspect, there is provided herein a method for expressing one or more genes of interest composed of multiple polypeptide chains, or producing more than one protein in a plant cell, where the method includes using one or more of the expression vectors of any of the preceding claims.

In yet another broad aspect, there is provided herein a modified pJL36 vector, wherein the Cauliflower mosaic virus '35S' promoter is substituted with one or more other promoters including natural promoters, non-natural/synthetic promoters, or combinations. In yet another broad aspect, there is provided herein a modified pJL48 (pJL-TRBO) vector, wherein the Cauliflower mosaic virus '35S' promoter is substituted with one or more other promoters including natural promoters, non-natural/synthetic promoters, or combinations. In certain embodiments, the promoters are inducible by temperature, other proteins, or chemicals/small molecules, as well as tissue-specific or constitutive promoters.

In yet another broad aspect, there is provided herein a method for cloning a vector, comprising: using mixtures of DNA polymerase and ligase (and, optionally, polynucleotide kinase) with specially designed vector and insert DNAs to directionally ligate DNAs.

In yet another broad aspect, there is provided herein a method for cloning a vector, comprising generating single stranded 3 nt, 5' overhangs on pJL43 by digestion the restriction endonuclease SapI (underlined); treating the pJL43 vector with phosphatase after digestion to remove phosphates from 5' ends of DNA.

In yet another broad aspect, there is provided herein a method for inserting a sequence into a DNA. The method includes: using a directional one-step cloning method where two SapI restriction endonuclease recognition sites are inserted into the vector cDNA sequence, and where the SapI sites are designed so that 5' single stranded overhangs are maintained in the SapI cut vector in the presence of T4 DNA polymerase and dATP and dTTP.

In certain embodiments, PCR products are amplified using forward and reverse primers that have GC rich 5' ends, the forward primers begin with 5' GGCCWW and reverse direction primers begin with the sequence 5' GCWW (W=A or T); where the PCR products amplified with primers are converted to DNAs with 5' single stranded G/C rich overhangs by the action of T4 DNA polymerase in the presence of dATP and dTTP; and, where the 3" to 5' exonuclease activity of T4 DNA polymerase removed 3' nucleotides from DNA ends until counteracted by the 5' to 3' DNA synthesis activity.

Also, in certain embodiments, generation of sticky ends on PCR products, annealing of vector, and insert and ligation are all accomplished in a single reaction using a mixture of DNA polymerase, kinase and ligase enzyme activities.

In yet another broad aspect, there is provided herein a method for directionally ligate a PCR product into one or more expression vectors using at least one method as described herein, regardless of the presence or absence of restriction enzyme sites within the DNA.

In yet another broad aspect, there is provided herein a method as described herein where the expression vector is a pJL43 vector.

In yet another broad aspect, there is provided herein a method where purified PCR product [amplified with 5' phosphorylated primers that begin with 5'GGCCWW and 5'GCWW (W=A or T)] is added to SapI cut pJL43; a mixture of T4 DNA polymerase, the nucleotides dATP/dTTP and T4 DNA ligase are added to combined vector and PCR product, where during this step the 5' overhangs of SapI cut pJL43 are altered by the T4 DNA polymerase; a single G residue is removed from the 3' end of the left end of the SapI cut vector, to generate a 5' overhang of GGCC; a single A residue is added to the 3' end of the right end of the SapI cut vector, to generate a 5' overhang of GC; and, where the 3' to 5' exonuclease activity of T4 DNA polymerase in the presence of dATP and dTTP removes G or C residues from the 3' ends of the PCR product, and complementary 5' overhangs in vector and PCR product (insert) guide annealing of DNAs; and wherein annealed DNAs are joined by T4 DNA ligase.

Those skilled in the art will understand that these embodiments are representative only of many constructs which may be useful to produce localized or non-systemic expression of nucleic acids in host organisms such as plants. All such constructs are contemplated and intended to be within the scope of the present invention.

The following examples illustrate the principles of the invention as applied to modification of TMV and the use of modified TMV containing a gene coding for green fluorescent protein (GFP) in the phenotypic transformation of various plants and protoplasts. The following examples utilize many techniques well-known and accessible to those skilled in the arts of molecular biology, cloning, plant cell biology, plant virology and plant tissue culture. Such methods are fully described in one or more of the cited references if not described in detail herein. Unless specified otherwise, enzymes were obtained from commercial sources and were used according to the vendor's recommendations or other variations known to the art. Those in the art also know reagents, buffers and culture conditions and reaction conditions for various enzyme-catalyzed reactions. Reference works containing such standard techniques include the following: R. Wu, ed. (1979) Meth. Enzymol. 68; R. Wu et al., eds. (1983) Meth. Enzymol. 100, 101; L. Grossman and K. Moldave, eds. (1980) Meth. Enzymol. 65; J. H. Miller (1972) Experiment's in Molecular Genetics; R. Davis et al. (1980) Advanced Bacterial Genetics; R. F. Schleif and P. C. Wensink (1982) Practical Methods in Molecular Biology; and T. Maniatis et al. (1982) Molecular Cloning.

As used herein, the name of a restriction endonuclease in isolation, e.g., "StuI-XbaI" or "PacI" refers to use of that enzyme in an enzymatic digestion, except in a diagram where it can refer to the site of a sequence susceptible to action of that enzyme, e.g., a restriction site. Restriction sites may be indicated by the additional use of the word "site", e.g., "PacI site". The additional use of the word "fragment", indicates a linear double-stranded DNA molecule having ends generated by action of the named enzyme (e.g., a restriction fragment). A phrase such as "SmaI-BstEII" fragment" indicates that the restriction fragment was generated by the action of two different enzymes, here SmaI and BstEII, the two ends resulting from the action of different enzymes. Note that the ends will have the characteristics of being either sticky (i.e., having a single strand of protrusion capable of base pairing with a complementary single-stranded oligonucleotide) or blunt (i.e., having no single-stranded protrusion). The specificity of a sticky end will be determined by the sequence of nucleotides comprising the single-stranded protrusion, which in turn is determined by the specificity of the enzyme, which produces it.

All plasmids are designated by a sequence of letters and numbers prefaced by a lower case "p", for example, pJL36, pJL48, or pJL-TRBO. Certain steps of cloning, selection and vector increase employed strains of *E. coli*. While the strains used herein have been designated, there are many equivalent strains, available to the public that may be employed. In certain embodiments, the use of a particular microorganism as a substitute for a strain designated herein is a matter of choice available to those of ordinary skill in the art, according to well-known principles.

The following examples are intended to illustrate preferred embodiments of the invention and should not be interpreted to limit the scope of the invention as defined in the claims, unless so specified.

EXAMPLE I

PCR Reactions: Taq DNA polymerase was used for all PCR reactions, using manufacturers' instructions. For production of 5' phosphorylated PCR products, both forward and reverse direction PCR primers were treated with T4 polynucleotide kinase (New England Biolabs) according to manufacturers' instructions, prior to use in the PCR. Amplified reaction products were column purified with the DNA clean up and concentrator kit (Zymoresearch) to remove unincorporated dNTPs and primers. Purified PCR products were eluted in dH$_2$O.

Plasmid constructs: The duplicated Cauliflower Mosaic Virus (CaMV) 35S promoter, a short polylinker containing an XbaI site, and the polyA/terminator sequences from pRTL2 (Carrington and Freed 1990) were cloned as a PstI fragment into PstI cut binary vector pCB301 (Xiang et al. 1999) to create pCB 35SGFP. The NotI site in the pCB301 backbone of pCB 35SGFP was then destroyed by digesting with NotI, treatment with T4 DNA polymerase and dNTPs followed by religation to generate pCB 35SGFP ΔN.

Inverse PCR of pCB 35SGFP ΔN was used to generate a unique StuI restriction site at the 35S promoter transcription start site as described in (Dessens and Lomonossoff 1993). The resulting plasmid was named pJL 22.

The plasmid p3OB-GFP (Shivprasad et al. 1999) was originally obtained from Large Scale Biology Corporation (Vacaville, Calif.). This plasmid contains a T7 driven cDNA of the U1 strain of TMV, an additional viral subgenomic promoter controlling the expression of the GFP reporter gene, and a ribozyme sequence (Turpen et al. 1993) following the end of the viral cDNA. (See FIG. 1).

Assembly of the full length 30B-GFP vector in pJL 22 was accomplished in steps. First, p3OBGFPc3 was digested with StuI and PacI, sticky ends were blunted by treatment with T4 DNA polymerase and dNTPs and the plasmid religated to delete TMV nts 1675-5757. This deletion of about 4 kb of internal TMV vector sequence mutant was subjected to PCR with forward primer JAL 228 (GTATTTTTACAACAATTACCAAC) [SEQ ID NO: 1] and reverse direction primer JAL 229 (GGGCCTAGGCTATGACCATGATTACGC) [SEQ ID NO: 2] to generate a 3.6 kb PCR product. Primer JAL 228 annealed to the very 5' end of TMV. Primer JAL 229 has an AvrII (underlined) site for cloning and annealed in the vector backbone of p3 OBGFP downstream of the ribozyme sequence. The ribozyme sequence was present to process transcripts of p30BGFP at the precise 3' end of the TMV RNA. The 3.6 Kb PCR product of primers JAL 228 and 229 was phosphorylated with T4 polynucleotide kinase, digested with AvrII, and then ligated to StuI-XbaI cut pJL 22. The resulting plasmid was called pJL 23. In pJL 23, the TMV 5' end joined to the transcription start site of the 35S promoter. (See FIG. 1).

Figure 1:
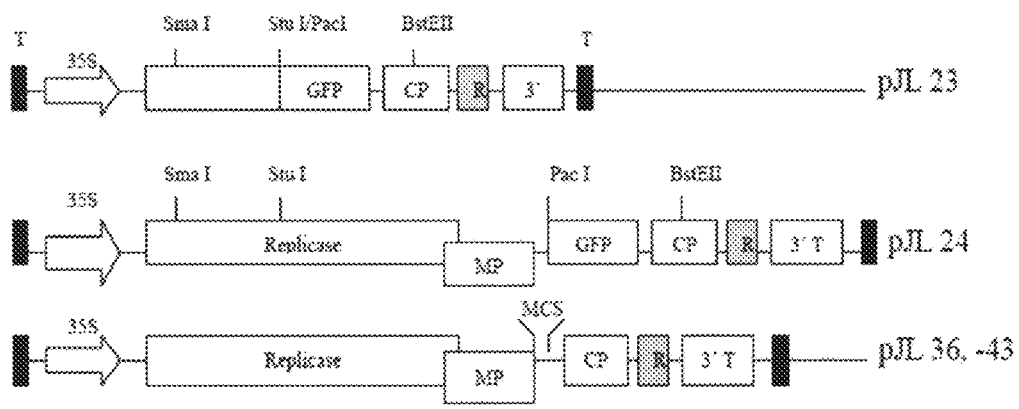
FIG. 1: Maps of plasmids used or generated—p30BGFP is a TMV vector under the control of the T7 promoter. Individual genes in TMV vectors are depicted by open boxes. TMV vectors express genes expressed from subgenomic promoters (sgp) in the viral RNA. Location of sgps in the TMV cDNA are identified by bent arrows in the p30BGFP diagram. T7 transcripts of p30BGFP are processed by a ribozyme (Rz, grey box) to generate the authentic 3' TMV end.

A 5.6 kb vector backbone fragment of SinaI-BstEII digested pJL 23 was ligated to a 6.3 kb SmaI-BstEII fragment of TMV sequences from p30BGFP to generate plasmid pJL24 (FIG. 1). This step completed the assembly of the full-length sequence of 30BGFP into a binary vector.

Additional TMV expression vectors, containing convenient cloning sites and the coding sequence for a V5 epitope-His6 tag sequence, were also assembled in binary vectors. The Green Fluorescent Protein (GFP) insert in p30BGFP was excised by digestion with PacI and XhoI. Overlapping oligonucleotides JAL 230 (taacggcctagggcggccgc) [SEQ ID NO: 3] and JAL 231 (tcgagcggccgccctaggccgttaat) [SEQ ID NO: 4] were ligated into PacI-XhoI cut p30BGFP. This resulted in the insertion of PacI, AvrII and NotI restriction sites into p30B, in place of the GFP insert. The resulting plasmid was named p30B PAN.

A SmaI-BstEII fragment from p30B PAN was ligated into similarly digested pJL 23 to generate plasmid pJL36. (See FIG. 1, FIG. 5A and FIG. 5B). [SEQ ID NO: 5].

A synthesized ds DNA cassette containing the coding sequence for two SapI sites (gctcttc), the V5 epitope (amino acid sequence GKPIPNPLLGLD) [SEQ ID NO: 6] and a His6 tag sequence [SEQ ID NO: 19] was ligated into PacI-XhoI cut p30BGFP to generate p30B 43. The DNA cassette-top stand sequence:

(CGAGGCCAGAAGAGCAACCTTTACG-
TACTTGCTCTTCAGCTTGAAGGT AAGCCTATC-
CCTAACCCTCTCCTCGGTCTCGATTC-
TACGCGTACCGGTCATCAT CACCATCACCATTGAC)
[SEQ ID NO: 7] had PacII-XhoI compatible ends but did not regenerate the PacI site. The first codon of the V5 epitope sequence is underlined in the DNA cassette sequence provided. A SmaI-BstEII fragment from p30B43 was ligated into similarly digested pJL23 to generate plasmid pJL43. (See FIG. 1 and FIG. 2) [SEQ ID NO: 8].

Construction of a binary vector for expression the p19 gene: Inverse PCR of the template pCB 35SGFP ΔN was used to insert a PacI restriction endonuclease recognition site immediately upstream of the start codon of GFP. GFP was removed from the resulting vector by digestion with PacI and XbaI The coding sequence for the p19 gene from Tomato Bushy Stunt Virus was amplified from a TBSV cDNA sample with Forward direction oligo JAL 55 (cccttaattaa cATGgaa cgagctata caaggaaac) [SEQ ID NO: 9], ATG start codon in all caps, PacI site underlined, and reverse direction oligo JAL 11 (ccctactagtcTTActcgccttcttttcgaa) [SEQ ID NO: 10], sequence complementary to stop codon in all caps, SpeI site underlined. The PCR product of primer JAL 55 and 11 was digested with PacI and SpeI and ligated into PacI-XbaI cut vector to generate pJL3:p19.

Sticky RICE cloning into pJL43: Preparation of vector: To prepare pJL43 for sticky RICE cloning, plasmid DNA was digested with the restriction endonuclease SapI, treated with calf alkaline intestinal phosphatase and purified with a DNA clean up kit (Zymoresearch). Purified DNA was eluted in $dH_2O$.

Preparation of PCR products: For sticky RICE cloning of PCR products into SapI cut pJL43 the 5' end of the forward PCR direction primer can be 5' GGCCWW. The 5' end of the reverse direction PCR primer can be 5' GCWW. In the primer sequences, W=A or T. The T and A residues in the primers can serve as "stop nucleotides" during the sticky RICE reaction, where PCR products were incubated in the presence of a DNA polymerase with 3' to 5' exonuclease activity and dATP and dTTP.

The DNA polymerase removed nucleotides from the 3' ends of each strand until an A or T residue was present in the template stand. This resulted in 5' overhangs on each end of the PCR products. (See FIG. 2).

Using these steps for primer design, the GFP gene was amplified by the PCR from a pUC-based plasmid with F primer JAL 286 (GGCCT aaa atggctagcaaaggagaag) [SEQ ID NO: 11] and R primer JAL 287 (GCttatttgtagagctcatccat) [SEQ ID NO: 12]. The primer nucleotides that were converted to sticky ends by T4 DNA polymerase are in bold in FIG. 2.

PCR reactions using either non-phosphorylated or 5' phosphorylated primers were performed. PCR products were purified with a DNA clean up column (Zymoresearch) to remove unincorporated dNTPs and primers and eluted in $dH_2O$.

Assembly of the Sticky RICE reaction: A three-fold molar excess of phosphorylated GFP gene PCR product was combined with 50 ng SapI cut and phosphatase treated pJL43 DNA in a 10 µl reaction volume composed of: 1× ligase buffer, 0.1 mM (each) dATP/dTTP, 0.25 Units T4 DNA Polymerase, and 400 Units T4 DNA ligase. Enzymes, buffers and unit definitions were all from New England Biolabs. The assembled reaction was incubated at room temperature for 30 minutes.

For purposes of comparison, non-phosphorylated GFP gene PCR products were also cloned using the same reaction conditions except that 0.5 Units T4 polynucleotide kinase were also included in the reaction. The cloning of the GFP gene into pJL43 resulted in plasmid pJL43:GFP.

Transformation of E. coli with Sticky RICE cloning reaction: Two microliters of a sticky RICE ligation reaction were added to 25 µl of chemically competent E. coli (Bioline, AlphaSelect Gold efficiency). Transformation conditions were essentially as per manufacturers' instructions. Transformed cells were plated on LB plates with 50 µg/ml Kanamycin.

Screening plasmids for inserts: Following transformation of the sticky RICE ligations into E. coli, individual colonies were used to inoculate LB broth with 50 µg/ml Kanamycin. Liquid cultures were grown overnight at 37° C., 300 rpm. Plasmids were purified from overnight liquid cultures using a plasmid miniprep kit (Zymoresearch). Because the forward-direction primer used for PCR began with the sequence "GGCCT", a StuI restriction enzyme recognition site was generated upon sticky RICE joining of PCR product to pJL43. Therefore, plasmids were screened by digestion with StuI and digested DNA separated on 1% agarose gels to identify clones that had inserts.

Agroinfection: Plasmids purified from E. coli cultures were transformed into Agrobacterium GV3101 using the freeze thaw method (Chen et al. 1994). Transformed Agrobacterium were plated on LB plates with 50 µg/ml Kanamycin, 25 µg/ml gentamycin and 10 µg/ml rifampicin for plasmid selection. Individual colonies of Agrobacterium transformed with a binary plasmid were grown to an $OD_{600}$ of 1.0 in liquid LB media supplemented with 10 mM MES pH 5.7, 50 µg/ml Kanamycin, 25 µg/ml gentamycin and 20 µM acetosyringone. Cells were precipitated by centrifugation and resuspended in Agrobacterium induction media (Johansen and Carrington 2001). Cells sat at room temperature in induction media for 2-24 hours before infiltration into N. benthamiana leaves using a 1 ml syringe with no needle. When mixes of Agrobacterium were infiltrated, bacterial cultures were prepared separately in induction media and were combined immediately before infiltration.

Results for Example I:

To generate TMV vectors that would infect plants via the agroinfection method, the TMV vector cDNA was placed under the control of a plant functional promoter in a binary vector. The cDNA sequence for the TMV vector '30B GFP' was placed under the control of a 35S promoter in the mini binary vector pCB301. Variants of this plasmid were also constructed in which the GFP insert in the TMV vector was replaced with multiple cloning sites. (See FIG. 1).

The pCB301 plasmid backbone replicates in both E. coli and Agrobacterium and has a kanamycin resistance selectable marker. Plasmids pJL24,-36, and -43 were all initially tested by agroinfiltration and determined to be infectious on Nicotiana benthamiana plants, as determined by the appearance of TMV-induced symptoms of infection about 11 days post infiltration (data not shown). Cloning and expression of genes from pJL43, in particular, was undertaken to demonstrate the utility of these new vectors.

To show that the restriction-enzyme independent cloning strategy "sticky RICE" can be used for cloning PCR products into a TMV vector, a cloning experiment using the vector pJL43 was conducted. The pJL43 vector was prepared for cloning by digestion with the restriction endonuclease SapI and treated with calf intestinal phosphatase. Sticky RICE cloning reactions were set up using either a phosphorylated or non-phosphorylated ca. 800 by PCR product of the GFP gene. Sticky RICE ligation reactions were performed for 30 minutes at room temperature before transformation into E. coli cells. As shown in Table 1 below, the sticky RICE cloning reaction of this insert yielded considerably more transformants when phosphorylated PCR products were used.

TABLE 1

Cloning Efficiency when using Sticky RICE Method

| Insert Size, (bp) | 5'PO$_4$ on insert | Enzyme mix[a] | Reaction Time | Colonies | # % With insert[b] |
|---|---|---|---|---|---|
| 770 | No | Pol/Kin/Lig | 30 min | 77 | 7/8 (ca 90%) |
| 770 | Yes | Pol/Lig | 30 min | 376 | 7/8 (ca 90%) |

[a]Poi, 0.25 Units (U) T4 DNA polymerase; Kin, 0.5 U T4 polynucleotide kinase; Lig, 400 U T4 DNA ligase.
[b]Percentage of clones recovered with insert, as determined by restriction enzyme screening.

To test the cloning efficiency (percentage of transformants containing inserts) of the sticky RICE method, plasmids were purified from eight randomly selected colonies of transformed *E. coli*. Plasmids were digested with StuI restriction endonuclease and analyzed by electrophoresis on 1% agarose gel followed by staining with ethidium bromide. A StuI site already exists in the TMV cDNA sequence (at TMV nt 1675) and a StuI site was generated during sticky RICE cloning. As a result, plasmids containing an insert will release a StuI fragment of approximately 4 kb. Seven out of 8 plasmids screened contained an insert, for a cloning efficiency of approximately 87.5% (Table 1).

The agroinfection efficiency of the TMV expression vector in pJL43 was also determined. This was tested by transforming the plasmid pJL43:GFP (a pJL43 vector containing the GFP insert) into *Agrobacterium* GV3101. Cultures of *Agrobacterium*/pJL43:GFP were suspended in induction media at an OD$_{600}$ 1.0. Leaves of 4-6 week old *Nicotiana benthamiana* plants were infiltrated with 100-200 microliters of induced *Agrobacterium* culture. Three days post-infiltration GFP expressing cells were seen using a hand-held UV lamp. (See FIGS. 3A and 3B).

Each GFP expressing cluster of cells represents a single incident of the GFP-expressing TMV vector RNA being "launched" from the transcribed T-DNA, and the TMV:GFP vector moving from the initially infected cell to adjacent cells. Hundreds of GFP spots were detected per 10 cm$^2$ of infiltrated leaf. (See FIG. 3A).

By about 7 days post infiltration signs of systemic infection by the TMV:GFP virus were detectable (data not shown). By 11 days post agroinfection, the systemic infection was well established, and very little non-GFP expressing systemic plant tissue was observed. (See FIG. 3B).

Although infiltration of *Agrobacterium*/pJL43:GFP cultures alone into *N. benthamiana* plants always led to systemic infection of plants by TMV:GFP, additional experiments were conducted to determine if agroinfection efficiency could be improved. Additional experiments were conducted to determine if RNA silencing suppressor proteins could increase the agroinfection efficiency of the TMV clones. To test this, *N benthamiana* plants were infiltrated with a 1:1 mixture of induced *Agrobacterium*/pJL3:p19 and pJL43:GFP cultures (each at an OD$_{600}$ of 1.0). The plasmid pJL3:p19 contains a T-DNA sequence of the 35S promoter driving the transcription of the RNA silencing suppressor p19 gene from tomato bushy stunt virus. When plants were infiltrated with a mixture of these two *Agrobacterium* cultures, a dramatic increase in the number of GFP expressing cells was observed. By three days post infiltration it appeared that nearly 100% of the cells in the infiltrated tissue were infected with TMV:GFP. (See FIG. 3A).

To further demonstrate the effect of p19 on agroinfection efficiency, plants were infiltrated with a 50-fold dilution of *Agrobacterium*/pJL43:GFP culture (diluted from the OD$_{600}$ of 1.0), with and without co-infiltration of an *Agrobacterium*/pJL3:p19 culture. (See FIG. 3A).

The results demonstrated that leaves infiltrated with a 1:50 dilution of *Agrobacterium*/pJL43:GFP culture generated only about 80 GFP expressing foci by 3 days post infiltration (DPI). In contrast, when the diluted *Agrobacterium*/pJL43:GFP culture was co-infiltrated with *Agrobacterium*/pJL3:p19 culture nearly 100% of the cells in the infiltrated zone expressed GFP by 3 DPI.

Systemic symptoms of TMV:GFP infection began appearing about 7-8 days post agroinfection with pJL43:GFP. By co-introducing a gene for the RNA silencing suppressor gene p19 along with the TMV vector T-DNA during agroinfection, substantially complete infection of the local (infiltrated) tissue was achieved. Therefore, experiments were conducted to determine if the levels of recombinant protein generated in this infiltrated tissue were comparable to that of the systemically infected tissue. Protein extracts were prepared from plant tissue infiltrated with *Agrobacterium*/pJL43:GFP and /pJL3:p19 cultures (at 5 DPI), as well as from plant tissue systemically infected with the TMV:GFP construct from pJL43:GFP (14 DPI). Protein extracts were analyzed by SDS-PAGE and Coomassie blue staining. The levels of recombinant GFP protein were comparable in both samples. See FIGS. 4A and 4B which demonstrate that significant levels of recombinant protein can be produced from TMV vectors in the Agroinfiltrated tissue itself. Furthermore recombinant protein can be detected in infiltrated tissue many days before TMV:GFP begins systemic infection.

Discussion of Example I:

There is described herein a method of agroinfection to deliver TMV-based expression vectors to plants. A 35S promoter driven version of the TMV expression vector '30B GFP' was re-constructed in the T-DNA region of a binary vector. During construction, care was taken to ensure that the promoter transcription start site and TMV cDNA junction was precise. The binary plasmids constructed all replicated in *E. coli* and *Agrobacterium*. Leaf tissue infiltrated with *Agrobacterium* cultures containing the new 35S driven TMV vector developed hundreds of GFP expressing foci per cm$^2$ of infiltrated tissue by 3 DPI. (See FIG. 3). Approximately 7-8 DPI GFP signal began appearing in upper (non-infiltrated) leaves as a result of systemic infection by the TMV:GFP vector.

When the 35S driven TMV vector T-DNA was introduced into plant cells along with a T-DNA for the RNA silencing suppressor protein p19 gene, a dramatic increase in agroinfection efficiency was observed. (See FIG. 3).

Nearly all of the cells in the infiltrated tissue zone expressed GFP by three days post infiltration. The infection of infiltrated tissue was so efficient that the levels of recombinant GFP in infiltrated or TMV:GFP systemically-infected tissue were comparable. (See FIG. 4).

The infection method described herein makes it possible to screen infiltrated tissue for recombinant protein production. When viral vectors (such as TMV-based vectors) move systemically in plants there is a tendency for foreign inserted genes to be lost from the viral RNA by recombination. As a result, there can be plants that become partially- or totally-systemically infected with a TMV vector that has lost the foreign insert. This "insert-loss" phenomenon is influenced by insert length and insert sequence in ways that are not completely understood.

As now described herein, the ability to infect nearly every plant cell with a TMV vector by agroinfiltration now makes it possible to produce significant amounts of recombinant proteins in plants without the same concerns of insert stability in the vector. Also, systemic infection of plants after inoculation with a viral vector generally takes about 7 or more days. The high efficiency of agroinfection described herein makes it possible to harvest recombinant protein several days before systemic symptoms of virus infection even begin to appear.

The efficiency of agroinfection, obtained by co-introducing an RNA silencing suppressor, is now believed by the inventor herein to be comparable to the agroinfection efficiencies recently reported by Marillonnet et al. (Marillonnet et al. 2005). In their approach to improving agroinfection of a TMV vector, they both removed potential cryptic introns (by making nearly 100 silent mutations to the virus cDNA sequence) and inserted up to 19 introns into the viral cDNA. The final optimized construct generated through their strategy had multiple silent mutations and 16 introns inserted into the viral cDNA. They estimated this construct was 1000 times more efficient in agroinfection of N. benthamiana plants than their starting vector. Through agroinfection they were able to infect greater than 90% of the cells in the infiltrated leaf with a GFP expressing TMV.

To estimate the efficiency of agroinfection obtained in the experiments described herein, infiltrated tissue was observed under a fluorescent microscope and UV illumination. Even when leaves were infiltrated with a 1:1 mixture of Agrobacterium/pJL3:p19 (at $OD_{600}$ 1.0) and Agrobacterium/pJL43: GFP (diluted 1:50 from $OD_{600}$ 1.0), nearly 100% of the cells in the infiltrated tissue expressed GFP at 4 DPI. It is now believed that the expression of p19 in infiltrated cells dramatically improved agroinfection efficiency of the new TMV vector, obviating the need to destroy cryptic introns or introduce introns into the constructs.

Co-expression of an RNA silencing suppressor was recently reported to increase the agroinfection efficiency of a 35S driven Beet Yellows Virus (BYV) cDNA. As now shown herein, the RNA silencing suppressors increase agroinfection efficiency of 35S driven RNA virus cDNAs is not restricted to BYV. The enhancement of agroinfection efficiency by RNA silencing suppressors is now believed by the inventor herein to be a general phenomenon. One mechanistic explanation for this enhancement that is that the TMV cDNA transcribed in the plant cell nucleus is often spliced at cryptic introns. This is supported by the observation that removal of cryptic introns from TMV cDNA could improve the agroinfection efficiency of TMV vector (Marillonnet et al. 2004; Marillonnet et al. 2005). As a result of splicing in the nucleus TMV-derived RNA that is not capable of self-replication is often exported into the cytoplasm. This does not initiate self-replication, but instead is processed by cellular RNAses and becomes a source of small RNAs that become incorporated into the RNA-induced silencing complex (RISC) (Filipowicz 2005). These small RNAs would serve as guide RNAs to target the RISC complex to specifically degrade TMV RNA. This would result in the RISC complex rapidly degrading other transcription products of the TMV cDNA (including the occasional transcript that is not spliced) that enter the cytoplasm. As a result of this activity, agroinfection efficiency of an RNA virus is limited. In contrast, when a potent suppressor of RNA silencing is co-expressed in cells that are transformed with a 35S driven TMV cDNA, the silencing suppressor interferes with RNA degradation by RISC. As a result when non-spliced viral transcripts do enter the cytoplasm from the nucleus they are not immediately degraded but instead have a greater opportunity to be translated and initiate self-replication.

Based on the results of agroinfection by 35S driven BYV and TMV constructs it is believed by the inventor herein that co-infiltration of an RNA silencing suppressor gene improves the agroinfection efficiency of other RNA virus cDNAs as well. This method, as described herein, is a more efficient method to improve agroinfection efficiency of viral cDNAs as opposed to the removal of cryptic introns and introduction of introns into viral sequences.

To facilitate the cloning of genes into the agroinfiltration-compatible TMV vector, the GFP gene in pJL24 was replaced with useful multiple cloning sites to generate pJL36 and pJL43. Plasmid pJL36 has three unique restriction enzyme sites for cloning, two 8-base restriction enzyme recognition sites (PacI and NotI) and the 6-base AvrII site. The sticky ends generated by AvrII digestion are compatible with sticky ends generated by digestion of DNA with restriction enzymes, NheI, SpeI or XbaI, providing for flexibility in cloning. This vector can be used for standard restriction endonuclease based cloning approaches, and can be propagated in either E. coli or Agrobacterium.

The multiple cloning site in pJL43 was created because there can be occasions when a DNA sequence to be cloned is not compatible with the PacI-AvrII and NotI restriction site choices provided in pJL36. Therefore, to provide other cloning options, an alternative, directional one-step cloning method, called "sticky RICE cloning" was also developed. In this method, two SapI restriction endonuclease recognition sites were inserted into the TMV vector cDNA sequence. The context of the SapI sites was specially designed so that 5' single stranded overhangs would be maintained in the SapI cut vector in the presence of T4 DNA polymerase and dATP and dTTP. (See FIG. 2).

PCR products were amplified using forward and reverse primers that had GC rich 5' ends. Forward primers began with 5' GGCCWW and reverse direction primers began with the sequence 5' GCWW (W=A or T). PCR products amplified with primers designed in this manner were converted to DNAs with 5' single stranded G/C rich overhangs by the action of T4 DNA polymerase in the presence of dATP and dTTP. The 3' to 5' exonuclease activity of T4 DNA polymerase removed 3' nucleotides from DNA ends until counteracted by the 5' to 3' DNA synthesis activity. Since only dATP and dTTP were present in the reaction, the counteracting DNA synthesis activity only occurred when a T or A residue was reached in the template strand. In this manner, 5' GC rich single stranded overhangs of defined length and sequence were generated on the PCR product.

Because of the special design of both the vector and PCR products to be cloned, the generation of sticky ends on PCR products, annealing of vector, and insert and ligation were all accomplished in a single reaction using a mixture of DNA polymerase, kinase and ligase enzyme activities. This greatly simplifies the cloning process, obviating the need to digest PCR products with specially selected restriction enzymes prior to cloning. In fact, using the sticky RICE cloning method it is now possible to directionally ligate a PCR product into these specially designed TMV expression vectors in 30 minutes, less time than it takes to do the typical restriction enzyme digest. Because the sticky RICE method does not rely on restriction digestion of PCR products to be cloned, it is now possible to reliably clone PCR products regardless of the presence or absence of restriction enzyme sites within the DNA. The sticky RICE method is especially appealing when undergoing high-throughput cloning experiments or when cloning DNA sequences whose entire sequence is not known.

There are a number of directional cloning techniques currently available, including methods using topoisomerase (Shuman 1994) or recombinase enzymes (Buchholz and Bishop 2001; Walhout et al. 2000) (Gateway® system, Invitrogen) and ligase independent cloning (Aslanidis and de Jong 1990). The sticky RICE method described herein uses commonly available enzymes and is significantly less expensive to perform than these commercially marketed directional cloning methods. In addition, the primer design for sticky RICE only requires that relatively short non-template sequences be added to primers. Also, the LIC method requires 12 non-template encoded nts be added to each PCR primer. Recombinase based methods like the Gateway® system (Walhout et al. 2000) and cre-lox (Buchholz and Bishop 2001; Liu et al. 1998; Liu et al. 2000) systems join DNAs that share specific 26 or 34 nt long recombinase recognition sequences, respectively. These sequences are additional (non-template) sequences that must be added to PCR products to be cloned. These specific recombination sequences must also be inserted into the vector. This can be a limitation because there may be instances when it is not desirable to have such long sequences inserted into a cloning and expression vector. In contrast, the coding sequence requirements for sticky RICE are not as restrictive.

The sticky RICE cloning method is also not limited to just the TMV expression vectors. It is believed by the inventor herein that nearly any cloning vector of interest can be converted to being "sticky RICE compatible" using the method described herein. For example, a number of 5' overhang sequences and lengths can be used, depending upon the users' own design. In addition, A/T rich 5' overhangs can be used instead of G/C rich 5' overhangs by properly designing vector and PCR primers and using dGTP and dCTP to limit the 3' to 5' exonuclease activity of T4 DNA polymerase.

EXAMPLE II

Plasmids constructed: Agroinfection-compatible TMV expression vector (pJL24, FIG. 8) that expressed all of the TMV genes in addition to a foreign, inserted gene was constructed. Since moving the foreign gene insertion site closer to the 3' end of TMV RNA led to an increase in expression of the foreign insert, deletion of the virus CP gene sequence from the plasmid pJL24, in essence, moves the foreign insert closer to the 3' end of the viral RNA. As such, deletion of the CP gene sequence from pJL24 increased the level of foreign gene expression from a TMV replicon. The CP deletion replicon was named TRBO for TMV RNA Based Overexpression vector. Initially, the green fluorescent protein (GFP) reporter gene (Chalfie et al. 1994; Chalfie 1995; Crameri et al. 1996) was used to demonstrate the utility of the agroinfection-compatible TRBO replicon and to compare it to alternate non-viral or full-length TMV-transient expression systems. Maps of the T-DNA regions of various modified Ti (binary) plasmids used in this example are shown in FIG. 8.

For example, see FIG. 6 which shows pJL48 (pJL-TRBO)-GFP 35S driven TMV in binary vector with deletion of the CP gene. Kan resistance marker and T-DNA borders not shown in map. Plasmid replicates in either Agro or *E. coli*. Construction: GFPc3 gene (PCR product of oligos JAL 12 and 13). Digested with PacI-SpeI. Ligated into PacI-AvrII cut pJL48 (pJL-TRBO). Use: infiltrate *Agrobacterium* containing this plasmid into *N. benth* plants to produce GFP.

FIG. 7A shows the plasmid maps of pJL22 U1 3', pJL36, and pJL48 (pJL-TRBO)=35S driven TMV expression vector in binary vector backbone. Clone is lacking a CP orf and is capable of high-level expression of protein in plants. T-DNA borders not shown in map. Construction: vector backbone=pJL36 NotI-SfiI cut. Insert=1.5 kb NotI-SfiI fragment of pJL 22 U1 3'. FIG. 7B shows the DNA Sequence of pJL48 (pJL-TRBO) expression vector [SEQ ID NO: 13]. Nt 1=first nt of TMV U1 strain. PacI (TTAATTAA), AvrII (CCTAGG) and NotI (gcggccgc) sites for cloning. After NotI site, U1 nts 6177 to 6396 (number according to Goelet et al 1982, Proc. Natl. Acad. Sci.) Vector has No CP gene, and is composed only of TMV U1 strain sequences, and other (non-viral) sequences for cloning, etc.

Agroinfection with the TRBO replicon is very efficient: Experiments with the TMV vector contained in pJL24 determined that ectopic co-expression of an RNA silencing suppressor gene (such as the p19 gene from tomato bushy stunt virus) was useful to obtain the highest agroinfection rates for this vector. An example of this can be seen in FIG. 9. The area of the leaf in region "A" of FIG. 9 was infiltrated with a suspension of *A. tumefaciens* cells carrying pJL-24 (A.t./pJL24). When the leaf was viewed under UV illumination (to visualize expression of GFP from the TMV vector launched from the T-DNA) many discreet GFP-positive foci could be seen with the unaided eye. However, a significant portion of the infiltrated leaf did not express detectable levels of GFP. In contrast, when A.t./pJL24 cells were mixed with a suspension of A.t./pJL3:P19 cells and the mixture infiltrated into leaf tissue, GFP expression in the infiltrated zone appeared confluent (area B, FIG. 9).

Very few, if any, non-GFP expressing cells were observed even when examined under a fluorescent microscope (data not shown). Because the most efficient agroinfection rate with pJL24 required co-introduction of a 35S driven P19 gene, experiments were conducted to determine if co-expression of the RNA silencing suppressor protein P19 was also needed to obtain a high agroinfection rate with the vector TRBO-G.

To test this, A.t./pJL-TRBO-G cells alone (FIG. 9C) or mixed with A.t./pJL3:P19 cells (see FIG. 9D) were infiltrated into separate areas of a leaf. Surprisingly, the agroinfection rate of the TRBO-G vector in the two treatments appeared identical. When infiltrated leaves were viewed under a hand-held long wave UV lamp at 4 days post infiltration (DPI), all cells in the area of the leaf infiltrated with A.t./pJL-TRBO-G or A.t./pJL-TRBO-G+A.t/pJL3:P19 cells appeared to be expressing GFP (see FIGS. 9C and 9D). In addition, the GFP signal from pJL-TRBO-G replicon was noticeably brighter than the GFP signal from pJL24. These results were observed in dozens of repetitions of this experiment.

Since the TRBO vector had a higher rate of agroinfection than the vector JL24, it was then determined whether dilute suspensions of A.t./pJL-TRBO-G alone could be used to efficiently inoculate leaves. Half leaves of *N. benthamiana* plants were infiltrated with various dilutions of A.t./pJL-TRBO-G cells. Leaves were observed daily with a hand-held UV lamp to monitor the progress and extent of agroinfection, as demonstrated by GFP expression from the TRBO replicon. Results are shown in FIG. 10A.

Even in leaves infiltrated with *A. tumefaciens* cells diluted 1:300 from a starting $OD_{600}$ of 1.0, nearly all cells of the infiltrated zone expressed GFP by 4 DPI, as determined by visual inspection of infiltrated leaves under a hand-held UV lamp. Thus, plants can be efficiently agroinoculated with the TRBO replicon over a wide range of A.t./pJL-TRBO-G cell densities.

To further demonstrate that the agroinfection rate of A.t./pJL-TRBO-G is higher than that of A.t./pJL24, a 1:100 dilution (from a starting $OD_{600}$ of 1.0) of A.t./pJL24 cells was infiltrated into N. benthamiana leaves with or without A.t./ pJL3:p19 cells. The image in FIG. 10B is a photograph (3DPI) of an infiltrated leaf under UV illumination. Again, co-infiltration of A.t./pJL24 and A.t./pJL3:p19 cell suspensions dramatically increased the agroinfection rate of the JL24 vector. The amount of GFP-expressing tissue in this treatment appeared similar visually to the amount of GFP-expressing tissue (at 3DPI) in leaves infiltrated with 1:150 or 1:300 dilutions of A.t./pJL-TRBO-G cells. (See FIG. 10A). This further demonstrates that the agroinfection rate of pJL-TRBO is significantly higher than that of pJL24 and that even diluted A.t./pJL-TRBO-G cell suspensions can be used to efficiently inoculate leaves in the absence of an ectopically expressed RNA silencing suppressor such as p19.

The TRBO expression vector did not move systemically in plants: Since the TMV CP is required for systemic movement (Donson et al., 1991), the JL-TRBO replicon does not move systemically in plants. To confirm, N. benthamiana plants were inoculated with the GFP-expressing vectors JL24 or JL-TRBO-G by agroinfection. Plants were observed under UV illumination to visualize GFP expression from the vectors. Results are shown in FIG. 11.

The vector JL24 expressed GFP plus all of the genes of TMV, including the CP, and moved systemically (to non-inoculated leaves) at about 5-6 DPI. By about 9-10 DPI, the majority of the tissue in systemically infected leaves (as viewed with the unaided eye under UV illumination) appeared to be expressing GFP. In contrast, the TRBO replicon did not move systemically in plants, even up to 14 DPI (data not shown). The JL-TRBO-G replicon was never observed to move systemically in any of the dozens of agroinoculated plants in any experiments.

TRBO vector expressed very high levels of recombinant protein: To compare the amounts of GFP produced from the TMV vectors JL24 and JL-TRBO-G, or from the transient co-expression of 35S:GFP and the RNA silencing suppressor protein p19, a plate based GFP fluorescence assay was used. Purified His6-tagged GFP (6xHis tag disclosed as [SEQ ID NO: 19]), purified from TRBO-G infected plants by metal affinity chromatography, was used as a standard. Leaves of N. benthamiana were infiltrated with one of the following A. tumefaciens (A.t.) cell suspensions: A.t./p35S:GFP+A.t./pJL3:P19 (each at an $OD_{600}$ of 0.5); A.t./pJL24+A.t./pJL3:P19 (each at an $OD_{600}$ of 0.5); or A.t./pJL-TRBO-G (OD 0.02). Protein samples from infiltrated tissues were prepared at 5 or 6 DPI. Dilutions of protein extracts and purified His6-tagged GFP (6xHis tag disclosed as [SEQ ID NO: 19]) were transferred into wells of a 96 well plate (in triplicate). GFP fluorescence levels were recorded on a Perkin Elmer HTS 7000 BioAssay plate reader. The results are shown in FIG. 12.

The JL-TRBO-G replicon expressed up to 100 times more GFP than was obtained from co-introducing T-DNAs for 35S:GFP and 35S:p19 into plants, and 2-3 times more GFP than the TMV vector pJL24. Similar results were also obtained from an ELISA assay, using anti-GFP specific antibodies (data not shown). In multiple repetitions of this experiment, the relative expression levels from the different expression systems were always consistent. The JL-TRBO replicon always expressed significantly more GFP than the other transient expression systems examined.

Temporal analysis of protein expression from TRBO: After the JL-TRBO-G T-DNA is transcribed, the RNA initiates self-replication and gene expression in the cytoplasm. Since the JL-TRBO-G replicon expressed the TMV movement protein, it moved cell-to-cell in the inoculated (infiltrated) leaf. The result of this movement is that individual GFP-expressing foci on a leaf enlarge as the virus moves cell-to-cell over time. This can be observed by comparing the sizes of individual GFP-expressing cell foci at 3DPI and 4DPI images (in FIG. 10A) of leaves infiltrated with 1:500 dilutions of A.t./pJL-TRBO-G. When leaves were infiltrated with higher concentrations of A.t./pJL-TRBO-G cells, the large number of GFP-expressing cells in the infiltrated zone made it difficult to identify an individual foci. Regardless, as replication and cell-to-cell movement of the replicon progressed the amount of GFP expressed in the infiltrated leaf increased. After a certain point the steady-state level of GFP in infiltrated tissue appeared to reach a plateau.

To demonstrate the temporal nature of protein expression from the JL-TRBO-G replicon, extracts were prepared from inoculated tissue at various DPI. Total soluble protein extracts were analyzed by SDS-PAGE and Coomassie blue staining. (See FIG. 13). JL-TRBO-expressed GFP accumulation appeared to reach a maximum at 4-6 DPI, consistent with the increase in GFP activity that is observed by viewing infiltrated leaves under UV illumination.

Expression of Various Proteins from JL-TRBO Replicon:

The high efficiency agroinfection of 35S:TMV allows whole leaves to be agroinfected with a gene of interest (GOI) where the whole leaf can be agroinfected with the TMV:GOI. Protein is recovered from the inoculated leaves, not from systemically infected leaves.

The CP gene is removed from the virus when there is no need for the virus to systemically move. The effect of removing the CP gene from the TMV-based expression vector moves the gene of interest (GOI) toward the 3' end of the genome. The gene closest to the 3' end is more highly expressed. The result is that the TMV vector over-expressed the GOI.

To demonstrate the utility of the JL-TRBO expression replicon, genes of various sizes were cloned into the pJL-TRBO plasmid. N. benthamiana plants were infiltrated with suspensions of A. tumefaciens cells transformed with the various plasmids. Several (4 to 6) days post infiltration, total soluble protein extracts were prepared from agroinfiltrated tissue. Extracts were separated on SDS-PAGE gels and stained with Coomassie blue. (See FIG. 14A).

Since some of the recombinant proteins expressed from JL-TRBO had C-terminal amino acid tags of $His6(HA)_2$ (6xHis tag disclosed as [SEQ ID NO: 19]) (where HA is the influenza hemagglutinin peptide YPYDVPDYA) [SEQ ID NO: 20]), some extracts (see FIG. 14B) were also subjected to immunoblot analysis using anti-HA primary antibodies (Invitrogen). The results of this analysis demonstrate that different recombinant proteins accumulate to different levels in plants. Some (e.g. Adenosine kinase) accumulate to greater levels than GFP. Other proteins accumulate at lower levels. The results also demonstrate that JL-TRBO can be used to express His-6 (6xHis tag disclosed as [SEQ ID NO: 19]) and epitope tagged recombinant proteins. Although several of the lesser-accumulating proteins had $His6(HA)_2$ C-terminal amino acid tags (6xHis tag disclosed as [SEQ ID NO: 19]), it is not proposed that this peptide tag was solely responsible for the lower accumulation levels. However, this tag may have an affect on the final level of accumulation on some proteins. For example $His6(HA)_2$-tagged GFP (6xHis tag disclosed as [SEQ ID NO: 19]) (FIG. 14A, lane 3) did accumulate to slightly lower levels than that of non-tagged GFP.

Discussion of Example II:

The construction of a full-length TMV vector that can be efficiently delivered to cells by agroinfection included a 35S driven RNA silencing suppressor gene that was co-introduced at the same time. In this example, a coat protein deletion (ΔCP) mutant of that 35S-driven TMV vector was described. This vector was efficiently delivered to cells by agroinfection irrespective of the co-expression of an RNA silencing suppressor protein. This data demonstrated that the sequences in or around the TMV CP gene had a significant, negative impact on agroinfection efficiency. The negative effect of the TMV CP sequence could be at least partially neutralized by ectopic expression of a suppressor of RNA silencing. Therefore, it is believed by the inventor herein that the RNA sequence of the TMV CP subgenomic promoter and CP open reading frame can be a potent inducer of RNA silencing.

The CP deletion vector, JL-TRBO, described in this example had several advantages over a full length TMV vector. The JL-TRBO vector had a dramatically higher agroinfection rate. As such, plants can be efficiently inoculated even with very dilute suspensions of A. tumefaciens. This can be important since there are some plant species which demonstrate a hypersensitive response when infiltrated with high density A. tumefaciens suspensions. Being able to agroinoculate plants with lower density cell suspensions reduces the chances of such 'negative responses' of the plant to A. tumefaciens.

Also, efficient inoculation with low density A. tumefaciens cell suspensions can make it easier to obtain sufficient inoculum for infiltration of multiple leaves or plants. Another useful feature of JL-TRBO was its remarkably high protein expression rate: for some proteins gram quantities of recombinant protein were produced per kilogram of infiltrated tissue. This is comparable to the highest recombinant protein expression levels ever reported for plants (Marillonnet et al., 2005). High protein expression levels make it easier to obtain useful quantities of recombinant protein from less tissue in less time.

One of the challenges of working with plant virus expression vectors is the tendency of vector deletion mutants to appear in systemically infected portions of inoculated plants (Dawson et al., 1989; Beck and Dawson, 1990; Lehto and Dawson, 1990; Shivprasad et al., 1999). Although the phenomenon is not completely understood, it was demonstrated that a recombinant plant virus with an insert moved more slowly than the same virus without an insert (Toth et al., 2002). This was especially true for systemic movement of recombinant viruses (Toth et al., 2002). Therefore, there is a selective advantage in movement for viruses that have lost their insert. As a result, a plant can be inoculated with a virus containing an insert yet when the virus appears in systemic (non-inoculated) tissue, the insert may have been lost by recombination. The ability to synchronously inoculate large numbers of cells in a leaf and purify proteins from the inoculated leaf itself reduces the chances for insert loss from the virus. Therefore, the pJL-TRBO vector described herein provides a more reliable expression vector because insert loss is less likely to be a problem than with the full-length TMV vectors.

Another advantage of the TRBO vector is that it does not produce TMV CP. Because the TMV CP is required for systemic movement, TRBO is not capable of systemic movement in plants. It also will not produce virions in plants. This has definitive bio-containment and protein purification advantages. Firstly, this feature reduces the chances for inadvertent plant-to-plant movement of the vector. Secondly, when extracting proteins from pJL-TRBO infected tissue, the recombinant protein of interest does not need to be purified away from virion particles. If one is using viral vector that does generate virus particles (such as JL24), efforts must be taken to both separate virion particles from the recombinant protein of interest and also to inactivate virus particles in any extracts of infected plant materials. These issues are not a concern with the pJL-TRBO vector because it does not generate virus particles.

The expression levels and agroinfectivity on N. benthamiana obtained with JL-TRBO are comparable to those of TMV-based vectors reported by others (Gleba et al., 2005; Marillonnet et al., 2005). These reports have described the construction of a TMV-(CP deletion) based replicon that could also express GFP at levels higher than 1 mg/gm (>1 gm/kg) infected tissue. However, in order to obtain a clone that was very efficiently delivered by agroinfection, those researchers performed extensive modification of the TMV sequence (Marillonnet et al., 2005). Putative cryptic introns in the TMV cDNA were destroyed by point mutagensis and multiple plant introns were inserted to various regions of the TMV cDNA. In the final optimized construct, over 100 point mutations and 16 introns were inserted into the TMV cDNA. These modifications resulted in a significant increase in agroinfection efficiency of the clone, but also increased the size of the modified Agrobacterium Ti plasmid containing the TMV vector. As plasmid size increases, cloning additional sequences into the plasmid becomes more challenging.

In contrast, the pJL-TRBO vector is less than 11 Kb, smaller than the optimized vector described by Marillonnet et al. (Marillonnet et al., 2005), and is therefore easier to clone into desired plants and the like. Also, since not every protein is expressed from a viral vector, it cannot be accumulated to very high levels. The results in FIGS. 14A and 14B demonstrate that some proteins accumulate to levels greater than GFP. Other proteins may then accumulate to levels significantly lower than GFP since there are, no doubt, effects of protein stability that may be involved in the final accumulation level of any protein. Regardless, the high expression capacity of the JL-TRBO expression vector provides an excellent opportunity for detectable levels of recombinant protein to be produced in plants in a very short time frame.

The TMV over-expression vector JL-TRBO, which lacks the TMV CP gene, has several useful advantages over a TMV vector that does express the CP gene. These advantages include: higher agroinfection rates, easier scale up, higher protein expression levels, and bio-containment/protein purification advantages. The TRBO expression vector can express proteins at up to 100 times the level of the routinely used 'enhanced' Agrobacterium transient expression method of co-introduction of a gene of interest and the p19 RNA silencing suppressor gene into plants.

In addition, the pJL-TRBO vector is very useful for rapidly expressing recombinant proteins in plants. The ease-of-use of this expression vector system will make it accessible to a wide range of researchers in plant biology and biotechnology.

Materials and Methods for Example II:

Plasmid construction: pJL24 is a 35S promoter driven version of the TMV expression vector "30B-GFP" (Shivprasad et al., 1999). The TMV vector 30B is a chimera of sequences from the U1 and U5 strains of TMV (The CP subgenomic promoter, CP ORF and 3' non-translated sequences from the U5 strain of TMV, the remainder from the U1 strain). pJL-TRBO was constructed from pJL24 and a full length cDNA clone of TMV U1 using standard cloning procedures.

The final sequence of TRBO is as follows: TMV U1 nts 1-5756 [SEQ ID NO: 13] (with the CP start codon, nts 5712-5714 [SEQ ID NO: 15], mutated from ATG to AGA): the polylinker sequence, ttaattaacggccta gggcggccgc [SEQ ID NO: 16]; then U1 nts 6177 to 6395 [SEQ ID NO: 17]. Numbering of U1 nt sequences was as according to Dawson et al (Dawson et al., 1986). Immediately following U1 nt 6395 are a KpnI site, a ribozyme cDNA sequence (Turpen et al., 1993)

and CaMV 3' polyA signal/transcription terminator (Carrington and Freed, 1990). All plasmids had the mini binary plasmid pCB301 (Xiang et al., 1999) as their backbone, which can replicate in both *E. coli* and *A. tumefaciens*.

In certain non-limiting examples, PCR products of the following genes were cloned into PacI-AvrII digested pJL-TRBO:

a) Green Fluorescent protein (GFP) (Crameri et al., 1996);
b) GFP tagged at its C-terminus with His6(HA)$_2$ (6×His tag disclosed as [SEQ ID NO: 19]);
c) *A. thaliana* adenosine kinase (Wang et al., 2003);
d) 10th domain of human fibronectin (Baron et al., 1991);
e) *Phytopthora infestans* avirulence protein Avr3a (Armstrong et al., 2005); tomato (*Lycopersicon esculentum*) 69 kDa proteinase (Tian et al., 2007); *L. esculentum* cysteine proteinase RCR-3 (Dixon et al., 2000; Tian et al., 2007). The adenosine kinase gene was received from David Bisaro. The fibronectin domain coding sequence was chemically synthesized. The *Phytophthora* and tomato genes were received from Sophie Kamoun.

Agroinfection: Binary plasmids purified from *E. coli* cultures were transformed into *A. tumefaciens* GV3101 using the freeze thaw method (Chen et al., 1994). Transformed *A. tumefaciens* were plated on LB plates with 50 μg/ml Kanamycin, 25 μg/ml gentamycin and 10 μg/ml rifampicin for plasmid selection. Binary plasmid transformed *A. tumefaciens* cells were grown (12 to 24 hours) at 25-28° C., 225 rpm in LB media (Sambrook et al., 1989) supplemented with 10 mM MES pH 5.7, 50 μg/ml Kanamycin, 25 μg/ml gentamycin. Overnight cultures were diluted 1:10 in the same media supplemented with 20 μM acetosyringone and grown as above to an OD$_{600}$ of about 1.0. Cells were collected by centrifugation and resuspended in induction media (Johansen and Carrington, 2001), 10 mM MES, pH 5.7, 10 mM MgCl$_2$, 200 μM acetosyringone, at an OD$_{600}$ of 1.0. Cells sat at room temperature in induction media for 2 to 24 hours before infiltration into the abaxial surface of *N. benthamiana* leaves using a 1 ml syringe with no needle. When mixed cultures of *A. tumefaciens* were infiltrated into plants, bacterial cultures were prepared separately in induction media and were combined immediately before infiltration.

Plants and photography: *Nicotiana benthamiana* plants were grown in a growth chamber with 18 hour photoperiod, 25-27° C. For GFP photography, plants were photographed with a Cannon G6 digital camera equipped with a Tiffen Deep Yellow 15 filter. Plants were illuminated with a hand-held long wave UV lamp (UVP Blak-Ray Model UVL-56).

SDS-PAGE: Total soluble protein extracts of agro-infiltrated plant tissue were prepared by freezing tissue samples in liquid nitrogen and then grinding in the presence of 4 volumes (per gram fresh weight) 50 mM Tris, pH 7.5, 150 mM NaCl, 0.1% Tween-20, 0.1% beta-mercaptoethanol (BMe). Extracts were clarified by centrifuging for 15 minutes at 12-15 K×g at 4° C. Clarified supernatant was stored at −20° C. Equal volumes of clarified extract of each treatment were combined with SDS-PAGE loading dye (Laemmli, 1970) and analyzed on 4-20% SDS-PAGE gels. Gels were stained with Coomassie blue to visualize proteins.

GFP Assay: Samples of clarified plant protein extracts, prepared as described herein, (or standards of purified GFP) were diluted in 50 mM Carbonate buffer (pH 9.6). Protein samples in wells of a 96-well plate (Costar, white polystyrene) were read on a Perkin-Elmer HTS 7000 BioAssay Reader with 405 nm excitation/535 emission filters.

Purification of His6Tagged GFP (6×His tag disclosed as [SEQ ID NO: 19]): His6 C-terminally tagged GFP (6×His tag disclosed as [SEQ ID NO: 19]) was expressed in plants from a TRBO replicon by agroinfection. Plant tissue was collected at 5 DPI and ground in 4 volumes extraction buffer (50 mM phosphate pH 8.0, 10 mM Tris, pH8.0, 500 mM NaCl, 0.1% Tween-20, 0.1% NP-40, 0.1% BMe, 1 mM PMSF). Extract was filtered thru cheesecloth then centrifuged at 12,000×g, 4° C. for 20 minutes. Clarified supernatant was then passed through a −20° C. freeze thaw cycle. After thawing, samples were centrifuged (as before). Immidazole was added to supernatant for a final concentration of 10 mM. One-half ml of washed Ni-NTA agarose beads (Qiagen) were added to 8-10 mls of extract and incubated at 4° C. on rocker for 1-2 hours. Column was washed in 20-25 column volumes wash buffer (50 mM phosphate pH 8.0, 500 mM NaCl, 0.1% Tween-20, 20 mM immidazole). Bound His-tagged GFP was eluted with 250 mM immidazole in 1×PBS. Eluted fraction was dialized twice (6 hours to overnight) into 1000 volumes 1×PBS (11.9 mM phosphate, pH 7.4, 137 mM NaCl, 2.7 mM KCl) at 4° C. Protein concentration was estimated using BCA assay (Pierce) and bovine serum albumin as a standard.

EXAMPLE III

RNA silencing suppressors increase the agroinfection frequency of a 35S driven TMV-GFP vector. In this experiment, the approach was to co-introduce T-DNAs for 35S:TMV-GFP and 35S:p19 into plant cell. (p19 is a potent RNA silencing suppressor from tomato bushy stunt virus). The procedure includes mixing agro cultures containing binary plasmids, infiltrating, and observing under UV light.

The results, as shown in FIGS. 15A and 15B, shows complete infection by 4DPI where nearly every cell in the infiltrated zone is infected by the TMV-GFP construct. FIGS. 16A-16C show leaves under fluorescent microscope (low power). The SDS PAGE shown in FIG. 16C demonstrates that GFP is detectable by SDS PAGE in crude plant extracts.

EXAMPLE IV

TRBO charging protein expression: The TMV CP gene affects agroinfection frequency, and the p19 enhances agroinfection rate of 35S:TMV-GFP. It now shown that the agroinfection of 35S:TMV GFP ΔCP is efficient without p19. See FIGS. 17A and 17B.

Also, dilute cultures of Agro/35:TMV-GFP ΔCP can infect plants. FIG. 18 shows *N. benthamiana* leaves infiltrated with 1:50 dilution of Agro/35S:TMV-GFP ΔCP about 60 μl Agro cultures into 3 ml is sufficient for at least 4 plants. FIG. 19 shows the SDS-PAGE analysis of protein extract where plants were infiltrated with Agro/35S:TMV-GFP ΔCP, extracts were made at various times post infiltration, the SDS-PAGE was run with 50 μl protein/lane, and stained with Coomassie Blue. The day 6 sample has about 4 GFP/50 μg TSP. H=healthy plant extract; YFP-V5His6 standard from *E. coli*.

Also, FIG. 20 shows a comparison of protein expression vectors on the lame leaf: 35S:GFP, in the upper left quadrant of the leaf; 35S:GFP+35S:p19, in the upper right quadrant; 35S:TMV:GFP+35S: p19, in the lower left quadrant; and 25S:TMV:GFP ΔCP+35S:p19 (pJL-TRBO-G), in the lower right quadrant.

EXAMPLE V

Protoplasts were generated from pJL48 (pJL-TRBO):GFP infiltrated *N benthamiana* leaf, as shown in FIGS. 21A-21B, showing protoplasts made 6 DPI, 2.5 hour digest in enzyme solution.

FIG. 21A: a photograph, taken under white light, showing protoplasts were generated from pJL48 (pJL-TRBO):GFP infiltrated N. benthamiana leaf, showing protoplasts made 6 DPI, 2.5 hour digest in enzyme solution. FIG. 21B: a photograph, taken under UV light, showing protoplasts were generated from pJL48 (pJL-TRBO):GFP infiltrated N. benthamiana leaf, showing protoplasts made 6 DPI, 2.5 hour digest in enzyme solution.

EXAMPLE VI

The vector pJL66 [SEQ ID NO:14] includes a 35S driven DNA encoding for a replicon comprised of sequences from the U1 and U5 strains of TMV in a binary vector backbone, wherein the replicon generated from the transcription of pJL66 is lacking a CP orf. One method for constructing pJL66 includes deleting nucleotides 5788 to 6608 from pJL36.

FIG. 22 shows the pJL66 DNA sequence [SEQ ID NO:14] which includes a 35S driven DNA encoding for a replicon comprised of sequences from the U1 and U5 strains of TMV in a binary vector backbone, where the replicon generated from the transcription of pJL66 is lacking a CP orf. FIG. 23 contains the pJL66 data sheet showing—Binary vector, Kan resistance, T-DNA borders not shown in map. pJL66 is a deletion mutant of pJL24. All sequences downstream of GFP stop codon to last 4 codons of U5 CP were deleted from pJL24.

FIG. 24 contains photographs of plants infected with the TMV vector encoded in pJL66 via agroinfiltration/agroinfection. The TMV vector in pJL66 can efficiently infected N. benthamiana cells in the presence or absence of an RNA silencing suppressor (e.g., p19). The efficiency is comparable to that obtained with GFP-expressing TRBO (which is also in the figure for comparison). TMV vector in binary plasmid pJL66 can be efficiently delivered to plants via agroinfection in the presence or absence of co-expression of an RNA silencing suppressor gene. Treatments: 1=co-infiltrated with Agrobacterium cultures Agro/pJL66+Agro/pJL3:p19. 2=Infiltrated with Agro/pJL66 only. 3=co-infiltrated with Agro/pJL-TRBO-G+Agro/pJL3:p19. 4=infiltrated with Agro/pJL-TRBO-G only. Photo under UV light 5 days post infiltration.

The following Table 2 shows the SEQ ID Nos., as used herein:

TABLE 2

Listing of SEQ ID Nos.:

[SEQ ID NO: 1]
primer
JAL 228 (GTATTTTACAACAATTACCAAC)

[SEQ ID NO: 2]
reverse direction primer
JAL 229 (GGGCCTAGGCTATGACCATGATTACGC)

[SEQ ID NO: 3]
Overlapping oligonucleotides
JAL 230 (taacggcctagggcggccgc)
and

[SEQ ID NO: 4]
JAL 231 (tcgagcggccgccctaggccgttaat)

[SEQ ID NO: 5]
pJL36 (see FIG. 5B)

[SEQ ID NO: 6]
the V5 epitope
(amino acid sequence GKPIPNPLLGLD)

TABLE 2-continued

Listing of SEQ ID Nos.:

[SEQ ID NO: 7]
the DNA cassette (top stand sequence:
(CGAGGCCAGAAGAGCAACCTTTACGTACTTGCTCTTCAGCTTGAAGGT
AAGCCTATCCCTAACCCTCTCCTCGGTCTCGATTCTACGCGTACCGGTC
ATCATCACCATCACCATTGAC)

[SEQ ID NO: 8]
plasmid
pJL43 (see FIG. 2)

[SEQ ID NO: 9]
JAL 55 (cccttaattaa cATGgaa cgagctata caaggaaac)

[SEQ ID NO: 10]
reverse direction
oligo JAL 11 (ccctactagtcTTActcgccttcttttttcgaa)

[SEQ ID NO: 11]
F primer
JAL 286 (GGCCT aaa atggctagcaaaggagaag)

[SEQ ID NO: 12]
R primer J
AL 287 (Gcttatttgtagagctcatccat)

[SEQ ID No: 13]
pJL48 (pJL-TRBO) (see FIG. 7B)

[SEQ ID NO: 14]
pJL66 (see FIG. 22)

[SEQ ID NO: 15]
(with the CP start codon, nts 5712-5714 mutated from ATG to AGA):

[SEQ ID NO: 16]
the polylinker sequence, ttaattaacggcctagggcggccgc

[SEQ ID NO: 17]
U1 nts 6177 to 6395

[SEQ ID BO: 18]
ATCGAggcctt

[SEQ ID NO: 19]
6x His tag

[SEQ ID NO: 20]),
the influenza hemagglutinin peptide YPYDVPDYA)

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

References

The publication and other material used herein to illuminate the invention or provide additional details respecting the practice of the invention, are incorporated be reference herein, and for convenience are provided in the following bibliography.

Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

Armstrong M R, Whisson S C, Pritchard L, Bos J I, Venter E, Avrova A O, Rehmany A P, Bohme U, Brooks K, Cherevach I, Hamlin N, White B, Fraser A, Lord A, Quail M A, Churcher C, Hall N, Berriman M, Huang S, Kamoun S, Beynon J L, Birch P R (2005) An ancestral oomycete locus contains late blight avirulence gene Avr3a, encoding a protein that is recognized in the host cytoplasm. Proc Natl Acad Sci USA 102: 7766-771.

Aslanidis C, de Jong P J (1990) Ligation-independent cloning of PCR products (LICPCR). Nucleic Acids Res 18(20): 6069-74.

Baron M, Norman D G, Campbell I D (1991) Protein modules. Trends Biochem Sci 16: 13-17 Beck D L, Dawson W O (1990) Deletion of repeated sequences from tobacco mosaic virus mutants with two coat protein genes. Virology 177: 462-469.

Breiteneder H, Krebitz M, Wiedermann U, Wagner B, Essl D, Steinkellner H, Turpen T H, Ebner C, Buck D, Niggemann B and others (2001) Rapid production of recombinant allergens in Nicotiana benthamiana and their impact on diagnosis and therapy. hit Arch Allergy Immunol 124(1-3):48-50.

Buchholz F, Bishop M (2001) LoxP-directed cloning: use of Cre recombinase as a universal restriction enzyme. Biotechniques 31(4):906-8, 910, 912, 914, 916, 918. Carrington J C, Freed D D (1990) Cap-independent enhancement of translation by a plant potyvirus 5' nontranslated region. J Virol 64: 1590-1597.

Chalfie M (1995) Green fluorescent protein. Photochem Photobiol 62: 651-656.

Chalfie M, Tu Y, Euskirchen G, Ward W W, Prasher D C (1994) Green fluorescent protein as a marker for gene expression. Science 263: 802-805.

Chen H, Nelson R S, Sherwood J L (1994) Enhanced recovery of transformants of Agrobacterium tumefaciens after freeze-thaw transformation and drug selection. Biotechniques 16: 664-668, 670.

Crameri A, Whitehorn E A, Tate E, Stemmer W P (1996) Improved green fluorescent protein by molecular evolution using DNA shuffling. Nat Biotechnol 14: 315-319.

Creager ΔN, Scholthof K B, Citovsky V, Scholthof H B (1999) Tobacco mosaic virus. Pioneering research for a century. Plant Cell 11: 301-308.

Culver J N, Lehto K, Close S M, Hilf M E, Dawson W O (1993) Genomic position affects the expression of tobacco mosaic virus movement and coat protein genes. Proc Natl Acad Sci USA 90: 2055-2059.

Dawson W O, Beck D L, Knorr D A, Grantham G L (1986) cDNA cloning of the complete genome of tobacco mosaic virus and production of infectious transcripts. Proc Natl Acad Sci USA 83: 1832-1836.

Dawson W O, Lewandowski D J, Hilf M E, Bubrick P, Raffo A J, Shaw J J, Grantham G L, Desjardins P R (1989) A tobacco mosaic virus-hybrid expresses and loses an added gene. Virology 172: 285-292.

Dessens J T, Lomonossoff G P (1993) Cauliflower mosaic virus 35S promoter-controlled DNA copies of cowpea mosaic virus RNAs are infectious on plants. J Gen Virol 74 (Pt 5):889-92.

Dixon M S, Golstein C, Thomas C M, van Der Biezen E A, Jones J D (2000) Genetic complexity of pathogen perception by plants: the example of Rcr3, a tomato gene required specifically by Cf-2. Proc Natl Acad Sci USA 97: 8807-8814.

Donson J, Kearney C M, Hilf M E, Dawson W O (1991) Systemic expression of a bacterial gene by a tobacco mosaic virus-based vector. Proc Natl Acad Sci USA 88: 7204-7208

Filipowicz W (2005) RNAi: the nuts and bolts of the RISC machine. Cell 122(1):17-20.

Fitzmaurice W P, Holzberg S, Lindbo J A, Padgett H S, Palmer K E, Wolfe G M, Pogue G P (2002) Epigenetic modification of plants with systemic RNA viruses. Omics (2):137-51.

Gleba Y, Klimyuk V, Marillonnet S (2005) Magnifection—a new platform for expressing recombinant vaccines in plants. Vaccine 23: 2042-2048.

Gleba Y, Klimyuk V, Marillonnet S (2007) Viral vectors for the expression of proteins in plants. Curr Opin Biotechnol 18: 134-141.

Grimsley N (1995) Agroinfection. Methods Mol Biol 44: 325-342.

Grimsley N, Hohn B, Hohn T, Walden R (1986) "Agroinfection," an alternative route for viral infection of plants by using the Ti plasmid. Proc Natl Acad Sci USA 83: 3282-3286

Giritch A, Marillonnet S, Engler C, van Eldik G, Botterman J, Klimyuk V, Gleba Y (2006) Rapid high-yield expression of full-size IgG antibodies in plants coinfected with noncompeting viral vectors. Proc Natl Acad Sci USA.

Johansen L K, Carrington J C (2001) Silencing on the spot. Induction and suppression of RNA silencing in the Agrobacterium-mediated transient expression system. Plant Physiol 126(3):930-8.

Krebitz M, Wiedermann U, Essl D, Steinkellner H, Wagner B, Turpen T H, Ebner C, Schemer O, Breiteneder H (2000) Rapid production of the major birch pollen allergen Bet v 1 in Nicotiana benthamiana plants and its immunological in vitro and in vivo characterization. Faseb J 14(10):1279-88.

Kumagai M H, Donson J, della-Cioppa G, Harvey D, Hanley K, Grill L K (1995) Cytoplasmic inhibition of carotenoid biosynthesis with virus-derived RNA. Proc Natl Acad Sci USA 92(5):1679-83.

Kumagai M H, Turpen T H, Weinzettl N, della-Cioppa G, Turpen A M, Donson J, Hilf M E, Grantham G L, Dawson W O, Chow T P and others (1993) Rapid, high-level expression of biologically active alpha-trichosanthin in transfected plants by an RNA viral vector. Proc Natl Acad Sci USA 90(2):427-30.

Laemmli U K (1970) Cleavage of structural proteins during the assembly of the head of bacteriophage T4. Nature 227: 680-685.

Lehto K, Dawson W O (1990) Replication, stability, and gene expression of tobacco mosaic virus mutants with a second 30K ORF. Virology 175: 30-40.

Liu Q, Li M Z, Leibham D, Cortez D, Elledge S J (1998) The univector plasmid-fusion system, a method for rapid construction of recombinant DNA without restriction enzymes. Curr Biol 8(24):1300-9.

Liu Q, Li M Z, Liu D, Elledge S J (2000) Rapid construction of recombinant DNA by the univector plasmid-fusion system. Methods Enzymol 328:530-49.

Ma Q, Zhou L, Ma L, Huo K (2006) Directional and direct cloning strategy for high-throughput generation of recombinant baculoviruses. Biotechniques 41:453-458.

Man M, Epel B L (2006) Assessment of the effectiveness of a nuclear-launched TMV-based replicon as a tool for foreign gene expression in plants in comparison to direct gene expression from a nuclear promoter. Transgenic Res 15: 107-113.

Marillonnet S, Thoeringer C, Kandzia R, Klimyuk V, Gleba Y (2005) Systemic *Agrobacterium tumefaciens*-mediated transfection of viral replicons for efficient transient expression in plants. Nat Biotechnol 23: 718-723.

Marillonnet S, Giritch A, Gils M, Kandzia R, Klimyuk V, Gleba Y (2004) In planta engineering of viral RNA replicons: efficient assembly by recombination of DNA modules delivered by *Agrobacterium*. Proc Natl Acad Sci USA 101(18):6852-7.

McCormick A A, Kumagai M E, Hanley K, Turpen T H, Hakim I, Grill L K, Tuse D, Levy S, Levy R (1999) Rapid production of specific vaccines for lymphoma by expression of the tumor-derived single-chain Fv epitopes in tobacco plants. Proc Natl Acad Sci U S A 96(2):703-8.

Pogue G P, Lindbo J A, Dawson W O, Turpen T H, editors (1998) Tobamovirus transient expression vectors: Tools for plant biology and high-level expression of foreign proteins in plants. Dordrecht, The Netherlands: Kluwer Academic Publishers.

Pogue G P, Lindbo J A, Garger S J, Fitzmaurice W P (2002) Making an ally from an enemy: plant virology and the new agriculture. Annu Rev Phytopathol 40: 45-74.

Popescu S C, Popescu G V, Bachan S, Zhang Z, Seay M, Gerstein M, Snyder M, Dinesh-Kumar S P (2007) Differential binding of calmodulin-related proteins to their targets revealed through high-density *Arabidopsis* protein microarrays. Proc Natl Acad Sci U S A 104: 4730-4735.

Sambrook J, Fritsch E F, Maniatis T (1989) Molecular Cloning: A laboratory manual. Cold Spring Harbor Laboratory Press 2nd Ed.

Scholthof H B, Scholthof K B, Jackson A O (1996) Plant virus gene vectors for transient expression of foreign proteins in plants. Annu Rev Phytopathol 34: 299-323.

Scholthof K B, Mirkov T E, Scholthof H B (2002) Plant virus gene vectors: biotechnology applications in agriculture and medicine. Genet Eng (NY) 24:67-85.

Scholthof K B (2004) Tobacco mosaic virus: a model system for plant biology. Annu Rev Phytopathol 42: 13-34.

Shivprasad S, Pogue G P, Lewandowski D J, Hidalgo J, Donson J, Grill L K, Dawson W O (1999) Heterologous sequences greatly affect foreign gene expression in tobacco mosaic virus-based vectors. Virology 255: 312-323.

Shuman S (1994) Novel approach to molecular cloning and polynucleotide synthesis using vaccinia DNA topoisomerase. J Biol Chem 269(51):32678-84.

Tian M, Win J, Song J, van der Hoorn R, van der Knaap E, Kamoun S (2007) A *Phytophthora infestans* cystatin-like protein targets a novel tomato papain-like apoplastic protease. Plant Physiol 143: 364-377.

Toth R L, Pogue G P, Chapman S (2002) Improvement of the movement and host range properties of a plant virus vector through DNA shuffling. Plant J 30: 593-600.

Turpen T H, Turpen A M, Weinzettl N, Kumagai M H, Dawson W O (1993) Transfection of whole plants from wounds inoculated with *Agrobacterium tumefaciens* containing cDNA of tobacco mosaic virus. J Virol Methods 42: 227-239.

Turpen T H, Reinl S J, Charoenvit Y, Hoffman S L, Fallarme V, Grill L K (1995) Malarial epitopes expressed on the surface of recombinant tobacco mosaic virus. Biotechnology (NY) 13(1):53-7.

Voinnet O, Rivas S, Mestre P, Baulcombe D (2003) An enhanced transient expression system in plants based on suppression of gene silencing by the p19 protein of tomato bushy stunt virus. Plant J 33: 949-956.

Walhout A J, Temple G F, Brasch M A, Hartley J L, Lorson M A, van den Heuvel S, Vidal M (2000) GATEWAY recombinational cloning: application to the cloning of large numbers of open reading frames or ORFeomes. Methods Enzymol 328:575-92.

Wang H, Hao L, Shung C Y, Sunter G, Bisaro D M (2003) Adenosine kinase is inactivated by geminivirus AL2 and L2 proteins. Plant Cell 15: 3020-3032.

Xiang C, Han P, Lutziger I, Wang K, Oliver D J (1999) A mini binary vector series for plant transformation. Plant Mol Biol 40: 711-717.

Yusibov V, Shivprasad S, Turpen T H, Dawson W, Koprowski H (1999) Plant viral vectors based on tobamoviruses. Curr Top Microbiol Immunol 240:81-94.

What is claimed is:

1. A vector comprising pJL48 (pJL-TRBO) [having a size of about 11 kb or less, and] having the isolated nucleic acid sequence of SEQ ID NO: 13, wherein the isolate nucleic acid sequence is operatively linked to a promoter for expression in a plant cell, and includes a 35S driven Tobacco Mosaic Virus TMV expression vector in a binary vector backbone, wherein a replicon generated from the transcription of pJL48 (pJL-TRBO) is lacking a coat protein open reading frame (CP orf) and is capable of expression of a desired product in plants;

wherein the pJL-TRBO vector, when in the plant, increases expression rate of the desired product in comparison with corresponding wild type plants that do not contain the pJL-TRBO vector;

and wherein the pJL-TRBO vector does not generate virion particles, yet demonstrates the ability to synchronously inoculate large numbers of cells in a leaf of the plant.

2. The vector of claim 1, further comprising at least one isolated nucleotide sequence which comprises SEQ ID NOs: 15, 16 or 17; or a nucleotide sequence which encodes the same sequence of amino acids as encoded by the nucleotide sequence shown in SEQ ID NOs: 15, 16, 17.

3. The vector of claim 1, wherein the promoter is Cauliflower mosaic virus CaVM35S promoter.

4. A plant cell transformed with the vector of claim 1.

5. A method for making a pJL48 (pJL-TRBO) vector, comprising:

i) deleting a coat protein gene and 3' non-translated tobamovirus sequences in a vector pJL36, the vector pJL36 comprising the isolated nucleic acid sequence of SEQ ID NO: 5, and ii) replacing the deleted sequences of i) with nucleotides numbered 6177 to 6395 as numbered from nucleotide #1 of TMV U1 strain shown in SEQ ID NO:5 as numbered from the first nucleotide of SEQ ID NO:5, [wherein the pJL-TRBO vector has a size of about 11 kb or less,]

wherein the pJL-TRBO vector, when in the plant, increases expression rate of the desired product in comparison with corresponding wild type plants that do not contain the pJL-TRBO vector; and wherein the pJL-TRBO vector does not generate virion particles, yet demonstrates the ability to synchronously inoculate large numbers of cells in a leaf of the plant.

6. A method of agroinfection comprising infecting at least one plant cell with the vector of claim 5, pJL48 (pJL-TRBO), without any co-expression of an RNA silencing suppressor.

7. The method for agroinfection of claim 6, comprising infecting the plant cell with pJL48 (pJL-TRBO) in Agrobacterium cultures diluted 10, 20, 50 or 100 or more fold (from an initial culture $OD_{600}$ of 1.0).

8. The method of claim 6, wherein the vector includes a second sequence which encodes for a protein that has RNA silencing suppression functions.

9. The method of claim 6, wherein the vector includes a second sequence which encodes for the protein P19 from Tomato bushy stunt virus.

10. The method of claim 6, wherein the vector includes a second sequence which encodes for one or more of the following genes: P0 protein gene from a polerovirus, HC-Pro protein gene from a potyvirus, CP from turnip crinkle or related viruses, or P21 from beet yellows closterovirus.

11. The method of claim 6, further including introducing a promoter driven version of a first gene of interest into the plant cells by agroinfiltration at the same time, or either before or after, pJL48 (pJL-TRBO) vector expressing a second gene of interest is introduced into the plant cells.

12. The vector of claim 1, further including at least one promoter, wherein the promoter is Cauliflower mosaic virus CaVM35S promoter.

13. A plant cell transformed with the vector of claim 1.

14. The vector of claim 1, wherein the vector includes a second sequence which encodes for a gene that has RNA silencing suppression functions.

15. The vector of claim 1, wherein the vector includes a second sequence which encodes for protein P19 from Tomato bushy stunt virus.

16. The vector of claim 1, wherein vector includes a second sequence which encodes for one or more: P0 protein gene from a polerovirus, HC-Pro protein gene from a potyvirus, CP from turnip crinkle or related viruses, or P21 from beet yellows closterovirus.

17. An isolated polynucleotide for activating expression specifically in a plant cell, characterized in that the isolated polynucleotide comprises the vector of claim 1.

18. A method for producing a transgenic plant cell of the transgenic plant that contain the vector of claim 1, comprising:

transforming the vector of claim 1 into at least one plant cell to produce a transgenic plant cell or transgenic plant tissue; and cultivating the transgenic plant cell or transgenic plant tissue to produce a transgenic plant or tissue or cell of the transgenic plant containing the vector of claim 1.

19. The method as recited in claim 18, wherein transforming is achieved by an Agrobacterium tumefaciens-mediating method.

20. A recombinant pJL48 (pJL-TRBO) vector comprising the isolated nucleic acid sequence of SEQ ID No. 13, [wherein the pJL-TRBO vector has a size of about 11 kb or less,] and is stably integrated in the genome of a plant cell, and the recombinant vector has a plasmid map shown in FIG. 6, and when stably integrated in the genome of a plant cell, the recombinant pJL-TRBO vector has an increased expression rate of at least one product in comparison with corresponding wild type plants that do not contain the pJL-TRBO vector; and wherein the pJL-TRBO vector does not generate virion particles, yet demonstrates the ability to synchronously inoculate large numbers of cells in a leaf of the plant.

21. The vector of claim 1, having restriction sites: PAcI, AvrII and NotI.

* * * * *

UNITED STATES PATENT AND TRADEMARK OFFICE
CERTIFICATE OF CORRECTION

PATENT NO. : 8,936,937 B2  
APPLICATION NO. : 12/524812  
DATED : January 20, 2015  
INVENTOR(S) : John A. Lindbo Page 1 of 1

It is certified that error appears in the above-identified patent and that said Letters Patent is hereby corrected as shown below:

In the Claims

Column 73, Claim 1, Line 19, delete "[having a size";

Column 73, Claim 1, Line 20, delete "of about 11 kb or less, and]";

Column 73, Claim 2, Line 37, delete "16or" and insert --16 or--;

Column 73, Claim 5, Line 50, delete "6395as" and insert --6395 as--;

Column 73, Claim 5, Line 52, delete "[wherein the";

Column 73, Claim 5, Line 53, delete "pJL-TRBO vector has a size of about 11 kb or less,]";

Column 74, Claim 20, line 67, delete "[wherein the pJL-TRBO vector has a size of about 11 kb or";

Column 75, Claim 20, line 1, delete "less,]".

Signed and Sealed this  
Twenty-first Day of April, 2015

Michelle K. Lee  
*Director of the United States Patent and Trademark Office*